(12) United States Patent
Lam et al.

(10) Patent No.: US 7,576,175 B2
(45) Date of Patent: Aug. 18, 2009

(54) ALPHA-4 BETA-1 INTEGRIN LIGANDS FOR IMAGING AND THERAPY

(75) Inventors: Kit S. Lam, Davis, CA (US); Ruiwu Liu, Sacramento, CA (US); Li Peng, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 78 days.

(21) Appl. No.: 11/140,548

(22) Filed: May 26, 2005

(65) Prior Publication Data

US 2006/0019900 A1 Jan. 26, 2006

Related U.S. Application Data

(60) Provisional application No. 60/575,586, filed on May 27, 2004.

(51) Int. Cl.
- C07K 5/08 (2006.01)
- C07K 5/10 (2006.01)
- C07K 7/04 (2006.01)
- C07K 7/08 (2006.01)
- C07K 14/00 (2006.01)
- C07K 1/00 (2006.01)
- C07K 1/107 (2006.01)
- A61K 38/06 (2006.01)
- A61K 38/07 (2006.01)
- A61K 38/08 (2006.01)
- A61K 38/10 (2006.01)
- A61K 38/16 (2006.01)

(52) U.S. Cl. ................ 530/331; 530/326; 530/327; 530/328; 530/329; 530/330; 530/333; 530/345; 514/13; 514/14; 514/15; 514/16; 514/17; 514/18

(58) Field of Classification Search .................. None
See application file for complete search history.

(56) References Cited

U.S. PATENT DOCUMENTS

6,248,713 B1 * 6/2001 Lin et al. ............. 514/2

FOREIGN PATENT DOCUMENTS

| WO | WO 9703094 A1 * 1/1997 |
| WO | WO 9842656 A1 * 10/1998 |

OTHER PUBLICATIONS

L.L. Chen et al. Biochemistry (1998) 37(24), pp. 8743-8753.*
Aina et al., "Therapeutic Cancer Targeting Peptides. Biopolymers," *Peptide Science*, 66:184-199, (2002).
Barnes et al., "Recent developments in the encoding and deconvolution of combinatorial libraries," *Curr. Opin. Chem. Biol.* 4:346-350 (2000).
Chait et al., "Protein ladder sequencing," *Science* 262:89-92 (1993).
Chen et al., "Identification of Ligand Binding Sites on Integrin 41 through Chemical Cross-Linking," *Biochem.*, 37:8743-8753 (1998).
Chen et al., "One bead-one compound combinatorial peptide library: different types of screening," *Methods Enzymol.* 267:211-219 (1996).
Coiffier et al., "Rituximab (Anti-CD20 Monoclonal Antibody) for the Treatment of Patients With Relapsing or Refractory Aggressive Lymphoma: A Multicenter Phase II Study," *Blood*, 92(6):1927-1932 (1998).
Czarnik, "Encoding methods for combinatorial chemistry," *Curr Opin. Chem. Biol.* 1: 60-66 (1997).
Damiano et al., "Integrin-mediated drug resistance in multiple myeloma," *Leuk. Lymphoma*. 38: 71-81 (2000).
De La Fuente et al., "Fibronectin interaction with 4β1 integrin prevents apoptosis in B cell chronic lymphocytic leukemia: correlation with Bcl-2 and Bax," *Leukemia* 13:266-274 (1999).
Foon et al., "Are Solid Tumor Anti-Idiotype Vaccines Ready for Prime Time?" *Clin. Cancer Res.* 7:1112-1115 (2001).
Klominek et al., "Differential motile response of human malignant mesothelioma cells to fibronectin, laminin and collagen type IV: The role of 1 integrins," *Int. J. Cancer*, 72:1034-1044 (1997).
Hemler, "VLA proteins in the integrin family: structures, functions, and their role on leukocytes," *Ann. Rev. Immunol.*, 8:365 (1990).
Holzmann et al., "4 integrins and tumor metastasis," *Curr. Top. Microbiol. Immunol.*, 231:125-141 (1998).
Hood et al., "Role of integrins in. cell invasion and migration," *Nat. Rev. Cancer*, 2:91-100 (2002).
Hynes, "Integrins: bidirectional, allosteric signaling machines," *Cell*, 110:673-687 (2002).
Hynes, "Integrins: versatility, modulation and signaling in cell adhesion," *Cell*, 69:11-25 (1992).
Jin et al., "Integrins: roles in cancer development and as treatment targets," *Brit. J. Cancer*, 90:561-565 (2004).
Kwekkeboom et al., "Peptide Receptor Imaging and Therapy," *J. Nucl. Med.* 41:1704-1713 (2000).
Okarvi, "Peptide-based radiopharmaceuticals: Future tools for diagnostic imaging of cancers and other diseases," *Med. Res. Rev.* 24(3):357-359 (2004).
Lam et al., "The "One-Bead-One-Compound" Combinatorial Library Method," *Chem. Rev.* 97(2):411-448 (1997).
Lam et al., "A new type of synthetic peptide library for identifying ligand-binding activity," *Nature*, 354:82-84 (1991).

(Continued)

*Primary Examiner*—Andrew D Kosar
(74) *Attorney, Agent, or Firm*—Townsend and Townsend and Crew LLP

(57) ABSTRACT

The present invention provides $\alpha_4\beta_1$ integrin ligands that display high binding affinity, specificity, and stability. The ligands comprise a peptide having n independently selected amino acids, wherein at least one amino acid is an unnatural amino acid or a D-amino acid, and wherein n is an integer of from 3 to 20. Methods are provided for administering the ligands for treating cancer, inflammatory diseases, and autoimmune diseases. Also provided are methods for administering the ligands for imaging a tumor, organ, or tissue in a subject.

16 Claims, 13 Drawing Sheets

OTHER PUBLICATIONS

Lin et al., "Very late antigen 4 (VLA4) antagonists as anti-inflammatory agents," *Curr Opin. Chem. Biol.* 2(4):453-457 (1998).

Lin et al., "Selective, Tight-binding Inhibitors of Integrin Alpha-4-beta-1 that Inhibit Allergic Airway Responses," *J. Med. Chem.*, 42:920-934 (1999).

Liu et al., "A novel peptide-based encoding system for 'one-bead one-compound' and small molecule combinational libraries," *J. Am. Chem. Soc.*, 124:7678-7680 (2002).

Lowman et al., "Baceriophage display and discovery of peptide leads for drug development," *Annu. Rev. Biophys. Biomol. Struct.*, 26:401-424 (1997).

Marco et al., "Alpha 4 integrin increases anoikis of human osteosarcoma cells.," *J. Cell. Biochem.* 88, 1038-1047 (2003).

Park et al., "The use of one-bead one-compound combinatorial library method to identify peptide ligands for 4β1 integrin receptor in non-Hodgkin's lymphoma," *Lett. Pept. Sci.*, 8:171-178 (2002).

Pasqualini et al., "Organ targeting In vivo using phage display peptide libraries," *Nature* 380:364-366 (1996).

Shimaoka et al., "Conformational Regulation Of Integrin Structure And Function," *Annu. Rev. Biophys. Biomol. Struct.* 31:485-516 (2002).

Song et al., "A novel and rapid encoding method based on mass spectrometry for "one-bead-one-compound" small molecule combinatorial libraries," *J. Am. Chem. Soc.* 125(20):6180-6188 (2003).

Till et al., "The chemokine receptor CCR7 and 4 integrin are important for migration of chronic lymphocytic leukemia cells into lymph nodes," *Blood* 99(8):2977 (2002).

Vincent et al., "Integrin function in chronic lymphocytic leukemia," *Blood* 87(11):4780-4788(1996).

Wang et al., "Encoding method for OBOC small molecule libraries using a biphasic approach for ladder-synthesis of coding tags," *J. Am. Chem. Soc.* 126:5740-5749 (2004).

Youngquist et al., "Generation and screening of combinatorial peptide libraries designed for rapid sequencing by mass-spectrometry," *J. Am. Chem. Soc.* 117, 3900-3906 (1995).

Yusuf-Makagiansar et al., "Inhibition of LFA-1/ICAM-1 and VLA-4/VCAM-1 as a therapeutic approach to inflammation and autoimmune diseases," *Med. Res. Reviews*, 22:146-167 (2002).

\* cited by examiner

BIOTINYLATED LIGAND 2A

BIOTINYLATED LIGAND 3A

Linker

SEQUENCE LISTING

```
<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence:negative
      control unrelated peptide

<400> SEQUENCE: 1

Thr Pro Asn Asn Glu Ile Asp Ser Phe Val Lys Ser Gly Asp Phe
1               5                   10                  15

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:vascular
      cell adhesion molecule-1 (VCAM-1) natural ligand
      recognition site for alpha-4beta-1 integrin

<400> SEQUENCE: 2

Gln Ile Asp Ser
  1

<210> SEQ ID NO 3
<211> LENGTH: 4
<212> TYPE: PRT
<213> ORGANISM: Artificial Sequence
<220> FEATURE:
```

```
<223> OTHER INFORMATION: Description of Artificial Sequence:fibronectin
      (FN) natural ligand recognition site for
      alpha-4beta-1 integrin

<400> SEQUENCE: 3

Ile Leu Asp Val
  1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:X peptide in
      alpha-4beta-1 integrin inhibitor ligand formula
<220> FEATURE:
<221> NAME/KEY: MOD_RES
<222> LOCATION: (1)
<223> OTHER INFORMATION: Xaa = Nle
<220> FEATURE:
<221> NAME/KEY: MOD_RES
<222> LOCATION: (5)
<223> OTHER INFORMATION: Xaa = homocitrulline (HoCit)

<400> SEQUENCE: 4

Xaa Asp Val Pro Xaa Gly
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:X peptide in
      alpha-4beta-1 integrin inhibitor ligand formula
<220> FEATURE:
<221> NAME/KEY: MOD_RES
<222> LOCATION: (1)
<223> OTHER INFORMATION: Xaa = Nle modified by 2-(4-aminophenyl)
      propionic acid
<220> FEATURE:
<221> NAME/KEY: MOD_RES
<222> LOCATION: (5)
<223> OTHER INFORMATION: Xaa = homocitrulline (HoCit)

<400> SEQUENCE: 5

Xaa Asp Val Pro Xaa Gly
  1               5
```

ALPHA-4 BETA-1 INTEGRIN LIGANDS FOR IMAGING AND THERAPY

CROSS-REFERENCES TO RELATED APPLICATIONS

The present application claims priority to U.S. Provisional Application No. 60/575,586, filed May 27, 2004, which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with support from the U.S. Government under Grant (or Contract) No. R33 CA89706, awarded by the National Institute of Health. The Government has certain rights in this invention.

BACKGROUND OF THE INVENTION

Cell adhesion is a process by which cells associate with each other, migrate towards a specific target, or localize within the extracellular matrix. Cell adhesion constitutes one of the fundamental mechanisms underlying numerous biological phenomena. For example, cell adhesion is responsible for the adhesion of hematopoietic cells to endothelial cells and the subsequent migration of those hematopoietic cells out of blood vessels and to the site of injury. As such, cell adhesion plays a role in pathologies such as inflammation, autoimmune disease, and tumor metastasis in mammals.

Investigations into the molecular basis for cell adhesion have revealed that various cell surface macromolecules, collectively known as cell adhesion molecules or receptors, mediate cell-cell and cell-matrix interactions. For example, members of the integrin family of cell surface receptors mediate cell-cell and cell-matrix interactions and regulate cell motility, migration, survival, and proliferation (Hynes, *Cell,* 69:11-25 (1992); Hynes, *Cell,* 110:673-687 (2002)). Integrins are non-covalent heterodimeric complexes consisting of two subunits, $\alpha$ and $\beta$. There are at least 18 different $\alpha$ subunits and at least 8 different $\beta$ subunits.

Integrins are implicated in a variety of diseases and disorders, such as cancer, inflammation, autoimmune diseases, and genetic diseases. For example, $\alpha_5\beta_1$, $\alpha_v\beta_3$, and $\alpha_v\beta_5$ integrins play critical roles in promoting tumor metastasis and angiogenesis (Hood and Cheresh, *Nat. Rev. Cancer,* 2:91-100 (2002); Jin and Varner, *Brit. J Cancer,* 90:561-565 (2004)). In addition, $\alpha_4\beta_1$ integrin is involved in various developmental, physiological, and pathological processes.

$\alpha_4\beta_1$ integrin, also known as very late antigen-4 (VLA-4) or CD49d/CD29, is a leukocyte cell surface receptor that participates in a wide variety of both cell-cell and cell-matrix adhesive interactions (Hemler, *Ann. Rev. Immunol.,* 8:365 (1990)). $\alpha_4\beta_1$ integrin is implicated in metastasis (Holzmann et al., *Curr. Top. Microbio. Immunol.,* 231:125-141 (1998)), regulates leukocyte trafficking, and plays a critical role in inflammation and autoimmune diseases (Yusuf-Makagiansar et al., *Med. Res. Reviews,* 22:146-167 (2002)). For example, $\alpha_4\beta_1$ integrin promotes tumor cell dissemination in distal organs by strengthening their adhesion to the vascular endothelium and facilitating their extravasation (Holzmann et al., id; Hauzenberger et al., *Int. J. Cancer,* 72:1034-1044 (1997)). In chronic lymphocytic leukemia (CLL), $\alpha_4\beta_1$ integrin expression correlates with the presence of lymphadenopathy and determines the entry of the leukemia cells into nodes (Vincent et al., *Blood,* 87:4780-4788 (1996); Till et al., *Blood,* 15:2977-2984 (2002)).

Natural ligands for $\alpha_4\beta_1$ integrin include vascular cell adhesion molecule-1 (VCAM-1) and fibronectin (FN). $\alpha_4\beta_1$ integrin recognizes the primary amino acid sequence Gln-Ile-Asp-Ser (QIDS; SEQ ID NO:2) in VCAM-1 and Ile-Leu-Asp-Val (ILDV; SEQ ID NO:3) in FN. Blocking $\alpha_4\beta_1$ interaction with its ligands has been used as a therapeutic strategy for inflammation and autoimmune diseases. For example, monoclonal antibodies to $\alpha_4\beta_1$ integrin have been widely studied for their therapeutic effects. However, there are disadvantages using monoclonal antibody-based therapy due to factors such as low relative efficacy/safety ratios, especially in terms of systemic administration and immunogenic potential. To overcome these disadvantages, derivatives of the ILDV (SEQ ID NO:3) or QIDS (SEQ ID NO:2) sequence in the form of peptide, peptidomimetic, and small molecule non-peptide analogs are of particular interest (Helena et al., ibid).

By screening a random peptide library with an intact Jurkat T-leukemia cell line, the amino acid sequence Leu-Asp-Ile (LDI) was identified as a unique motif that binds preferentially to $\alpha_4\beta_1$ integrin receptors on human lymphoid malignant cells and not to normal human peripheral lymphocytes (Park et al., *Lett. Pept. Sci.,* 8:171-178 (2002)). The LDI peptide motif also binds preferentially to fresh leukemia cells isolated from patients with acute lymphocytic leukemia. As such, the activated form of $\alpha_4\beta_1$ integrin is an attractive therapeutic or imaging target for human lymphoid malignancies, e.g., non-Hodgkins lymphoma, acute lymphocytic leukemia, and chronic lymphocytic leukemia, or for other cancers that over-express $\alpha_4\beta_1$ integrin.

By using the ILDV (SEQ ID NO:3) sequence in FN as the starting point for inhibitor design, a series of $\alpha_4\beta_1$ integrin inhibitors were developed (Chen et al., *Biochem.,* 37:8743-8753 (1998)). One of the inhibitors, BIO-1211, was generated by substituting the Ile in ILDV with a 4-((N'-2-methylphenyl) ureido)-phenylacetyl N-terminal cap and adding a Pro (P) residue at the C-terminus. BIO-1211 is a potent $\alpha_4\beta_1$ integrin inhibitor and selectively binds to the activated form of the receptor (Lin et al., *J. Med. Chem.,* 42:920-934 (1999)). However, all of the $\alpha_4\beta_1$ integrin inhibitors to date, including BIO-1211, have been designed as specific therapy for inflammatory and autoimmune diseases, and not for cancer. Further, these $\alpha_4\beta_1$ integrin inhibitors suffer from the significant disadvantage of being susceptible to proteolysis by proteases found, for example, in plasma, the gastrointestinal tract, and tumor cells.

Thus, there is a need to develop $\alpha_4\beta_1$ integrin inhibitors that (1) bind to $\alpha_4\beta_1$ integrin with higher specificity and affinity than BIO-1211; (2) bind with high specificity and affinity to tumor cells (e.g., leukemia cells); and (3) are more resistant to cleavage or degradation from proteases found, for example, in plasma, the gastrointestinal tract, and tumor cells. The present invention satisfies this and other needs.

BRIEF SUMMARY OF THE INVENTION

The present invention provides novel $\alpha_4\beta_1$ integrin ligands (i.e., inhibitors) that advantageously display high binding affinity, specificity, and stability. These ligands are particularly useful for imaging a tumor, organ, or tissue and for treating cancer, inflammatory diseases, and autoimmune diseases. Kits containing these ligands for imaging or therapy are also provided.

As such, in one aspect, the present invention provides compounds having the formula:

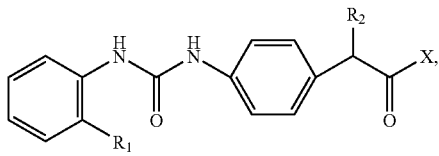

wherein
- $R_1$ is selected from the group consisting of —H, a $C_1$-$C_4$ alkyl group, a $C_1$-$C_4$ alkoxy group, a $C_1$-$C_4$ haloalkyl group, and a halogen;
- $R_2$ is selected from the group consisting of —H, a $C_1$-$C_4$ alkyl group, and a $C_3$-$C_8$ cycloalkyl group;
- X is a peptide having n independently selected amino acids, wherein at least one amino acid is selected from the group consisting of an unnatural amino acid and a D-amino acid; and
- n is an integer of from 3 to 20.

In one embodiment, X is a peptide having the following structure:

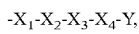

wherein
- $X_1$ is selected from the group consisting of a hydrophobic amino acid and derivatives of lysine, ornithine (Orn) and α,γ-diaminobutyric acid (Dbu);
- $X_2$ is a negatively charged amino acid;
- $X_3$ is a hydrophobic amino acid;
- $X_4$ is selected from the group consisting of a naturally-occurring amino acid, an unnatural amino acid, and a D-amino acid;
- Y is a peptide fragment having m independently selected amino acids; and
- m is an integer of from 0 to 20.

In another embodiment, X is a peptide having the following structure:

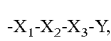

wherein
- $X_1$ is selected from the group consisting of a hydrophobic amino acid and a lysine derivative;
- $X_2$ is a negatively charged amino acid;
- $X_3$ is a hydrophobic amino acid;
- Y is a peptide fragment having m independently selected amino acids; and
- m is an integer of from 0 to 20.

In another aspect, the present invention provides a method for treating cancer in a subject in need thereof, the method comprising:
administering to the subject a therapeutically effective amount of a compound having the formula:

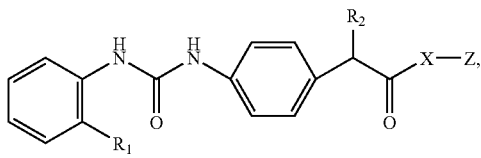

wherein
- $R_1$ is selected from the group consisting of —H, a $C_1$-$C_4$ alkyl group, a $C_1$-$C_4$ alkoxy group, a $C_1$-$C_4$ haloalkyl group, and a halogen;
- $R_2$ is selected from the group consisting of —H, a $C_1$-$C_4$ alkyl group, and a $C_3$-$C_8$ cycloalkyl group;
- X is a peptide having n independently selected amino acids, wherein at least one amino acid is selected from the group consisting of an unnatural amino acid and a D-amino acid;
- Z is a chelating agent with a radiometal, a chelating agent-linker conjugate with a radiometal, a radionuclide, biotin, a fluorophore, an antibody, horseradish peroxidase, alkaline phosphatase, nanoparticles, quantum dots, nanodroplets of detectable anticancer agents, liposomal drugs or a cytokine; and
- n is an integer of from 3 to 20;

wherein the effective amount is an amount sufficient for therapeutic benefit or an amount sufficient to target delivery of an anticancer agent selected from radionuclides, chemotherapeutic agents, nanoparticles, nanodroplets and cytokines.

In yet another aspect, the present invention provides a method for imaging a tumor, organ, or tissue, the method comprising:
(a) administering to a subject in need of such imaging, a compound having the formula:

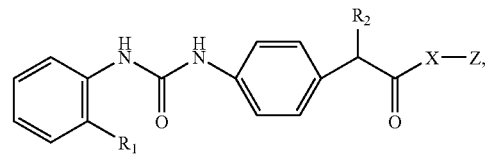

wherein
- $R_1$ is selected from the group consisting of —H, a $C_1$-$C_4$ alkyl group, a $C_1$-$C_4$ alkoxy group, a $C_1$-$C_4$ haloalkyl group, and a halogen;
- $R_2$ is selected from the group consisting of —H, a $C_1$—$C_4$ alkyl group, and a $C_3$-$C_8$ cycloalkyl group;
- X is a peptide having n independently selected amino acids, wherein at least one amino acid is selected from the group consisting of an unnatural amino acid and a D-amino acid;
- Z is an imaging moiety; and
- n is an integer of from 3 to 20; and
(b) detecting the compound to determine where the compound is concentrated in the subject.

In still yet another aspect, the present invention provides a method for treating an inflammatory or autoimmune disease in a subject in need thereof, the method comprising:
administering to the subject a therapeutically effective amount of a compound having the formula:

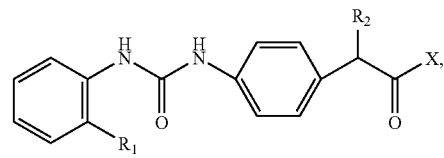

wherein
- $R_1$ is selected from the group consisting of —H, a $C_1$-$C_4$ alkyl group, a $C_1$-$C_4$ alkoxy group, a $C_1$-$C_4$ haloalkyl group, and a halogen;
- $R_2$ is selected from the group consisting of —H, a $C_1$-$C_4$ alkyl group, and a $C_3$-$C_8$ cycloalkyl group;
- X is a peptide having n independently selected amino acids, wherein at least one amino acid is selected from the group consisting of an unnatural amino acid and a D-amino acid; and
- n is an integer of from 3 to 20.

In a further aspect, the present invention provides kits for imaging a tumor, organ, or tissue or for treating cancer, an inflammatory disease, or an autoimmune disease comprising one or more of the above-described compounds and directions for use in imaging or therapy.

Other objects, features, and advantages of the present invention will be apparent to one of skill in the art from the following detailed description and figures.

DETAILED DESCRIPTION OF THE INVENTION

I. Definitions

Figure 1:
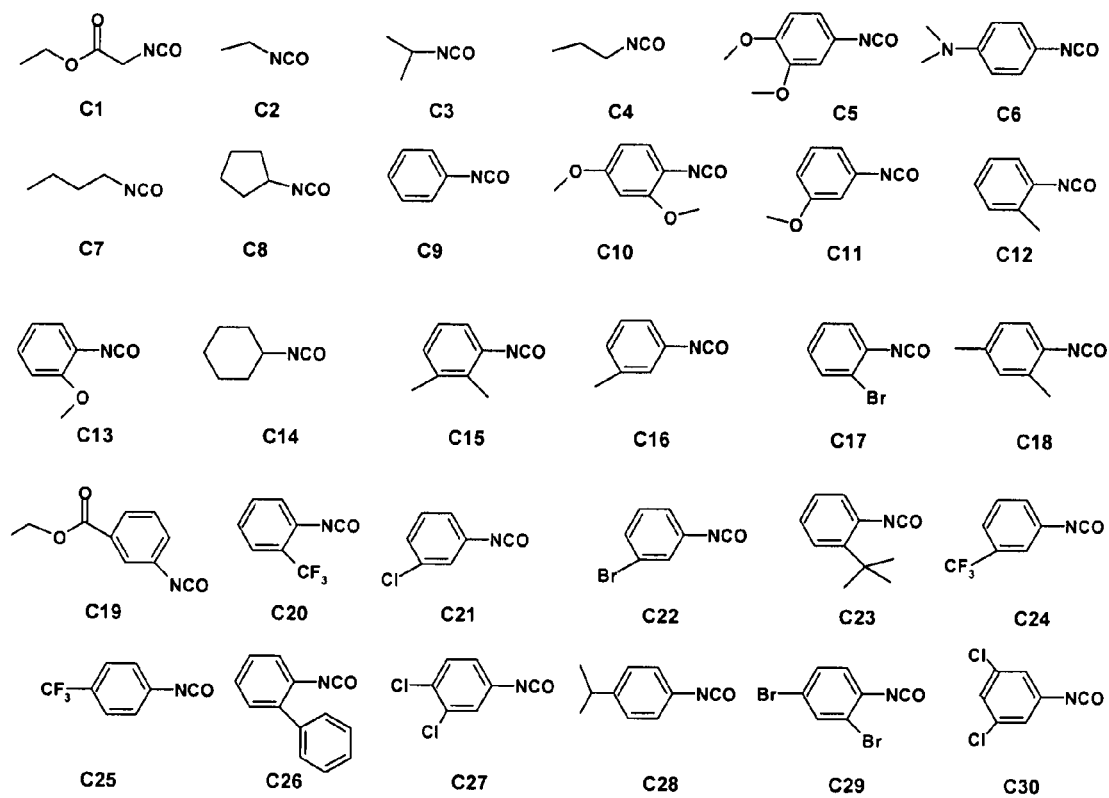
FIG. 1 shows the thirty isocyanantes used in the synthesis of position A in the ligands of the present invention.

As used herein, the following terms have the meanings ascribed to them unless specified otherwise.

The term "amino acid" refers to naturally-occurring $\alpha$-amino acids and their stereoisomers, as well as unnatural amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., γ-carboxyglutamate and O-phosphoserine. Naturally-occurring $\alpha$-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring $\alpha$-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an ae carbon that is bound to a hydrogen, a carboxyl group, an amino group, but have modified R (i.e., side-chain) groups. Suitable unnatural amino acids include, without limitation, 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine (Tyr(3,5-di NO$_2$)), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo [3,2-α]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 1-amino-1-(3-piperidinyl)carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz(2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, derivatives of lysine, ornithine (Orn) and α,γ-diaminobutyric acid (Dbu), stereoisomers thereof, and combinations thereof (see, Liu and Lam, *Anal. Biochem.,* 295:9-16 (2001)). As such, the unnatural α-amino acids are present either as unnatural L-α-amino acids, unnatural D-α-amino acids, or combinations thereof.

Suitable phenylalanine analogs include, without limitation, homophenylalanine (HoPhe), phenylglycine (Phg), 3,3-diphenylalanine (Dpa), 4-aminophenylalanine (Phe(4-NH$_2$)), 2-methylphenylalanine (Phe(2-Me)), 3-methylphenylalanine (Phe(3-Me)), 4-methylphenylalanine (Phe(4-Me)), 4-azidophenylalanine (Phe(4-N$_3$)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF$_3$)), 3-trifluoromethylphenylalanine (Phe(3-CF$_3$)), 4-trifluoromethylphenylalanine (Phe(4-CF$_3$)), 2-methoxyphenylalanine (Phe(2-OMe)), 3-methoxyphenylalanine (Phe(3-OMe)), 2-nitrophenylalanine (Phe(2-NO$_2$)), 3-nitrophenylalanine (Phe(3-NO$_2$)), 4-nitrophenylalanine (Phe(4-NO$_2$)), 2-cyanophenylalanine (Phe(2-CN)), 3-cyanophenylalanine (Phe(3-CN)), 4-cyanophenylalanine (Phe(4-CN)), 3,4-dimethoxyphenylalanine (Phe(3,4-di OMe)), 3,4-difluorophenylalanine (Phe(3,4-di F)), 3,5-difluorophenylalanine (Phe(3,5-di F)), 2,4-dichlorophenylalanine (Phe(2,4-di Cl)), 3,4-dichlorophenylalanine (Phe(3,4-di Cl)), 4-benzoylphenylalanine (Bpa), 4-carboxyphenylalanine (Phe(4-COOH)), 4,4'-biphenylalanine (Bip), 2,3,4,5,6-pentafluorophenylalanine (Phe(F$_5$)), 3,4,5-trifluorophenylalanine (Phe(F$_3$)), 4-chlorophenylglycine (Phg(4-Cl)), 2-chlorophenylglycine (Phg(2-Cl)), 3-chlorophenylglycine (Phg(3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr(Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

Suitable derivatives of lysine (Lys), ornithine (Orn) and Dbu, include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof. See, Table 5 for a description of the structures for each of the lysine derivatives. Derivatives of Orn and Dbu are similar to the lysine derivatives with corresponding carboxylic acid attached to the side chain of Orn and Dbu, respectively.

Suitable N-methyl amino acids include N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-NO$_2$), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-NH$_2$), N-methyl-4-Phe(4-Me), N-methyl-Phe(4-F), N-methyl-Phe(4-Cl), N-methyl-Phe(2-Br), N-methyl-Phe(3-Br), N-methyl-Phe(4-Br), N-methyl-Phe(3-CF$_3$), N-methyl-Phe(4-CF$_3$), N-methyl-Phe (4-NO$_2$), N-methyl-Phe(4-CN), N-methyl-Bpa, N-methyl-Phg(4-Cl), N-methyl-Phg(4-Br), N-methyl-Tyr(Me), N-methyl-Lys38, N-methyl-Lys27, N-methyl-Lys73, N-methyl-Lys55, N-methyl-Lys28, N-methyl-Lys72, N-methyl-Lys 12, N-methyl-Lys 123, N-methyl-Lys63, N-methyl-Lys 124, N-methyl-Lys82, N-methyl-Lys31, N-methyl-Lys 15, N-methyl-Lys 125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

"Amino acid mimetics" are chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

"N-substituted glycines" are unnatural amino acids based on glycine, where an amino acid side-chain is attached to the glycine nitrogen atom. Suitable amino acid side-chains (e.g., R groups) include, but are not limited to, side chains present in naturally-occurring amino acids and side-chains present in unnatural amino acids such as amino acid analogs. Examples of N-substituted glycines suitable for use in the present invention include, without limitation, N-(2-aminoethyl)glycine, N-(3-aminopropyl)glycine, N-(2-methoxyethyl)glycine, N-benzylglycine, (S)-N-(1-phenylethyl)glycine, N-cyclohexylmethylglycine, N-(2-phenylethyl)glycine, N-(3-phenylpropyl)glycine, N-(6-aminogalactosyl)glycine, N-(2-(3'-indolylethyl)glycine, N-(2-(p-methoxyphenylethyl))glycine, N-(2-(p-chlorophenylethyl)glycine, and N-[2-(p-hydroxyphenylethyl)]glycine. N-substituted glycine oligomers, referred to herein as "peptoids," have been shown to be protease resistant (Miller et al., Drug Dev. Res., 35:20-32 (1995)). As such, peptoids containing at least one unnatural α-amino acid, D-amino acid, or a combination thereof are within the scope of the present invention.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, 1984).

The term "peptide" refers to a compound made up of a single chain of D- or L-amino acids or a mixture of D- and L-amino acids joined by peptide bonds. Generally, peptides are about 2 to about 50 amino acids in length. Preferably, the peptides of the present invention are about 2 to about 25 amino acids in length, more preferably 3 to 20 amino acids in length, and most preferably 3 to 7 amino acids in length.

The term "cancer" refers to any of various malignant neoplasms characterized by the proliferation of anaplastic cells that tend to invade surrounding tissue and metastasize to new body sites. Examples of different types of cancer suitable for treatment using the present invention include, but are not limited to, ovarian cancer, breast cancer, lung cancer, bladder cancer, thyroid cancer, liver cancer, pleural cancer, pancreatic cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers, osteogenic sarcomas, fibrosarcoma, neuroblastoma, glioma, melanoma, leukemia, and lymphoma.

The term "leukemia" refers to a malignant disease, i.e., cancer, of the bone marrow and blood characterized by the uncontrolled accumulation of blood cells. Leukemia is divided into myelogenous or lymphocytic leukemia, each of which can be acute or chronic. The terms myelogenous or lymphocytic denote the cell type involved. Examples of the types of leukemia suitable for treatment using the present invention include, but are not limited to, acute lymphocytic leukemia, chronic lymphocytic leukemia, acute myelogenous leukemia, chronic myelogenous leukemia, and hairy cell leukemia.

The term "lymphoma" refers to a group of cancers that originates in the lymphatic system. Lymphoma results when a lymphocyte (i.e., a type of white blood cell) undergoes a malignant change and begins to multiply, eventually crowding out healthy cells and creating tumors which enlarge the lymph nodes or other sites in the body. Examples of the types of lymphoma suitable for treatment using the present invention include, but are not limited to, non-Hodgkin's lymphoma, Hodgkin's lymphoma, B-cell lymphoma, acute lymphocytic leukemia, chronic lymphocytic leukemia, T-cell lymphoma, multiple myeloma, hairy cell leukemia, other cancers expressing $\alpha_4\beta_1$-integrin and Burkitt's lymphoma.

The term "inflammatory disease" refers to a disease or disorder characterized or caused by inflammation. "Inflammation" refers to a local response to cellular injury that is marked by capillary dilatation, leukocytic infiltration, redness, heat, and pain that serves as a mechanism initiating the elimination of noxious agents and of damaged tissue. The site of inflammation includes the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Such inflammatory diseases include, but are not limited to, inflammatory bowel disease (IBD), rheumatoid diseases such as rheumatoid arthritis, fibrositis, pelvic inflammatory disease, acne, psoriasis, actinomycosis, dysentery, biliary cirrhosis, asthma, Lyme disease, heat rash, Stevens-Johnson syndrome, mumps, pemphigus vulgaris, and blastomycosis.

The term "autoimmune disease" refers to a disease or disorder resulting from an immune response against a self tissue or tissue component and includes a self antibody response or cell-mediated response. The term autoimmune disease, as used herein, encompasses organ-specific autoimmune diseases, in which an autoimmune response is directed against a single tissue, such as Type I diabetes mellitus, myasthenia gravis, vitiligo, Graves' disease, Hashimoto's disease, Addison's disease, autoimmune gastritis, and autoimmune hepatitis. The term autoimmune disease also encompasses non-organ specific autoimmune diseases, in which an autoimmune response is directed against a component present in several or many organs throughout the body. Such autoimmune diseases include, for example, systemic lupus erythematosus, progressive systemic sclerosis and variants, polymyositis, and dermatomyositis. Additional autoimmune diseases include, but are not limited to, pernicious anemia, primary biliary cirrhosis, autoimmune thrombocytopenia, Sjogren's syndrome, and multiple sclerosis.

The term "therapeutically effective amount" refers to the amount of a compound of the present invention that is capable of achieving a therapeutic effect in a subject in need thereof. For example, a therapeutically effective amount of a compound of the present invention can be the amount that is capable of preventing or relieving one or more symptoms associated with cancer or an inflammatory or autoimmune disease. One skilled in the art will appreciate that the compounds of the present invention can be co-administered with other therapeutic agents (e.g., ions, small organic molecules, peptides, proteins, polypeptides, oligosaccharides, etc.) such as anti-cancer, anti-inflammatory, or immunosuppressive agents.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a compound of the present invention for preventing or relieving one or more symptoms associated with cancer or an inflammatory or autoimmune disease. By "co-administer" it is meant that a compound of the present invention is administered at the same time, just prior to, or just after the administration of a second drug (e.g., anti-cancer agent, anti-inflammatory agent, immunosuppressive agent, etc.).

The term "imaging moiety" refers to a label that is attached to the compounds of the present invention for imaging a tumor, organ, or tissue in a subject. The imaging moiety can be covalently or non-covalently attached to the compound. Examples of imaging moieties suitable for use in the present invention include, without limitation, radionuclides, biotin, fluorophores such as fluorescein, rhodamine, Texas Red, Cy2, Cy3, or Cy5, antibodies, horseradish peroxidase, alkaline phosphatase, derivatives thereof, and mixtures thereof. Exemplary methods for synthesizing the compounds of the present invention as a biotin conjugate or as a DOTA conjugate are provided in Examples 12 and 13, respectively. One skilled in the art will know of other suitable methods for conjugating a particular imaging moiety to the compounds of the present invention.

The term "chelating agent" refers to a compound which binds to a metal ion, such as a radionuclide, with considerable affinity and stability. In addition, the chelating agents of the present invention are bifunctional, having a metal ion chelating group at one end and a reactive functional group capable of binding to peptides, polypeptides, or proteins at the other end. Suitable bifunctional chelating agents include, but are not limited to, 1,4,7,10-tetraazacyclododecane-N,N',N",N'''-tetraacetic acid (DOTA), a bromoacetamidobenzyl derivative of DOTA (BAD), 1,4,8,11-tetraazacyclotetradecane-N,N',N",N'''-tetraacetic acid (TETA), diethylenetriaminepentaacetic acid (DTPA), the dicyclic dianhydride of diethylenetriaminepentaacetic acid (ca-DTPA), 2-(p-isothiocyanatobenzyl)-diethylenetriaminepentaacetic acid (SCNBzDTPA), and 2-(p-isothiocyanatobenzyl)-5(6)-methyl-diethylenetriaminepentaacetic acid (M×DTPA) (see, Ruegg et al., *Cancer Research*, Vol. 50: 14 4221-4226, 1990; DeNardo et al., *Clinical Cancer Research, Vol.* 4: 10 2483-2490, 1998). Other chelating agents include EDTA, NTA, HDTA and their phosphonate analogs such as EDTP, HDTP, NTP (see, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989; and references contained therein).

The term "radionuclide" refers to a nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Radionuclides suitable for use in the present invention include, but are not limited to, fluorine 18 ($^{18}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$), silver 111 ($^{111}Ag$), indium 111 ($^{111}In$), iodine 124 ($^{124}I$), iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 ($^{166}Ho$), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth 212 ($^{212}Bi$). As used herein, the "m" in $^{117m}Sn$ and $^{99m}Tc$ stands for meta state. Additionally, naturally occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{117m}Sn$, $^{149}Pm$, $^{153}Sm$, $^{166}Ho$, and $^{188}Re$ are examples of beta-emitting radionuclides. $^{67}Ga$, $^{111}In$, $^{99m}Tc$, and $^{201}Tl$ are examples of gamma-emitting radionuclides. $^{55}Co$, $^{60}Cu$, $^{61}Cu$, $^{62}Cu$, $^{66}Ga$, $^{68}Ga$, $^{82}Rb$, and $^{86}Y$ are examples of positron-emitting radionuclides. $^{64}Cu$ is a beta- and positron-emitting radionuclide.

The term "linker" refers to a moiety that possesses one or more different reactive functional groups that allows for covalent attachment of moieties such as a peptide to a chelating agent. Preferably, the linking moiety possesses two different reactive functional groups, i.e., a heterobifunctional linker. Suitable linkers include, without limitation, those available from Pierce Biotechnology, Inc. (Rockford, Ill.). In preferred embodiments of the present invention, the linker provides a carboxyl group for the attachment of a chelating agent and an amino group for the attachment of a peptide. However, one skilled in the art understands that any reactive functional group can be present on the linker, as long as it is compatible with a functional group on the moiety that is to be covalently attached. As used herein, the term "chelating agent-linker conjugate" refers to a chelating agent covalently attached to a linker. Such chelating agent-linker conjugates can be attached to a peptide via a functional group present on the linker.

II. General Overview

The present invention provides novel $\alpha_4\beta_1$ integrin ligands (i.e., inhibitors) that advantageously display high binding affinity, specificity, and stability, and methods of their use for imaging a tumor, organ, or tissue in a subject and for treating cancer, inflammatory diseases, and autoimmune diseases.

Before the advent of the present invention, all $\alpha_4\beta_1$ integrin ligands, including BIO-1211, were designed as specific therapy for inflammatory and autoimmune diseases, and not for cancer. Furthermore, these ligands suffered from the significant disadvantage of being susceptible to proteolysis by proteases found, for example, in plasma, the gastrointestinal tract, and tumor cells. As such, there was a need for protease-resistant $\alpha_4\beta_1$ integrin ligands with high affinity and specificity for use not only in treating cancer, but also in imaging a tumor, organ, or tissue and treating inflammatory and autoimmune diseases.

The present invention is based on the surprising discovery that $\alpha_4\beta_1$ integrin ligands containing a combination of naturally-occurring amino acids, unnatural amino acids, and D-amino acids with a 4-((N'-2-methylphenyl)ureido)-phenylacetyl group attached via a peptide bond at the amino-terminus have the following advantageous properties: (1) the ligands bind to $\alpha_4\beta_1$ integrin with higher specificity and affinity than BIO-1211; (2) the ligands bind with high specificity and affinity to tumor cells (e.g., leukemia cells); and (3) the ligands are more resistant to cleavage and/or degradation from proteases found, for example, in plasma, the gastrointestinal tract, and tumor cells. These unique features make the ligands of the present invention particularly useful as imaging agents for localizing tumors and as therapeutic agents for the treatment of cancer (e.g., lymphocytic leukemia, lymphoma and multiple myeloma) as well as other diseases and disorders such as inflammatory diseases, autoimmune diseases, etc.

III. Description of the Embodiments

In one aspect, the present invention provides compounds having the formula:

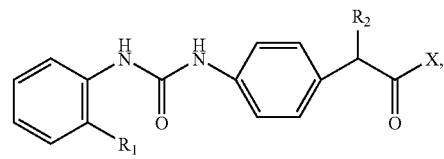

wherein
$R_1$ is selected from the group consisting of —H, a $C_1$-$C_4$ alkyl group, a $C_1$-$C_4$ alkoxy group, a $C_1$-$C_4$ haloalkyl group, and a halogen;
$R_2$ is selected from the group consisting of —H, a $C_1$-$C_4$ alkyl group, and a $C_3$-$C_8$ cycloalkyl group;
X is a peptide having n independently selected amino acids, wherein at least one amino acid is selected from the group consisting of an unnatural amino acid and a D-amino acid; and
n is an integer of from 3 to 20.

In a first embodiment, $R_1$ is —$CH_3$. In a second embodiment, $R_2$ is —H. In a third embodiment, the halogen is selected from the group consisting of -F, —Cl, —Br, and —I. In a fourth embodiment, the $C_3$-$C_8$ cycloalkyl group is selected from the group consisting of a cyclopropyl group, a cyclopentyl group, and a cyclohexyl group. In a fifth embodiment, the $C_1$-$C_4$ haloalkyl group is —$CF_3$. In a sixth embodiment, the $C_1$-$C_4$ alkoxy group is a methoxy group. In certain instances, the compounds of the present invention further comprise a radionuclide, a chelating agent, biotin, a fluorophore, an antibody, horseradish peroxidase, or alkaline phosphatase attached thereto. Such conjugates can be particularly useful, e.g., for therapeutic and/or imaging purposes.

In another embodiment, the amino acids are selected from the group consisting of naturally-occurring amino acids; unnatural amino acids such as amino acid analogs, amino acid mimetics, synthetic amino acids, N-substituted glycines, N-methyl amino acids; stereoisomers thereof; and combinations thereof.

In yet another embodiment, the unnatural amino acid is selected from the group consisting of 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine (Tyr(3,5-di NO₂)), norleucine (Nle), 3-(2-naphthyl)alanine (NaI-2), 3-(1-naphthyl)alanine (NaI-1), cyclohexylalanine (Cha), di-n-propylglycine (Dpg), cyclopropylalanine (Cpa), homoleucine (Hle), homoserine (HoSer), homoarginine (Har), homocysteine (Hcy), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp (Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo [3,2-α]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO₂)), 1-amino-1-cyclohexane carboxylic acid (Ach), 1-amino-1-(3-piperidinyl)carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz (2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, derivatives of lysine, ornithine (Orn) and α,γ-diaminobutyric acid (Dbu), stereoisomers thereof, and combinations thereof.

Suitable phenylalanine analogs include, without limitation, homophenylalanine (HoPhe), phenylglycine (Phg), 3,3-diphenylalanine (Dpa), 4-aminophenylalanine (Phe(4-NH₂)), 2-methylphenylalanine (Phe(2-Me)), 3-methylphenylalanine (Phe(3-Me)), 4-methylphenylalanine (Phe(4-Me)), 4-azidophenylalanine (Phe(4-N₃)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF₃)), 3-trifluoromethylphenylalanine (Phe(3-CF₃)), 4-trifluoromethylphenylalanine (Phe(4-CF₃)), 2-methoxyphenylalanine (Phe(2-OMe)), 3-methoxyphenylalanine (Phe(3-OMe)), 2-nitrophenylalanine (Phe(2-NO₂)), 3-nitrophenylalanine (Phe(3-NO₂)), 4-nitrophenylalanine (Phe(4-NO₂)), 2-cyanophenylalanine (Phe(2-CN)), 3-cyanophenylalanine (Phe (3-CN)), 4-cyanophenylalanine (Phe(4-CN)), 3,4-dimethoxyphenylalanine (Phe(3,4-di OMe)), 3,4-difluorophenylalanine (Phe(3,4-di F)), 3,5-difluorophenylalanine (Phe(3,5-di F)), 2,4-dichlorophenylalanine (Phe(2,4-di Cl)), 3,4-dichlorophenylalanine (Phe(3,4-di Cl)), 4-benzoylphenylalanine (Bpa), 4-carboxyphenylalanine (Phe(4-COOH)), 4,4'-biphenylalanine (Bip), 2,3,4,5,6-pentafluorophenylalanine (Phe(F₅)), 3,4,5-trifluorophenylalanine (Phe(F₃)), 4-chlorophenylglycine (Phg(4-Cl)), 2-chlorophenylglycine (Phg(2-Cl)), 3-chlorophenylglycine (Phg(3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr (Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

Suitable derivatives of lysine (Lys), Orn and Dbu include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof.

Suitable N-methyl amino acids include, N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-NaI-2, N-methyl-NaI-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-NO₂), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-NH₂), N-methyl-4-Phe(4-Me), N-methyl-Phe(4-F), N-methyl-Phe(4-Cl), N-methyl-Phe(2-Br), N-methyl-Phe(3-Br), N-methyl-Phe(4-Br), N-methyl-Phe(3-CF₃), N-methyl-Phe(4-CF₃), N-methyl-Phe (4-NO₂), N-methyl-Phe(4-CN), N-methyl-Bpa, N-methyl-Phg(4-Cl), N-methyl-Phg(4-Br), N-methyl-Tyr(Me), N-methyl-Lys38, N-methyl-Lys27, N-methyl-Lys73, N-methyl-Lys55, N-methyl-Lys28, N-methyl-Lys72, N-methyl-Lys 12, N-methyl-Lys 123, N-methyl-Lys63, N-methyl-Lys 124, N-methyl-Lys82, N-methyl-Lys31, N-methyl-Lys 15, N-methyl-Lys 125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu 15, N-methyl-Dbu 125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

In another embodiment, the D-amino acid is selected from the group consisting of a D-α-amino acid, a D-β-amino acid, a D-γ-amino acid, and a combination thereof. In yet another embodiment, the D-α-amino acid is selected from the group consisting of a stereoisomer of a naturally-occurring α-amino acid, an unnatural D-α-amino acid, and a combination thereof. In still yet another embodiment, the stereoisomer of a naturally-occurring α-amino acid is selected from the group consisting of D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof. In a further embodiment, n is an integer of from 3 to 15, preferably of from 3 to 10, and more preferably of from 3 to 7.

In certain instances, X is a peptide having the following structure:

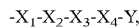

-$X_1$-$X_2$-$X_3$-$X_4$-Y, wherein
  $X_1$ is selected from the group consisting of a hydrophobic amino acid and derivatives of lysine, ornithine (Orn) and α,γ-diaminobutyric acid (Dbu);
  $X_2$ is a negatively charged amino acid;
  $X_3$ is a hydrophobic amino acid;
  $X_4$ is selected from the group consisting of a naturally-occurring amino acid, an unnatural amino acid, and a D-amino acid;
  Y is a peptide fragment having m independently selected amino acids; and
  m is an integer of from 0 to 20.

In one embodiment, m is an integer of from 0 to 15, preferably of from 0 to 10, more preferably of from 0 to 5, and still more preferably of from 0 to 3. In another embodiment, Y has a carboxyl-terminal group selected from the group consisting of an amide group and a carboxylic acid group.

In yet another embodiment, the hydrophobic amino acid is independently selected from the group consisting of leucine (Leu), a leucine analog, phenylalanine (Phe), a phenylalanine analog, proline (Pro), a proline analog, valine (Val), isoleucine (Ile), glycine (Gly), alanine (Ala), norvaline (Nva), 1-aminocyclopropane-1-carboxylic acid (Acpc), 1-aminocyclobutane-1-carboxylic acid (Acb), α-cyclohexylglycine (Chg), α-aminoisobutyric acid (Aib), α-aminobutyric acid (Abu), 3-(2-thienyl)alanine (2-Thi), 3-(3-thienyl)alanine (3-Thi), 3-(3-pyridyl)alanine (3-Pal), 3-(2-naphthyl)alanine (NaI-2), 2-amino-2-naphthylacetic acid (Ana), 3,5-dinitrotyrosine (Tyr(3,5-di NO$_2$)), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 2-aminoindane-2-carboxylic acid (Aic), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), and a stereoisomer thereof.

Suitable leucine analogs include, without limitation, norleucine (Nle), homoleucine (Hle), propargylglycine (Pra), cyclopropylalanine (Cpa), cylobutylalanine (Cba), cyclopentylalanine, cyclohexylalanine (Cha), and a stereoisomer thereof. Suitable phenylalanine analogs include any of the phenylalanine analogs described above. Suitable proline analogs include, without limitation, hydroxyproline (Hyp), O-benzyl-hydroxyproline (Hyp(Bzl)), homoproline (HoPro), (3-homoproline (βHoPro), thiazolidine-4-carboxylic acid (Thz), 1-aminocyclopentane-1-carboxylic acid (Acp), (2S, 5R)-5-phenylpyrrolidine-2-carboxylic acid (Ppca), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 3-aminobenzoic acid (3-Abz), 5H-thiazolo [3,2-a]pyridine-3-carboxylic acid (Btd), and a stereoisomer thereof.

In another embodiment, the lysine derivative includes any of the lysine derivatives described above. In yet another embodiment, the negatively charged amino acid is selected from the group consisting of aspartic acid (Asp), glutamic acid (Glu), α-aminohexanedioic acid (Aad), α-aminooctanedioc acid (Asu), homoaspartic acid (HoAsp), γ-carboxyglutamic acid, 4-carboxyphenylalanine (Phe(4-COOH)), and a stereoisomer thereof.

In one embodiment, $X_1$ is selected from the group consisting of Leu, a leucine analog, Lys38, and a stereoisomer thereof. In another embodiment, $X_2$ is selected from the group consisting of Asp, Glu, Aad, and a stereoisomer thereof. In a preferred embodiment, $X_2$ is Aad. In yet another embodiment, $X_3$ is selected from the group consisting of Leu, a Leu analog, Phe, a Phe analog, Val, Ile, Ala, Nva, Acpc, Chg, Aib, Abu, Aic, NaI-2, Ana, and a stereoisomer thereof. In still yet another embodiment, $X_4$ is selected from the group consisting of a hydrophobic amino acid, a negatively charged amino acid, and a stereoisomer thereof. Preferably, the hydrophobic amino acid is selected from the group consisting of Pro, a Pro analog, and a stereoisomer thereof. Preferably, the Pro analog is Hyp.

In a preferred embodiment, X is selected from the group consisting of -Nle-Aad-Chg-D-Tyr, -Leu-Aad-Chg-D-Gln-D-Tyr, -Cpa-Asp-Phg-D-Glu-D-Ser, -Leu-Aad-Val-Hyp, -Nle-Aad-Val-D-Thr-Hyp-D-Asn, -Cha-Aad-Nle-D-Gln-D-Asn, -Cpa-Glu-Val-D-Asp-D-Ala, -Hle-Aad-Phe-Chg, -Nle-Asp-Pra-Gly-Hyp, -Lys38-Aad-Leu-D-Pro, -Cha-Asp-Val-D-Glu-D-Gln, -Cpa-Aad-Ile-D-Asp, -Hle-Aad-Aib-D-3-Pal, -Lys38-Glu-Acpc-Nle-D-Asp-D-Gln, -Nle-Asp-Val-Ach-D-Ala, -Leu-Aad-Ala-Hyp, -Cpa-Asp-Nva-D-Glu, -Leu-Aad-Nva-Hyp-D-Glu, -Hle-Asp-Ile-D-Asp-HoSer-D-Asn, -Cpa-Aad-Aib-D-Thi, -Cpa-Aad-Acpc-Hyp, -Cpa-Aad-Val-D-Tyr-D-Asp, -Nle-Asp-Ala-Aad-Aic, -Cha-Asp-HoPhe-Hyp-D-3-Pal-Nle-Ach, -Nle-Aad-Chg-Hyp-Aad, -Nle-Aad-Chg-Hyp-D-Val-D-Asp-D-Asp, -Cpa-Aad-Chg-Pro-Aad-Phe(3-Cl)-Aad, -Cpa-Aad-Chg-Acp-D-Asp-D-Glu, -Nle-Aad-Chg-Hyp-D-Glu-Ach, -Hle-Aad-Val-Hyp-Chg, -Nle-Glu-Phg-Acp-Aad, -Nle-Aad-Val-D-Glu, -Lys38-Aad-Acpc-D-Asp, -Lys38-Aad-Acpc-D-Asn-D-Asn, -Lys38-Aad-D-Phe-D-3-Pal, -Nle-Aad-Cha-D-Glu, -Hle-Aad-Ile-D-Asp-Nle, -Lys38-Aad-Aic-D-Glu-D-Tyr, -Cpa-Aad-Nle-D-Pro, -Lys-Aad-Chg-D-Glu, -Cpa-Aad-Chg-D-Ser-Gly, -Cpa-Aad-Nle-Aad, -Cpa-Aad-Acpc-Aad, -Leu-Aad-Acpc-Aad, -Nle-Aad-Nle-Chg-D-Glu, -HoPhe-Aad-D-NaI-2-D-Glu, -Lys38-Aad-D-Phe-4-Pal-D-Asn, -Lys38-Aad-D-Phe-D-Asp, -Lys38-Aad-D-Phe-D-Ser-Nva, and -Lys38-Aad-D-Phe-D-Val.

In another embodiment, the compounds bind to malignant B-cells, malignant T-cells or multiple myeloma cells. In some preferred embodiments, the compounds bind to acute lymphocytic leukemia cells. In a preferred embodiment, X is selected from the group consisting of -HoPhe-Asp-Phg-Pro-Gly-D-Tyr-Aad, -Hle-Asp-Ile-Pro-Chg, -Cpa-Asp-Ile-Hyp-D-Thr-D-Asn-Nva, -Cha-Asp-Pra-Pro-D-Pro-Gly-D-Ser, -Cha-Asp-Leu-Hyp-HoCit-HoCit, -Lys 12-Aad-Nva-Hyp-Hyp, -Hle-Asp-Val-Pro-D-3-Pal-Nva-Ana, -Cpa-Asp-Abu-Acp-Nva-D-Asp, -Cha-Asp-Tyr-Pro-D-His, -Leu-Aad-Abu-Ppca-Ach-D-Tyr, -Leu-Asp-Nva-Hyp-Gly-D-Phe-Nva, -Nle-Asp-Ile-Pro-Aib-D-HoPhe-Tyr(Me), -Cpa-Glu-Tyr-Pro-Chg-Aad-D-Glu, -Hle-Asp-Nva-Pro-D-Glu, -Nle-Asp-Ile-Hyp-Hyp, -Ile-Aad-Ile-Ppca-D-Ile, -HoPhe-Asp-Ala-Pro-Aib-D-Ala, -Hle-Glu-Abu-Hyp-HoCit-HoCit, -Leu-Asp-Leu-Ppca-HoCit-D-Thr-D-Pro, -HoPhe-Asp-Nva-Ppca-D-Ala, -Nle-Asp-Val-Pro-HoCit-Gly (SEQ ID NO :4), -Cpa-Aad-Abu-Pro-D-Ala-D-Tyr-D-Phe(4-Me), -Nle-Glu-Ala-D-Thi, -Cha-Asp-Nle-D-Gln, -Hle-Aad-Ile-D-Asp-D-Phe, -Leu-Asp-D-Phe-Aic, -Cpa-Asp-Leu-D-Thi, -HoPhe-Asp-Abu-D-Asn, -Cha-Aad-Val-Ana-Ahch, -Hle-Asp-Acpc-D-Ala, -Leu-Aad-Ana-D-Pro, -Lys38-Asp-Phe(3-Cl)-D-Pro, -Lys 12-Asp-Nle-Hyp-D-Glu, -Lys38-Aad-D-NaI-2-D-Thr-D-Bpa, -Cpa-Asp-Ala-D-Thi, and -HoPhe-Asp-Ala-Hyp. In yet another embodiment, the compound does not bind to non-leukemia cells.

In certain other instances, X is a peptide having the following structure:

-$X_1$-$X_2$-$X_3$-Y, wherein
$X_1$ is selected from the group consisting of a hydrophobic amino acid and derivatives of lysine, ornithine (Orn) and α,γ-diaminobutyric acid (Dbu);
$X_2$ is a negatively charged amino acid;
$X_3$ is a hydrophobic amino acid;
Y is a peptide fragment having m independently selected amino acids; and
m is an integer of from 0 to 20.

In one embodiment, m is an integer of from 0 to 15, preferably of from 0 to 10, more preferably of from 0 to 5, and still more preferably 0. In another embodiment, Y has a carboxyl-terminal group selected from the group consisting of an amide group and a carboxylic acid group.

The hydrophobic amino acid includes any of the hydrophobic amino acids described above. Likewise, the lysine derivative includes any of the lysine derivatives described above. Preferably, $X_1$ is Lys-38. The negatively charged amino acid includes any of the negatively charged amino acids described above. Preferably, $X_2$ is Aad. In certain instances, $X_3$ is a D-amino acid. In a preferred embodiment, X is selected from the group consisting of -Lys38-Aad-D-Phe, -Lys38-Aad-Ach, -Lys38-Aad-D-NaI-2, -Lys38-Aad-Ile, -Lys38-Aad-Val, and -Lys38-Aad-Leu. In a particularly preferred embodiment, X is -Lys38-Aad-Ach.

In another embodiment, the compounds bind to malignant B-cells, malignant T-cells or multiple myeloma cells. In some preferred embodiments, the compounds bind to acute lymphocytic leukemia cells. In a preferred embodiment, X is -Nle-Aad-Phg. In yet another embodiment, the compound does not bind to non-leukemia cells.

In a particularly preferred embodiment, the compound has the formula:

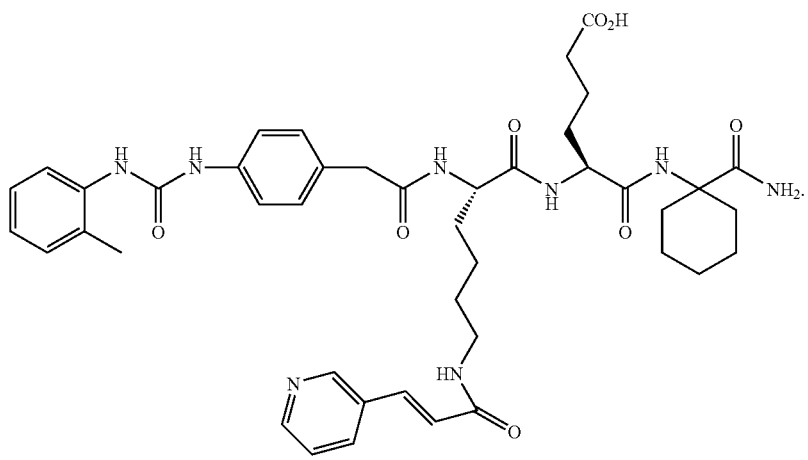

In a related aspect, the present invention provides multimers or oligomers of the compounds provided herein. In particular, mulitmers or oligomers are provided in which a plurality of the compounds (e.g., the ligands) are attached to a scaffolding such as a polyethylene glycol scaffolding to provide higher molecular weight conjugates. One of skill in the art will appreciate that a number of scaffolds are commercially available and can be used to confer various properties such as water solubility, and provide, in some embodiments, varying degrees of compound removal from the scaffold. In the latter instance, different linkages to the scaffold can alter the rates by which hydrolytic enzymes release the compound or degrade the scaffold.

In another aspect, the present invention provides a method for treating cancer in a subject in need thereof, the method comprising:
administering to the subject a therapeutically effective amount of a compound having the formula:

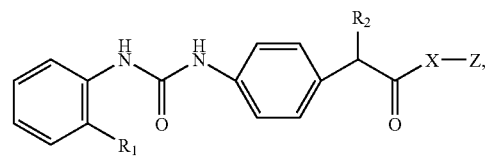

wherein
$R_1$ is selected from the group consisting of —H, a $C_1$-$C_4$ alkyl group, a $C_1$-$C_4$ alkoxy group, a $C_1$-$C_4$ haloalkyl group, and a halogen;
$R_2$ is selected from the group consisting of —H, a $C_1$-$C_4$ alkyl group, and a $C_3$-$C_8$ cycloalkyl group;

X is a peptide having n independently selected amino acids, wherein at least one amino acid is selected from the group consisting of an unnatural amino acid and a D-amino acid;

Z is a chelating agent or a chelating agent-linker conjugate; and n is an integer of from 3 to 20;

wherein the effective amount is an amount sufficient for therapeutic benefit or an amount sufficient to target delivery of an anticancer agent selected from radionuclides, chemotherapeutic agents, nanoparticles, nanodroplets and cytokines.

In one embodiment, the cancer is a lymphoma or leukemia. In another embodiment, the lymphoma or leukemia is selected from the group consisting of non-Hodgkin's lymphoma, Hodgkin's lymphoma, B-cell lymphoma, T-cell lymphoma, multiple myeloma, Burkitt's lymphoma, acute lymphocytic leukemia, chronic lymphocytic leukemia, and hairy cell leukemia, or any other cancers expressing $\alpha_4\beta_1$-integrin. In certain instances, the compound is radiolabeled with a radionuclide by directly attaching the radionuclide to the ligand. In certain other instances, the radionuclide is bound to the chelating agent or chelating agent-linker conjugate attached to the ligand. Suitable radionuclides for direct conjugation include, without limitation, $^{18}$F, $^{124}$I, $^{125}$I, $^{131}$I, and mixtures thereof. Suitable radionuclides for use with a ligand-chelating agent conjugate include, without limitation, $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$Ag, $^{117m}$Sn, $^{149}$Pm, $^{153}$Sm, $^{166}$Ho, $^{177}$Lu, $^{186}$Re, $^{188}$Re, $^{211}$At, $^{212}$Bi, and mixtures thereof. Preferably, the radionuclide bound to a chelating agent is $^{64}$Cu, $^{90}$Y, $^{111}$In, or mixtures thereof. Suitable chelating agents include, but are not limited to, DOTA, BAD, TETA, DTPA, EDTA, NTA, HDTA, their phosphonate analogs, and mixtures thereof. One of ordinary skill is familiar with methods for attaching radionuclides, chelating agents, and chelating agent-linker conjugates to the ligands of the present invention. In particular, attachment of radionuclides, chelating agents, and chelating agent-linker conjugates to the ligands of the present invention can be conveniently accomplished using, for example, commercially available bifunctional linking groups (generally heterobifunctional linking groups) that can be attached to a functional group present in a non-interfering position on the compound and then further linked to, for example, a radionuclide, chemotherapeutic agent, anticancer agent, nanoparticle, quantum dot, nanodroplet of an anticancer agent or a small molecule toxin. In this manner, the compounds of the present invention can be used to carry suitable agents to a target site, generally, a tumor or organ or tissue having cancerous cells expressing $\alpha_4\beta_1$-integrin.

One skilled in the art will also appreciate that the compounds of the present invention can be co-administered with other therapeutic agents for the treatment of cancer. Suitable anti-cancer agents for combination therapy include, without limitation, cytotoxins and agents such as antimetabolites, alkylating agents, anthracyclines, antibiotics, antimitotic agents, procarbazine, hydroxyurea, asparaginase, corticosteroids, interferons, radiopharmaceuticals, peptides with anti-tumor activity such as TNF-$\alpha$, pharmaceutically acceptable salts thereof; derivatives thereof, prodrugs thereof, and combinations thereof.

In yet another aspect, the present invention provides a method for imaging a tumor, organ, or tissue, the method comprising:

(a) administering to a subject in need of such imaging, a compound having the formula:

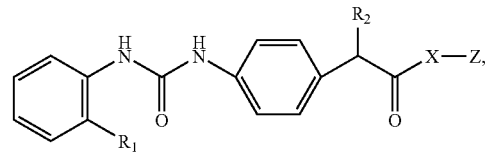

wherein $R_1$ is selected from the group consisting of —H, a $C_1$-$C_4$ alkyl group, a $C_1$-$C_4$ alkoxy group, a $C_1$-$C_4$ haloalkyl group, and a halogen;

$R_2$ is selected from the group consisting of —H, a $C_1$-$C_4$ alkyl group, and a $C_3$-$C_8$ cycloalkyl group;

X is a peptide having n independently selected amino acids, wherein at least one amino acid is selected from the group consisting of an unnatural amino acid and a D-amino acid;

Z is an imaging moiety; and n is an integer of from 3 to 20; and (b) detecting the compound to determine where the compound is concentrated in the subject.

In one embodiment, the imaging moiety is selected from the group consisting of a radionuclide, biotin, a fluorophore such as fluorescein, rhodamine, Texas Red, Cy2, Cy3, or Cy5, an antibody, horseradish peroxidase, and alkaline phosphatase. In certain instances, the compound is radiolabeled with a radionuclide by directly attaching the radionuclide to the ligand. In certain other instances, the radionuclide can be bound to a chelating agent attached to the ligand. Suitable radionuclides for direct conjugation include, without limitation, $^{18}$F, $^{131}$I, and mixtures thereof. Suitable radionuclides for use with a ligand-chelating agent conjugate include, without limitation, $^{55}$Co, $^{60}$Cu, $^{61}$Cu, $^{62}$Cu, $^{64}$Cu, $^{66}$Ga, $^{67}$Cu, $^{67}$Ga, $^{68}$Ga, $^{82}$Rb, $^{86}$Y, $^{87}$Y, $^{90}$Y, $^{111}$In, $^{99m}$Tc, $^{201}$Tl, and mixtures thereof. Preferably, the radionuclide bound to a chelating agent is $^{64}$Cu, $^{90}$Y, $^{111}$In, or mixtures thereof. Suitable chelating agents include, but are not limited to, DOTA, BAD, TETA, DTPA, EDTA, NTA, HDTA, their phosphonate analogs, and mixtures thereof. One of ordinary skill in the art will know of methods for attaching radionuclides, chelating agents, and other imaging moieties to the ligands of the present invention.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled compound of the present invention. Positron emission tomography (PET) is another suitable technique for detecting radiation in a subject. Furthermore, U.S. Pat. No. 5,429,133 describes a laparoscopic probe for detecting radiation concentrated in solid tissue tumors. Miniature and flexible radiation detectors intended for medical use are produced by Intra-Medical LLC, Santa Monica, Calif. Magnetic Resonance Imaging (MRI) or any other imaging technique known to one of skill in the art is also suitable for detecting the radioactive emissions of radionuclides. Regardless of the method or device used, such detection is aimed at determining where the compound is concentrated in a subject, with such concentration being an indicator of the location of a tumor or tumor cells.

In still yet another aspect, the present invention provides a method for treating an inflammatory or autoimmune disease in a subject in need thereof, the method comprising:

administering to the subject a therapeutically effective amount of a compound having the formula:

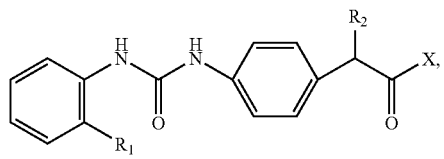

wherein
$R_1$ is selected from the group consisting of —H, a $C_1$-$C_4$ alkyl group, a $C_1$-$C_4$ alkoxy group, a $C_1$-$C_4$ haloalkyl group, and a halogen;
$R_2$ is selected from the group consisting of —H, a $C_1$-$C_4$ alkyl group, and a $C_3$-$C_8$ cycloalkyl group;
X is a peptide having n independently selected amino acids, wherein at least one amino acid is selected from the group consisting of an unnatural amino acid and a D-amino acid; and
n is an integer of from 3 to 20.

Any of a variety of imflammatory or autoimmune diseases such as those described above are suitable for treatment with the compounds of the present invention. Preferably, the autoimmune disease is multiple sclerosis, rheumatoid arthritis, or lupus.

One skilled in the art will appreciate that the compounds of the present invention can be co-administered with other therapeutic agents for the treatment of imflammatory or autoimmune diseases. Suitable anti-imflammatory agents for combination therapy include, without limitation, corticosteroids, non-steroidal anti-inflammatory agents, antibodies such as infliximab, 5-aminosalicylates, antibiotics, pharmaceutically acceptable salts thereof; derivatives thereof, prodrugs thereof, and combinations thereof. Suitable immunosuppressive agents for combination therapy include, without limitation, azathioprine and metabolites thereof, anti-metabolites such as methotrexate, immunosuppressive antibodies, mizoribine monophosphate, cyclosporine, scoparone, FK-506 (tacrolimus), FK-778, rapamycin (sirolimus), glatiramer acetate, mycopehnolate, pharmaceutically acceptable salts thereof, derivatives thereof, prodrugs thereof, and combinations thereof.

In a further aspect, the present invention provides kits for imaging a tumor, organ, or tissue or for treating cancer, an inflammatory disease, or an autoimmune disease comprising one or more of the above-described compounds and directions for use in imaging or therapy.

IV. Compositions: $\alpha_4\beta_1$ integrin inhibitors

The $\alpha_4\beta_1$ integrin inhibitors of the present invention were identified using the "one-bead one-compound" (OBOC) combinatorial library method.

Combinatorial library methods not only offer great potential for facilitating the drug discovery process, but also provide powerful tools for basic research in various disciplines (Lam, *Anti-Cancer Drug Design*, 12:145-167 (1997); Tiebes, In "Comb. Chem." Ed. Weinheim, J. G. Wiley-VCH. pp. 1-34 (1999); Antonenko et al., *Methods Princ. Med. Chem.*, 7:39- 80 (2000); Lehn and Eliseev, *Science*, 291:2331-2332 (2001); Appell et al., *Sep. Sci. Technol.*, 3:23-56 (2001)).

The OBOC combinatorial library method was first reported in 1991 (Lam et al., *Nature*, 354:82-84 (1991)). In essence, when a "split-mix" synthesis method (Lam et al., id; Houghten et al., *Nature*, 354:84-86 (1991); Furka et al., *Int. J. Peptide Protein Res.*, 37:487-493 (1991)) is used to generate a combinatorial library, each bead expresses only one chemical entity (Lam et al., id; Lam et al., *Chem. Rev.*, 97:411-448 (1997)). Random libraries of millions of beads can then be screened in parallel for a specific acceptor molecule (e.g., receptor, antibody, enzyme, virus, whole cell, etc.). Using an enzyme-linked calorimetric assay similar to that used in Western blotting, the OBOC combinatorial library method was successful in identifying ligands for an anti-β-endorphin antibody (Lam et al., *Bioorg. Med. Chem. Lett.*, 3:419-424 (1993)), streptavidin (Lam et al., *Pept.: Chem., Struct., Biol., Proc. Am. Pept. Symp.* 13th, pp. 1005-1006 (1994)), avidin (Lam and Lebl, *ImmunoMethods*, 1:11-15 (1992)), anti-insulin monoclonal antibody recognizing a discontinuous epitope (Lam et al., In "Peptides: Chem., Sturct., and Biol." Ed. Hodges, pp. 1003-1004 (1994)), MHC-Class I molecules (Smith et al., *Mol. Immunol.*, 31:1431-1437 (1994)), indigo carmine (a small organic dye) (Lam et al., *Drug Dev. Res.*, 33:157-160 (1994)), and surface idiotype of B-cell lymphoma cell lines (Lam et al., *Biomed. Pept, Prot., and Nuc. Acids*, 1:205-210 (1995)). The positive beads were then physically isolated for structural determination by microsequencing using automatic Edman degradation (Lam et al., *Nature*, 354:82-84 (1991)).

The OBOC combinatorial library method can also be used for screening radiolabeled peptides. For example, substrate motifs for protein kinases were identified using peptides radiolabeled with [$\gamma$-$^{32}$P]-ATP. (Lam and Wu, *Methods*, 6:401-403 (1994); Wu et al., *Biochem.*, 33:14825-14833 (1994); Lam et al., *Intl. J. Prot. Pept. Res.*, 45:587-592 (1995); Lou et al., *Bioorg. Med. Chem.*, 4:677-682 (1996)). Using these peptide substrates as templates, potent pseudo-substrate-based peptide inhibitors for p60$^{c\text{-}src}$ protein tyrosine kinase were also developed (Alfaro-Lopez et al., *J. Med. Chem.*, 41:2252-2260 (1998)). Since the OBOC combinatorial library method uses a parallel approach, each compound is spatially separated on individual beads, and multiple different peptide motifs can be identified (Wu et al., *J Comb. Chem. High-throughput screening* (2002)). Recently, OBOC combinatorial peptidomimetic libraries were used to identify peptidomimetic substrates for the development of c-src inhibitors (Kamath et al., In "Peptides: the wave of the fuiture." Proc. of Pept. Symp., Jun. 9-14, 2001).

Using 4-((N'-2-methylphenyl)ureido)-phenylacetyl-LDVP ("BIO-1211") as a template, various OBOC combinatorial peptidomimetic libraries containing both naturally-occurring amino acids, unnatural amino acids, and D-amino acids were designed to elucidate $\alpha_4\beta_1$ integrin ligands with increased affinity, specificity, and stability. In order to remove ligands with low to moderate binding affinity, the screening method was modified by incorporating BIO-1211 as a competitive ligand in solution. As a result, only those ligands with high affinity were completely covered by a monolayer of live lymphoid cancer cells. Cancer cell-binding affinity was performed on Jurkat T leukemia cells, Molt-4 leukemia cells, and/or fresh cancer cells obtained from acute lymphocytic leukemia patients. By using this method, $\alpha_4\beta_1$ integrin ligands with affinity significantly higher than that of BIO-1211 were identified. Furthermore, all of the ligands identified contained at least one unnatural α-amino acid, D-amino acid, or a combination thereof, a property that confers greater stability to the ligands upon administration. Therefore, these ligands have significantly better pharmacokinetic properties as well as cancer targeting properties compared to BIO-1211. Examples 2-8 provide a detailed description of the ligands identified from each of the various OBOC combinatorial peptidomimetic libraries.

In addition to their use as therapeutic agents for cancer, inflammatory diseases, and autoimmune diseases, the $\alpha_4\beta_1$ integrin ligands of the present invention are also suitable for use as imaging agents for imaging tumors, organs, and tissues. Preferably, the ligands are conjugated to an imaging moiety such as a radionuclide, a chelating agent, a fluorophore, an antibody, biotin, horseradish peroxidase, alkaline phosphatase, or a derivative thereof. One of ordinary skill in the art will appreciate other imaging moieties suitable for conjugation to the ligands of the present invention.

V. Methods of Administration

The ligands of the present invention have particular utility in human and veterinary imaging, therapeutic, and diagnostic applications. For example, the ligands can be used for imaging tumors and for treating cancer, inflammatory diseases, and autoimmune diseases.

Administration of the ligands of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. Moreover, where injection is to treat a tumor, administration may be directly to the tumor and/or into tissues surrounding the tumor.

The compositions containing a ligand or a combination of ligands of the present invention may be administered repeatedly, e.g., at least 2, 3, 4, 5, 6, 7, 8, or more times, or the composition may be administered by continuous infusion. Suitable sites of administration include, but are not limited to, dermal, mucosal, bronchial, gastrointestinal, anal, vaginal, eye, and ear. The formulations may take the form of solid, semi-solid, lyophilized powder, or liquid dosage forms, such as, for example, tablets, pills, lozenges, capsules, powders, solutions, suspensions, emulsions, suppositories, retention enemas, creams, ointments, lotions, gels, aerosols, or the like, preferably in unit dosage forms suitable for simple administration of precise dosages.

The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a ligand or a combination of ligands.

Methods for preparing such dosage forms are known to those skilled in the art (see, for example, REMINGTON'S PHARMACEUTICAL SCIENCES, 18TH ED., Mack Publishing Co., Easton, Pa. (1990)). The composition to be administered contains a quantity of the ligand or combination of ligands in a pharmaceutically effective amount for imaging a tumor, organ, or tissue or for relief of a condition being treated, when administered in accordance with the teachings of this invention. In addition, pharmaceutically acceptable salts of the ligands of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of a ligand of the present invention or a combination thereof, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The compositions can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; coloring agents; and flavoring agents. The compositions may also comprise biodegradable polymer beads, dextran, and cyclodextrin inclusion complexes.

For oral administration, the compositions can be in the form of tablets, lozenges, capsules, emulsions, suspensions, solutions, syrups, sprays, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the ligands or combination of ligands, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The ligands can also be formulated into a suppository disposed, for example, in a polyethylene glycol (PEG) carrier.

Liquid compositions can be prepared by dissolving or dispersing a ligand or a combination of ligands and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The ligands of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the ligand to the appropriate site or sites. However, one of ordinary skill in the art understands that the dose administered will vary depending on a number of factors, including, but not limited to, the particular ligand or set of ligands to be administered, the mode of administration, the type of application (e.g., imaging, therapeutic), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased cell binding affinity and specificity associated with the ligands of the present invention permits a wider margin of safety for dosage concentrations and for repeated dosing.

VI. Examples

The following examples are offered to illustrate, but not to limit, the claimed invention. A number of amino acids, analogs of amino acids and amino acid replacements are provided along with their abbreviations in the tables below and throughout the specification. One of skill in the art will appreciate that those abbreviations are also used for brevity in the attached claims.

Example 1

Synthesis of OBOC Combinatorial Libraries

All OBOC peptidomimetic libraries were synthesized on a TentaGel resin (Rapp Polymere, Tubingen, Germany) using a split/mix synthesis approach. The building blocks for library synthesis were either sequenceable amino acids (i.e., α-amino acids) or those encoded with sequenceable amino acids. The beads were made up of two layers, an outer layer (testing molecule) and an inner layer (coding tag). Orthogonal protecting groups such as Fmoc/Boc/Alloc/Dde were employed for amine group protection during library synthesis. Fmoc/t-But (9-fluorenylmethoxycarbonyl/tert-butyl) amino acid and HOBt/DIC (1-hydroxybenzotriazole/diisopropylcarbodiimide) coupling chemistry were used for library synthesis on TentaGel. Three equivalent Fmoc-amino acids were used. Fmoc deprotection was achieved by 20% piperidine in DMF (5 min, 15 min). Amino acid side-chain protecting groups were removed in the last step with a cocktail reagent mixture (82.5% TFA: 5% phenol: 5% thioanisole: 5% water: 2.5% TIS).

Figure 9:
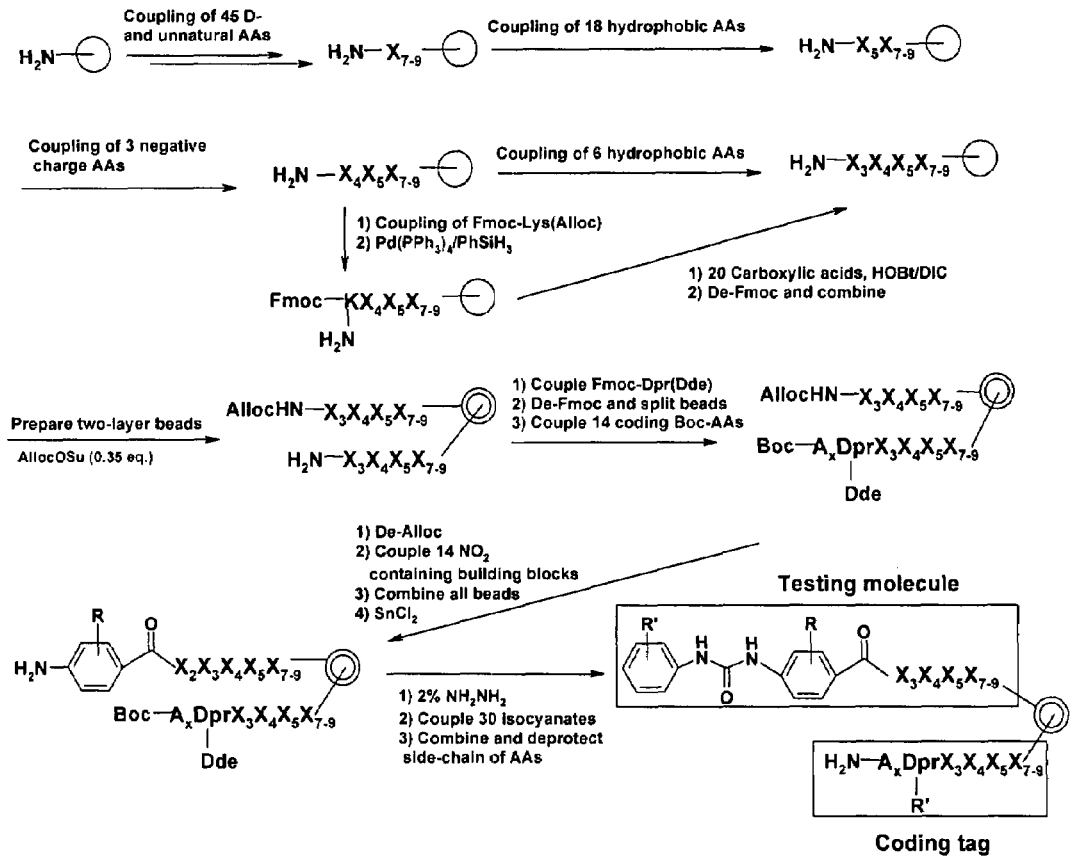
FIG. 9 shows the synthesis of the library L-1. The library is a mixture of three sub-libraries of ligands containing four, five, or six independently selected amino acids at positions $X_1$, $X_2$, $X_3$, $X_4$, and Y, wherein Y is a peptide fragment having m independently selected amino acids, and m is 0, 1, or 2.

A. Synthesis of OBOC Combinatorial Library L-1:

The synthesis of library L-1 is shown in FIG. 9 below. The library is a mixture of three sub-libraries of ligands containing four, five, or six independently selected amino acids at positions $X_1$, $X_2$, $X_3$, $X_4$, and Y, wherein Y is a peptide fragment having m independently selected amino acids, and m is 0, 1, or 2.

TentaGel beads (2.0 g, at 0.26 mmol/g) were swollen in DMF (20 mL) for 3 h. The resin was split into 45 equal portions in a 48-well multi-block. 45 different Fmoc-amino acids (3 equiv.) were separately dissolved in a solution of 1-hydroxybenzotriazole (HOBt) (3 equiv.) and DIC (3 equiv.) in DMF, and added to 45 columns, each column receiving one amino acid. Table 1 lists the 45 amino acids (i.e., 29 unnatural amino acids, 15 D-amino acids, and glycine) used in the synthesis. The coupling was carried out at room temperature for 2 h. After filtration, the beads were washed with DMF, MeOH, and DMF, respectively, three times each. One-third of the beads were then put aside.

TABLE 1

The 45 amino acids occurring at positions $X_4$ and Y in library L-1.

| No. | Amino acid |
| --- | --- |
| 1 | D-Asp |
| 2 | Acpc |
| 3 | D-Asn |
| 4 | D-Ser |
| 5 | D-Gln |
| 6 | D-Thr |
| 7 | HoSer |
| 8 | Gly |
| 9 | D-Glu |
| 10 | HoCit |
| 11 | Hyp |
| 12 | D-His |
| 13 | Aad |
| 14 | D-Ala |
| 15 | 4-Pal |
| 16 | D-3-Pal |
| 17 | Acdt |
| 18 | Ahch |
| 19 | Akch |
| 20 | D-Tyr |
| 21 | Aib |
| 22 | D-Pro |
| 23 | D-Met |
| 24 | D-Val |
| 25 | Nva |
| 26 | D-Thi |
| 27 | D-Trp |
| 28 | Tyr(Me) |
| 29 | Phg |
| 30 | D-Phe |
| 31 | D-Ile |
| 32 | Ach |
| 33 | Tyr(diBr) |
| 34 | Nle |
| 35 | D-Phe(4-Me) |
| 36 | Tyr(di I) |
| 37 | Aic |
| 38 | Phe(3-Cl) |
| 39 | D-HoPhe |
| 40 | Chg |
| 41 | D-Bpa |
| 42 | D-Nal-2 |
| 43 | Ana |

TABLE 1-continued

The 45 amino acids occurring at positions $X_4$ and Y in library L-1.

| No. | Amino acid |
|---|---|
| 44 | D-Phe(diCl) |
| 45 | Cha |

The D-stereoisomer of natural amino acid is designated by the standard three-letter code. Other abbreviations: Aad, α-aminohexanedioic acid; Acdt, 4-amino-4-carboxy-1,1-dioxo-tetrahydrothiopyran; Ach, 1-amino-1-cyclohexane carboxylic acid Acpc, 1-aminocyclopropane-1-carboxylic acid; Ahch, 1-amino-1-(4-hydroxycyclohexyl) carboxylic acid; Aic, 2-aminoindane-2-carboxylic acid; Aib, α-aminoisobutyric acid; Akch, 1-amino-1-(4-ketocyclohexyl)carboxylic acid; Ana, 2-amino-2-naphthylacetic acid; D-Bpa, D-4-benzoylphenylalanine; Bta, benzothienylalanine; Cha, cyclohexylalanine; Chg, α-cyclohexylglycine; Dpr, α,β-diaminopropionic acid; DPTU, diphenylthiourea; HoCit, Homocitrulline; D-HoPhe, D-homophenylalanine; HoSer, Homoserine; Hyp, hydroxy proline; D-Nal-2, D-3-(2-Naphthyl)alanine; Nle, norleucine; Nva, norvaline; D-3-Pal, D-3-(3-pyridyl)alanine; 4-Pal, 3-(4-pyridyl)alanine; Phe(3-Cl), 3-chlorophenylalanine; D-Phe (di Cl), D-3,4-dichlorophenylalanine; D-Phe(4-Me), D-4-methylphenylalanine; Phg, phenylglycine; D-Thi, D-3-(2-thienyl)alanine; Tyr(Me), O-methyltyrosine; Tyr(diBr), 3,5-dibromotyrosine; Tyr(diI), 3,5-diiodotyrosine.

The remaining two-thirds of the beads were subjected to Fmoc deprotection with 20% piperidine (5 min, 15 min). After washing with DMF, MeOH, and DMF, respectively, the beads were coupled with another set of the 45 Fmoc-amino acids as mentioned above. The beads were then split into two portions. Fmoc deprotection was performed on one portion and these beads were coupled with yet another set of the 45 Fmoc-amino acids as mentioned above. One skilled in the art will appreciate that the beads can be coupled with additional sets of the 45 Fmoc-amino acids by performing additional rounds of the coupling reaction.

All three sets of beads were combined, Fmoc deprotected, and split into 18 columns. The 18 hydrophobic amino acids shown in Table 2 were added to the columns and coupled to the beads at position $X_3$. Next, the 3 negatively charged amino acids shown in Table 3 were added to the columns and coupled to the beads at position $X_2$. At this point, the beads were split into 26 columns. The 6 hydrophobic amino acids shown in Table 4 were each separately added to one of 6 columns and coupled to the beads at position $X_1$. The beads in the remaining 20 columns were coupled with Fmoc-Lys(Alloc) and deprotected using $Pd(PPh_3)_4/PhSiH_3$, and the 20 carboxylic acid groups (i.e., R groups) shown in Table 5 were each separately added to one of these columns and coupled to the deprotected lysine by acylation in the presence of HOBt/DIC to form a lysine derivative at position $X_1$. After the coupling was finished, the beads from all 26 columns were combined and mixed before Fmoc deprotection with 20% piperidine (5 min, 15 min) was performed.

TABLE 2

The 18 hydrophobic amino acids occurring at position $X_3$ in library L-1.

| No. | $X_3$ | Structure |
|---|---|---|
| 1 | Ile | $H_2N$-CH(-CH(CH_3)CH_2CH_3)-COOH |
| 2 | Aib | $H_2N$-C(CH_3)_2-COOH |
| 3 | Abu | $H_2N$-CH(CH_2CH_3)-COOH |
| 4 | Leu | $H_2N$-CH(CH_2CH(CH_3)_2)-COOH |
| 5 | Pra | $H_2N$-CH(CH_2C≡CH)-COOH |
| 6 | Chg | $H_2N$-CH(cyclohexyl)-COOH |
| 7 | Nva | $H_2N$-CH(CH_2CH_2CH_3)-COOH |
| 8 | Phg | $H_2N$-CH(phenyl)-COOH |
| 9 | Cha | $H_2N$-CH(CH_2-cyclohexyl)-COOH |
| 10 | Val | $H_2N$-CH(CH(CH_3)_2)-COOH |
| 11 | Acpc | $H_2N$-C(cyclopropyl)-COOH |
| 12 | Ala | $H_2N$-CH(CH_3)-COOH |

TABLE 2-continued

The 18 hydrophobic amino acids occurring at position $X_3$ in library L-1.

| No. | $X_3$ | Structure |
|---|---|---|
| 13 | Nle | 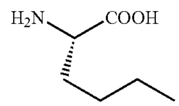 |
| 14 | Bug | 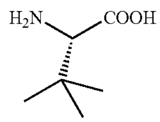 |
| 15 | Hle | 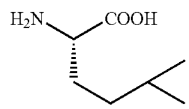 |
| 16 | Phe | 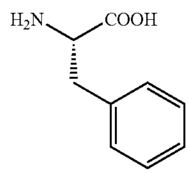 |
| 17 | HoPhe | 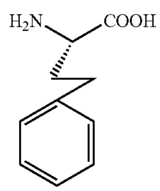 |
| 18 | Tyr | 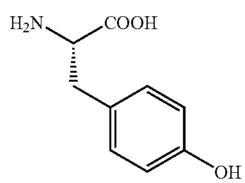 |

TABLE 3

The 3 negatively charged amino acids occurring at position $X_2$ in library L-1.

| No. | $X_2$ | Structure |
|---|---|---|
| 1 | Asp | 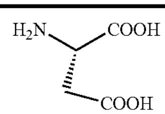 |
| 2 | Glu | 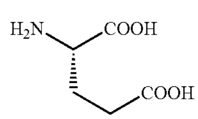 |
| 3 | Aad | 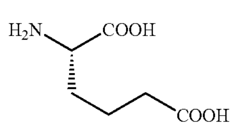 |

TABLE 4

The 6 hydrophobic amino acids occurring at position $X_1$ in library L-1.

| No. | $X_1$ | Structure |
|---|---|---|
| 1 | Nle | 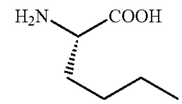 |
| 2 | Leu | 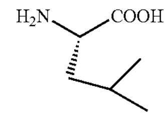 |
| 3 | Pra | 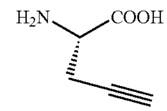 |
| 4 | HLe | 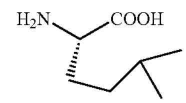 |
| 5 | Cpa | 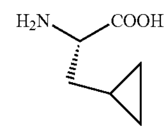 |
| 6 | Cha | 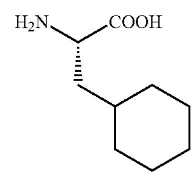 |

TABLE 5

The 20 lysine derivatives occurring at position $X_1$ in library L-1.

| $X_1$ | R group | Structure |
|---|---|---|
| Lys27 | L-Pyroglutamic acid | 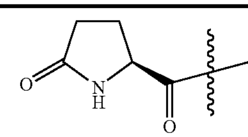 |
| Lys73 | trans-4-Cotinine carboxylic acid | 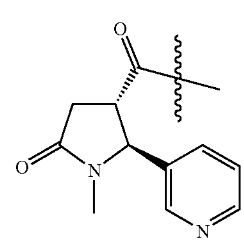 |

TABLE 5-continued

The 20 lysine derivatives occurring at position $X_1$ in library L-1.

| $X_1$ | R group | Structure |
|---|---|---|
| Lys55 | Levulinic acid | 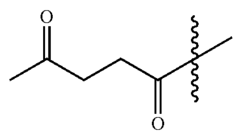 |
| Lys28 | Boc-1-amino cyclopropane-1-carboxylic acid | 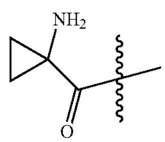 |
| Lys72 | 2-Pyrazine carboxylic acid | 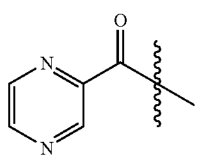 |
| Lys12 | 3-Pyradine propionic acid | 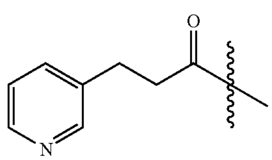 |
| Lys38 | trans-3-(3-Pyridyl)acrylic acid | 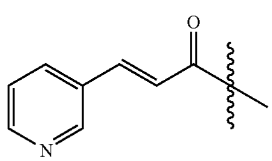 |
| Lys123 | Butyric acid | 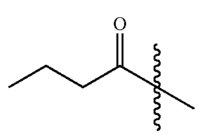 |
| Lys63 | 3-Oxo-1-indancarboxylic acid | 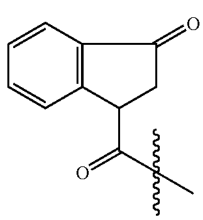 |
| Lys124 | Valeric acid | 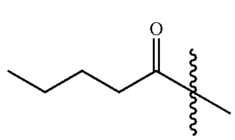 |
| Lys82 | (S)-(+)-Oxo-4-phenyl-3-oxazolidineacetic acid | |
| Lys31 | Boc-D-Tic | |
| Lys15 | 4-(Dimethylamino)phenylacetic acid | |
| Lys125 | Hexanoic acid | |
| Lys43 | Phenylpropionic acid | |
| Lys24 | 4-Chlorophenylacetic acid | |
| Lys5 | Bromophenylacetic acid | |
| Lys4 | 1-Naphthylacetic acid | |

TABLE 5-continued

The 20 lysine derivatives occurring at position $X_1$ in library L-1.

| $X_1$ | R group | Structure |
|---|---|---|
| Lys50 | 2-Phenoxybutyric acid | 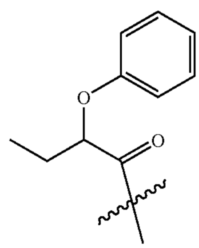 |
| Lys81 | 2,4-Dichlorophenyl-acetic acid | 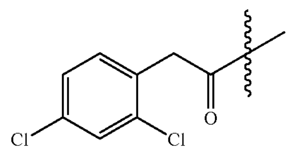 |

Two-layer beads were then prepared using a bi-phasic solvent approach (Liu et al., *J. Am. Chem. Soc.*, 124:7678-7680 (2002)). In brief, beads with a free amine group at the N-terminus were dried over vacuum completely and then swollen in water for 24 h. Water was removed by filtration, and a solution of AllocOSu in DCM/diethyl ether (200 ml, 55:45) was added to the beads, followed by the addition of diisoproylethylamine (DIEA). The mixture was shaken vigorously at room temperature for 30 min. The beads were washed three times with DCM/diethyl ether and six times with DMF to remove water from the beads.

Fmoc-Dpr(Dde) was then coupled to the inner bead layer. After Fmoc was removed with 20% piperidine, the beads were split into 14 columns and each column received one of the coding Boc-amino acids shown in Table 6. The Alloc protecting group was then removed in the above-mentioned manner. The beads in each of the 14 columns were coupled to one of the 14 $NO_2$-containing compounds (10 equiv. to resin) shown in Table 6 using HOBt/DIC coupling. After coupling was completed, the beads were combined and treated with 2M $SnCl_2$ in DMF to reduce the $NO_2$ group for 2 h (twice), followed by removal of Dde with 2% $NH_2NH_2$ (5 min, 10 min). The beads were then split again into 30 columns. One of the thirty isocyanantes shown in Table 7 and FIG. 1 was coupled to the free amine group of aniline (testing molecule) and Dpr (coding tag) simultaneously (2% DIEA in DMF, overnight).

TABLE 6

The 14 $NO_2$-containing compounds used in the synthesis of position B in library L-1.

| Boc-(AA) | $NO_2$-containing compound | Structure |
|---|---|---|
| Aib | 4-Nitrophenyl acetic acid | 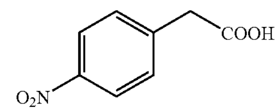 |
| Ala | 2-Nitrophenyl acetic acid | 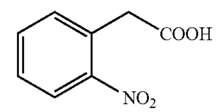 |
| Tyr | 4-(4-Nitrophenyl) butyric acid | 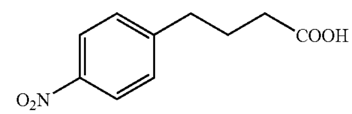 |
| Phe | 4-Nitrobenzoic acid | 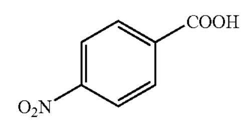 |
| Nva | 5-(4-Nitrophenyl)-2-furoic acid | 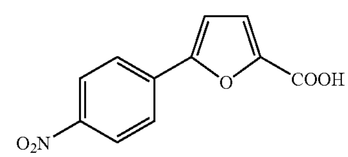 |
| Lys | 5-(2-Nitrophenyl)-2-furoic acid | 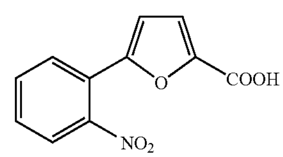 |
| Nle | 4-Nitrophenyl isocynate | 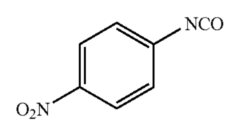 |
| Pro | 3-Nitrophenyl acetic acid | 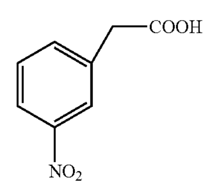 |
| Val | 4-Nitrocinnamic acid | 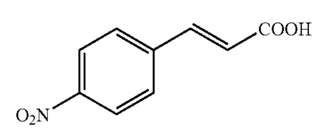 |
| Chg | 2-(4-Nitrophenyl) propionic acid | 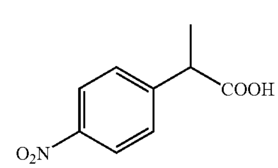 |

TABLE 6-continued

The 14 NO$_2$-containing compounds used in the synthesis of position B in library L-1.

| Boc-(AA) | NO$_2$-containing compound | Structure |
|---|---|---|
| Met | 5-(3-Nitrophenyl)-2-furoic acid | O$_2$N-C$_6$H$_4$-furan-COOH |
| Leu | 3-Nitrocinnamic acid | O$_2$N-C$_6$H$_4$-CH=CH-COOH |
| Asp | 4-Nitrophenyl chloroformate | O$_2$N-C$_6$H$_4$-O-C(O)-Cl |
| Ile | 4-Nitrohippuric acid | O$_2$N-C$_6$H$_4$-C(O)-NH-CH$_2$-COOH |

TABLE 7

The 30 isocyanates used in the synthesis of position A in library L-1.

| No. | Isocyanate |
|---|---|
| C1 | Ethyl isocyanatoacetate |
| C2 | Ethyl isocyanate |
| C3 | Isopropyl isocyanate |
| C4 | Propyl isocyanate |
| C5 | 3,4-Dimethoxyphenyl isocyanate |
| C6 | 4-(Dimethylamino)phenyl isocyanate |
| C7 | Butyl isocyanate |
| C8 | Cyclopentyl isocyanate |
| C9 | Phenyl isocyanate |
| C10 | 2,4-Dimethoxyphenyl isocyanate |
| C11 | 3-Methoxyphenyl isocyanate |
| C12 | O-Tolyl isocyanate |
| C13 | 2-Methoxyphenyl isocyanate |
| C14 | Cyclohexyl isocyanate |
| C15 | 2,3-Dimethylphenyl isocyanate |
| C16 | m-Tolyl isocyanate |
| C17 | 2-Bromophenyl isocyanate |
| C18 | 2,4-Dimethylphenyl isocyanate |
| C19 | Ethyl 3-isocyanatobenzoate |
| C20 | α,α,α-Trifluoro-o-tolyl isocyanate |
| C21 | 3-Chlorophenyl isocyanate |
| C22 | 3-Bromophenyl isocyanate |
| C23 | 2-tert-Butylphenyl isocyanate |
| C24 | α,α,α-Trifluoro-m-tolyl isocyanate |
| C25 | α,α,α-Trifluoro-p-tolyl isocyanate |
| C26 | 2-Biphenylyl isocyanate |
| C27 | 3,4-Dichlorophenyl isocyanate |
| C28 | 4-Isopopylphenyl isocyanate |
| C29 | 2,4-Dibromophenyl isocyanate |
| C30 | 3,5-Dichlorophenyl isocyanate |

The beads were washed with DMF (3×20 mL), methanol (3×20 mL), and DCM (3×20 mL). The beads were then dried under vacuum for 1 h. Side-chain deprotection was achieved using mixture of 82.5% TFA: 5% phenol: 5% thioanisole: 5% water: 2.5% TIS. After neutralization with 10% DIEA/DMF (twice), the resin was washed sequentially with DMF (3×20 mL), MeOH (3×20 mL), DCM (3×20 mL), DMF (3×20 mL), DMF/water (3×20 mL), water (3×20 mL), and PBS (10×20 mL).

B. Synthesis of OBOC Combinatorial Library L-2:

The synthesis of library L-2, shown in FIG. 10 below, is similar to the synthesis of library L-1. Since the majority of the ligands identified from library L-1 contained a 2-methylphenylureido group at position A (see, Example 2 below), only O-tolyl isocyanate was used at this position in library L-2. In addition, either 4-aminophenyl acetic acid or 2-methyl-4-aminophenyl acetic acid was used in the synthesis of position B in library L-2. This library is a mixture of three sub-libraries of ligands containing five, six, or seven independently selected amino acids at positions $X_1$, $X_2$, $X_3$, $X_4$, $X_5$, and Y, wherein Y is a peptide fragment having m independently selected amino acids, and m is 0, 1, or 2.

The coupling of the first three amino acids (i.e., $X_5$, $Y_1$, and $Y_2$) was performed in the same manner as that described for library L-1. Briefly, TentaGel beads (2.0 g, at 0.26 mmol/g) were swollen in DMF (20 mL) for 3 h. The resin was split into 45 equal portions in a 48-well multi-block. 45 different Fmoc-amino acids (3 equiv.), as shown in Table 1, were separately dissolved in a solution of HOBt (3 equiv.) and DIC (3 equiv.) in DMF, and added to 45 columns, each column receiving one amino acid. The coupling was carried out at room temperature for 2 h. After filtration, the beads were washed with DMF, MeOH, and DMF, respectively, three times each. One-third of beads were then put aside.

The remaining two-thirds of the beads were subjected to Fmoc deprotection with 20% piperidine (5 min, 15 min). After washing with DMF, MeOH, and DMF, respectively, the beads were coupled with another set of the forty-five Fmoc-amino acids shown in Table 1. The beads were then split into two portions. Fmoc deprotection was performed on one portion and these beads were coupled with another set of the 45 Fmoc-amino acids shown in Table 1. One skilled in the art will appreciate that the beads can be coupled with additional sets of the 45 Fmoc-amino acids by performing additional rounds of the coupling reaction.

All three sets of beads were combined, Fmoc deprotected, and split into 6 columns. The 6 proline analogs shown in Table 8 were coupled to the beads at position $X_4$. Then, the 26 hydrophobic amino acids shown in Table 9 were added to the columns and coupled to the beads at position $X_3$. Next, the 3 negatively charged amino acids shown in Table 3 (i.e., Asp, Glu, and Aad) were added to the columns and coupled to the beads at position $X_2$. At this point, the beads were split into 10 columns. The 7 hydrophobic amino acids shown in Table 10 were each separately added to one of 7 columns. The beads in the remaining 3 columns were coupled with Fmoc-Lys(Alloc) and deprotected using Pd(PPh$_3$)$_4$/PhSiH$_3$, and the carboxylic acid groups to form the lysine derivatives shown in Table 10 (i.e., Lys 38, Lys12, and Lys43) were each separately added to one of these columns and coupled to the deprotected lysine by acylation in the presence of HOBt/DIC (10 equiv.). After the coupling was finished, the beads from all 10 columns were combined and mixed before Fmoc deprotection with 20% piperidine (5 min, 15 min) was performed.

TABLE 8

The 6 proline analogs occurring at position $X_4$ in library L-2.

| No. | $X_4$ | Structure |
|---|---|---|
| 1 | Pro | 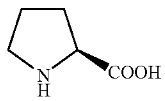 |
| 2 | Hyp | 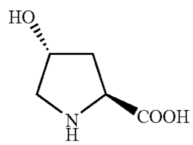 |
| 3 | Thz | 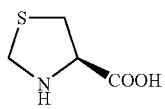 |
| 4 | Acp | 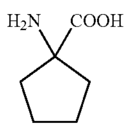 |
| 5 | Hyp(Bzl) | 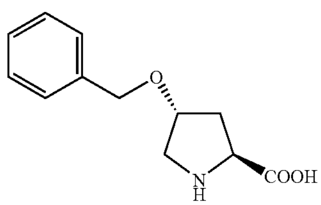 |
| 6 | Ppca | 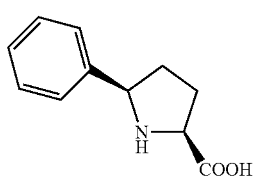 |

TABLE 9

The 26 hydrophobic amino acids occurring at position $X_3$ in library L-2.

| No. | $X_3$ | Structure |
|---|---|---|
| 1 | Ile | |
| 2 | Ala | |
| 3 | Abu | |
| 4 | Leu | 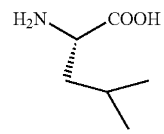 |
| 5 | Pra | 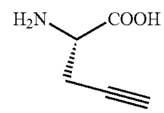 |
| 6 | Chg | 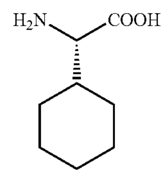 |
| 7 | Nva | 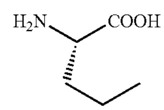 |
| 8 | Phg | 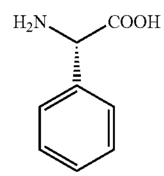 |
| 9 | Cha | 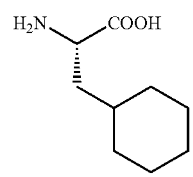 |
| 10 | Ach | 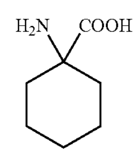 |
| 11 | Ppca | 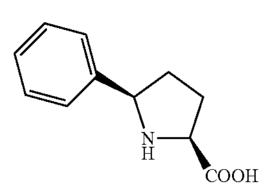 |
| 12 | Ana | 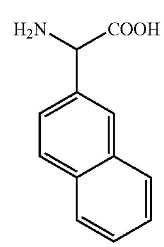 |

TABLE 9-continued
The 26 hydrophobic amino acids occurring at position $X_3$ in library L-2.
| No. | $X_3$ | Structure |
|---|---|---|
| 13 | Bpa | 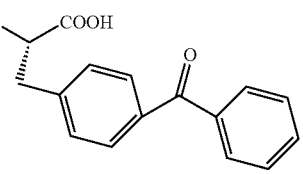 |
| 14 | Val | 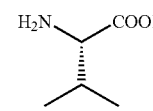 |
| 15 | Acpc | 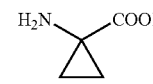 |
| 16 | Thi | 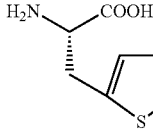 |
| 17 | Nle | 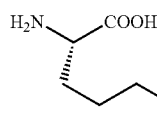 |
| 18 | D-Nal-2 | 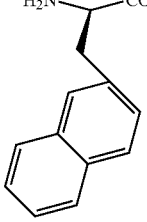 |
| 19 | Aic | 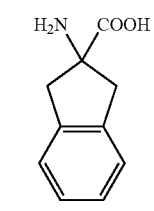 |
| 20 | D-Phe | 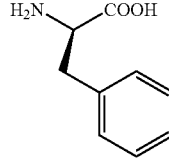 |
| 21 | HoPhe | 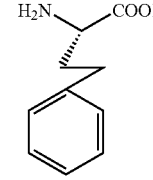 |
| 22 | Tyr | 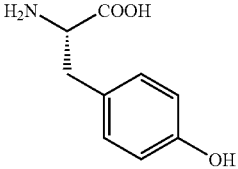 |
| 23 | Tyr(Me) | 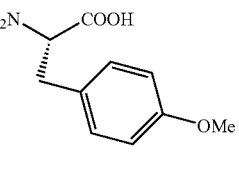 |
| 24 | Phe(3-Cl) | 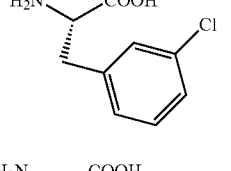 |
| 25 | Tyr(diI) | 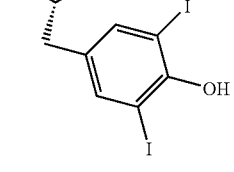 |
| 26 | Phe(4-Me) | 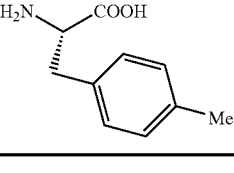 |
TABLE 10
The 10 amino acids occurring at position $X_1$ in library L-2.
| No. | $X_1$ | Structure |
|---|---|---|
| 1 | Nle | 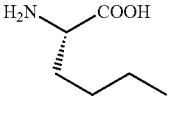 |
| 2 | Leu | 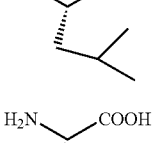 |
| 3 | HoPhe | 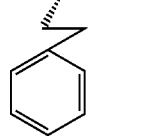 |

TABLE 10-continued

The 10 amino acids occurring at position $X_1$ in library L-2.

| No. | $X_1$ | Structure |
|---|---|---|
| 4 | Pra | H₂N-CH(COOH)-CH₂-C≡CH |
| 5 | Lys38 | H₂N-CH(COOH)-(CH₂)₄-NH-C(O)-CH=CH-(3-pyridyl) |
| 6 | Hle | H₂N-CH(COOH)-CH₂-CH(CH₃)-CH₂CH₃ |
| 7 | Cpa | H₂N-CH(COOH)-cyclopropyl |
| 8 | Cha | H₂N-CH(COOH)-CH₂-cyclohexyl |
| 9 | Lys12 | H₂N-CH(COOH)-(CH₂)₄-NH-C(O)-CH₂CH₂-(3-pyridyl) |
| 10 | Lys43 | H₂N-CH(COOH)-(CH₂)₄-NH-C(O)-CH₂CH₂-phenyl |

Two-layer beads were then prepared using the bi-phasic solvent approach as described for library L-1 above. The beads were split into 2 columns and each column received one coding Boc-amino acid (e.g., Boc-Ala, Boc-Leu). After Fmoc was removed with 20% piperidine, the beads were coupled overnight with either 2-(4-Nitrophenyl) propionic acid or 4-Nitrophenyl acetic acid (10 equiv. to resin) using the HOBt/DIC coupling method. The beads were then combined and treated with 2M $SnCl_2$ in DMF for 2 h (twice) to reduce the $NO_2$ group. Next, the beads were coupled with o-tolylisocyanate (10 equiv.) at room temperature overnight. The beads were washed with DMF (3×20 mL), methanol (3×20 mL), and DCM (3×20 mL). The beads were then dried under vacuum for 1 h. Side-chain deprotection was achieved using mixture of 82.5% TFA:5% phenol:5% thioanisole:5% water: 2.5% TIS. After neutralization with 10% DIEA/DMF (twice), the resin was washed sequentially with DMF (3×20 mL), MeOH (3×20 mL), DCM (3×20 mL), DMF (3×20 mL), DMF/water (3×20 mL), water (3×20 mL), and PBS (10×20 mL).

Figure 10:
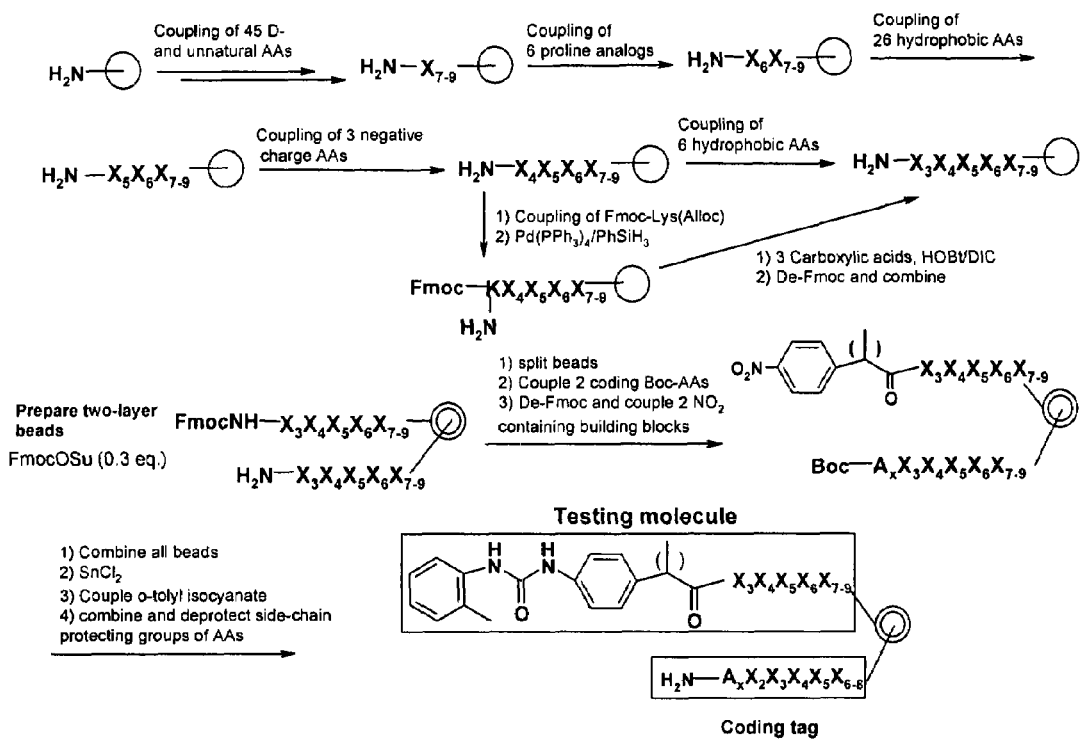
FIG. 10 shows the synthesis of library L-2, and is similar to the synthesis of library L-1. Since the majority of the ligands identified from library L-1 contained a 2-methylphenylureido group at position A, only O-tolyl isocyanate was used at this position in library L-2. In addition, either 4-aminophenyl acetic acid or 2-methyl-4-aminophenyl acetic acid was used in the synthesis of position B in library L-2.

C. Synthesis of OBOC Combinatorial Libraries L-3, L-4, and L-5:

Synthetic approaches for libraries L-3, L-4, and L-5 were similar to that described for library L-2 (see, FIG. 10). For library L-3, the set of 45 unnatural and D-amino acids was used at position $X_4$ instead of the proline analogs. For library L-4, the set of 45 unnatural and D-amino acids was used at positions $X_3$ and $X_4$ instead of the set of 26 hydrophobic amino acids and the proline analogs, respectively. Positions $X_4$, $X_5$, and Y are not found in library L-5. The synthesis of library L-5 is provided in Example 6.

Example 2

Ligands Identified from OBOC Combinatorial Library L-1

The first OBOC combinatorial peptidomimetic library (L-1) was synthesized by replacing the various substituents of BIO-1211 with small organic groups such as isocyanates, unnatural amino acids, and naturally-occurring amino acids. More particularly, the library contained compounds having the following structure:

A-B-$X_1$-$X_2$-$X_3$-$X_4$-Y, wherein A is one of the ureido groups derived from the 30 isocyanates shown in FIG. 1; B is one of the anilines derived from the 14 $NO_2$-containing compounds shown in Table 6 by reduction with $SnCl_2$; $X_1$ is one of the 20 lysine (Lys) analogs shown in Table 5 or one of the 6 leucine (Leu) analogs shown in Table 4; $X_2$ is one of the 3 negatively charged amino acids shown in Table 3; $X_3$ is one of the 18 hydrophobic amino acids shown in Table 2; $X_4$ is one of the 45 amino acids (i.e., 29 unnatural amino acids, 15 D-amino acids, and glycine) shown in Table 1; Y is a peptide fragment having m independently selected amino acids chosen from the amino acids shown in Table 1; and m is 0, 1, or 2.

This library was screened using a competitive cell-bead screening strategy such that only ligands with higher binding affinity than BIO-1211 were identified. To this end, the bead library was screened using Jurkat cells in the presence of BIO-1211. BIO-1211 competes with the bead-bound ligands for interaction with $\alpha_4\beta_1$ integrin on Jurkat cells. The concentration of free BIO-1211 in the competitive screening assay can be determined by titrating the binding signal of BIO-1211 beads. As such, the concentration of free BIO-1211 that can completely inhibit the binding of leukemia cells to BIO-1211 beads can be used for the competitive screening assay. Therefore, any positive bead identified in the screen has a higher binding affinity for leukemia cells than that of BIO-1211. One of skill in the art understands that false positive ligands, e.g., ligands that bind to a receptor other than $\alpha_4\beta_1$ integrin, can be identified by performing a reverse inhibition assay where the ligands are re-synthesized as free ligands (i.e., not bound to beads) and assayed for their ability to inhibit cell binding to BIO-1211 beads.

A total of 23 independent ligands were identified using this library with the screening strategy described above. These ligands are set forth in Table 11 below. All of the identified ligands have the following structure:

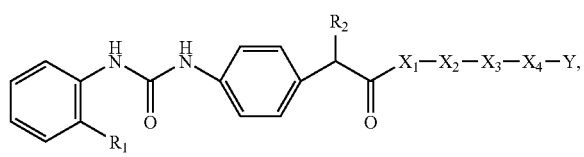

wherein $R_1$ is —H or —$CH_3$, $R_2$ is —H or —$CH_3$, and $X_1$, $X_2$, $X_3$, $X_4$, and Y are the same as defined above. As such, the results showed that a 2-(methylphenyl)ureido group is the preferred substituent at position A, as 22 out of 23 ligands contained this particular group at that position. Only 1 out of 23 ligands contained a phenylureido group at position A. In addition, a 4-aminophenyl acetyl group is the preferred substituent at position B, as 20 out of 23 ligands contained this particular group at that position. Only 3 out of 23 ligands contained a 2-methyl-4-aminophenyl acetyl group at position B. The remaining positions contained various combinations of naturally-occurring amino acids, unnatural amino acids, and/or D-amino acids that differed significantly from the naturally-occurring amino acids found in BIO-1211.

TABLE 11

$\alpha_4\beta_1$ integrin ligands identified from OBOC combinatorial library L-1.

| No. | A | B | $X_1$ | $X_2$ |
|---|---|---|---|---|
| 1 | 2-Methyl phenylureido | 4-Aminophenyl acetic acid | Nle | Aad |
| 2 | 2-Methyl phenylureido | 4-Aminophenyl acetic acid | Leu | Aad |
| 3 | 2-Methyl phenylureido | 2-Methyl-4-aminophenyl acetic acid | Cpa | Asp |
| 4 | 2-Methyl phenylureido | 4-Aminophenyl acetic acid | Leu | Aad |
| 5 | 2-Methyl phenylureido | 4-Aminophenyl acetic acid | Nle | Aad |
| 6 | 2-Methyl phenylureido | 4-Aminophenyl acetic acid | Cha | Aad |

TABLE 11-continued

α$_4$β$_1$ integrin ligands identified from OBOC combinatorial library L-1.

| # | | | | |
|---|---|---|---|---|
| 7 | 2-Methyl phenylureido | 4-Aminophenyl acetic acid | Cpa | Glu |
| 8 | 2-Methyl phenylureido | 4-Aminophenyl acetic acid | Hle | Aad |
| 9 | 2-Methyl phenylureido | 4-Aminophenyl acetic acid | Nle | Asp |
| 10 | 2-Methyl phenylureido | 4-Aminophenyl acetic acid | Lys38 | Aad |
| 11 | 2-Methyl phenylureido | 4-Aminophenyl acetic acid | Cha | Asp |
| 12 | 2-Methyl phenylureido | 4-Aminophenyl acetic acid | Cpa | Aad |
| 13 | 2-Methyl phenylureido | 4-Aminophenyl acetic acid | Hle | Aad |
| 14 | 2-Methyl phenylureido | 4-Aminophenyl acetic acid | Lys38 | Glu |

TABLE 11-continued

α₄β₁ integrin ligands identified from OBOC combinatorial library L-1.

| | | | | |
|---|---|---|---|---|
| 15 | 2-Methyl phenylureido | 2-Methyl-4-aminophenyl acetic acid | Nle | Asp |
| 16 | 2-Methyl phenylureido | 4-Aminophenyl acetic acid | Leu | Aad |
| 17 | Phenylureido | 4-Aminophenyl acetic acid | Cpa | Asp |
| 18 | 2-Methyl phenylureido | 4-Aminophenyl acetic acid | Leu | Aad |
| 19 | 2-Methyl phenylureido | 4-Aminophenyl acetic acid | Hle | Asp |
| 20 | 2-Methyl phenylureido | 4-Aminophenyl acetic acid | Cpa | Aad |
| 21 | 2-Methyl phenylureido | 4-Aminophenyl acetic acid | Cpa | Aad |
| 22 | 2-Methyl phenylureido | 4-Aminophenyl acetic acid | Cpa | Aad |

TABLE 11-continued
α₄β₁ integrin ligands identified from OBOC combinatorial library L-1.
| 23 | 2-Methyl phenylureido 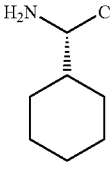 | 2-Methyl-4-aminophenyl acetic acid 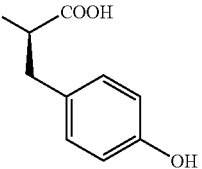 | Nle 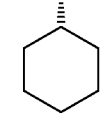 | Asp 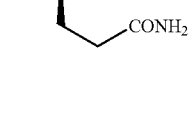 |
|---|---|---|---|---|
| STATISTICS | 22/23 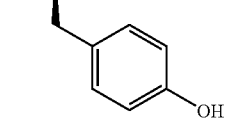<br><br>1/23 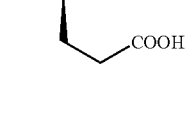 | 20/23 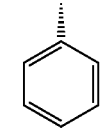<br><br>3/23 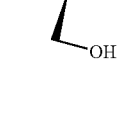 | Nle: 5<br>Leu: 4<br>Hle: 3<br>Cpa: 7<br>Cha: 2<br>Lys38: 2 | 14/23<br>Aad<br>7/23<br>Asp<br>2/23<br>Glu |
| No. | X₃ | X₄ | Y₁ | Y₂ |
|---|---|---|---|---|
| 1 | Chg 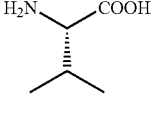 | D-Tyr | | |
| 2 | Chg | D-Gln | D-Tyr | |
| 3 | Phg 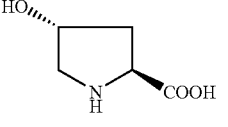 | D-Glu | D-Ser | |
| 4 | Val 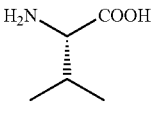 | Hyp 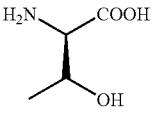 | | |
| 5 | Val | D-Thr 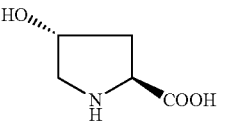 | Hyp | D-Asn 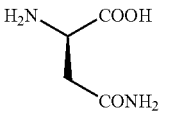 |

TABLE 11-continued
α₄β₁ integrin ligands identified from OBOC combinatorial library L-1.
| | | | | |
|---|---|---|---|---|
| 6 | Nle | D-Gln | D-Asn | |
| 7 | Val | D-Asp | D-Ala | |
| 8 | Phe | Chg | | |
| 9 | Pra | Gly | Hyp | |
| 10 | Leu | D-Pro | | |
| 11 | Val | D-Glu | D-Gln | |
| 12 | Ile | D-Asp | | |
| 13 | Aib | D-3-Pal | | |
| 14 | Acpc | Nle | D-Asp | D-Gln |
| 15 | Val | Ach | D-Ala | |
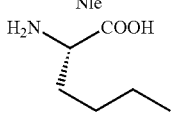

TABLE 11-continued
α₄β₁ integrin ligands identified from OBOC combinatorial library L-1.
| | | | | |
|---|---|---|---|---|
| 16 | Ala 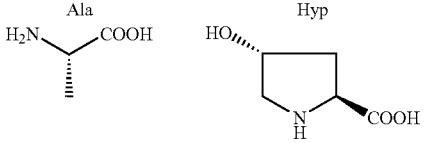 | Hyp 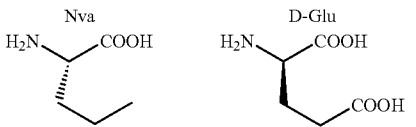 | | |
| 17 | Nva 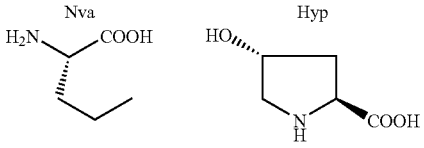 | D-Glu 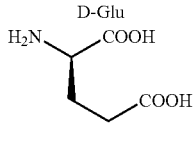 | | |
| 18 | Nva 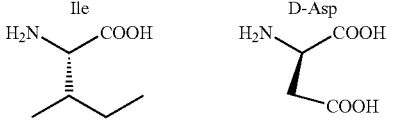 | Hyp 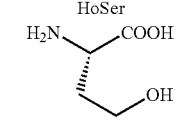 | D-Glu 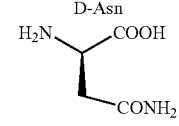 | |
| 19 | Ile 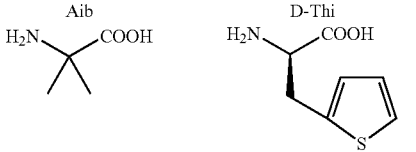 | D-Asp  | HoSer 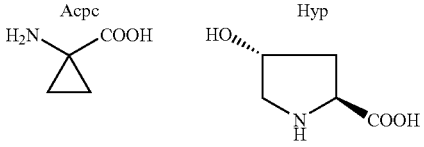 | D-Asn  |
| 20 | Aib 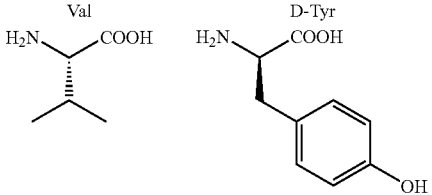 | D-Thi 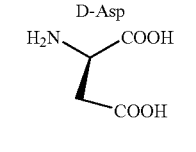 | | |
| 21 | Acpc 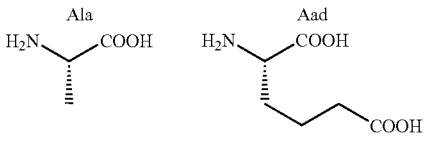 | Hyp 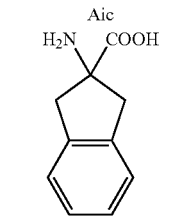 | | |
| 22 | Val | D-Tyr | D-Asp | |
| 23 | Ala | Aad | Aic | |
| STATISTICS | Val: 6<br>Ile: 2<br>Ala: 2<br>Leu: 1<br>Phe: 1<br>Aib: 2<br>Chg: 2<br>Acpc: 2<br>Nva: 2 | D-Pro: 1<br>Negative charge: 7<br>Hydrophobic: 6 | D-Asn and D-Gln: 2<br>D-Asp and D-Glu: 2<br>Hyp: 2<br>D-Ser: 1<br>Hoser: 1 | D-Asn and D-Gln: 3 |

TABLE 11-continued

α₄β₁ integrin ligands identified from OBOC combinatorial library L-1.

| Nle: 2 | D-Ala: 2 |
|---|---|
| Pra: 1 | Aic: 1 |
| Phg: 1 | |

Lys38 has the following structure:

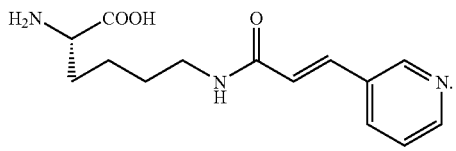

The ligands identified from this library have the following features: (1) hydrophobic amino acids such as leucine and leucine analogs (i.e., Nle, Hle, Cpa, Cha), and lysine derivatives such as Lys38 are preferred at position $X_1$; (2) negatively charged amino acids such as Aad, Asp, and Glu are preferred at position $X_2$; (3) hydrophobic amino acids are preferred at position $X_3$; (4) proline analogs (i.e., Hyp), hydrophobic amino acids, and negatively charged amino acids are preferred at position $X_4$; and (5) D-amino acids are preferred at positions $Y_1$ and $Y_2$.

Example 3

Ligands Identified from OBOC Combinatorial Library L-2

The second OBOC combinatorial peptidomimetic library (L-2) was also synthesized by replacing the various substituents of BIO-1211 with small organic groups such as isocyanates, unnatural amino acids, and naturally-occurring amino acids. More particularly, the library contained compounds having the following structure:

A-B-$X_1$-$X_2$-$X_3$-$X_4$-$X_5$-Y, wherein A is a 2-(methylphenyl)ureido group; B is either 4-aminophenyl acetic acid or 2-methyl-4-aminophenyl acetic acid; $X_1$ is one of 10 amino acids (i.e., hydrophobic amino acids and lysine derivatives) shown in Table 10; $X_2$ is one of 3 negatively charged amino acids shown in Table 3; $X_3$ is one of 26 hydrophobic amino acids shown in Table 9; $X_4$ is one of 6 proline analogs shown in Table 8; $X_5$ is one of the 45 amino acids (i.e., 29 unnatural amino acids, 15 D-amino acids, and glycine) shown in Table 1; Y is a peptide fragment having m independently selected amino acids chosen from the amino acids shown in Table 1; and m is 0,1, or 2.

This library was also screened using a competitive cell-bead screening strategy as described above, such that only ligands with higher binding affinity than BIO-1211 were identified. A total of 8 independent ligands were identified using this library. These ligands are set forth in Table 12 below. All of the identified ligands have the following structure:

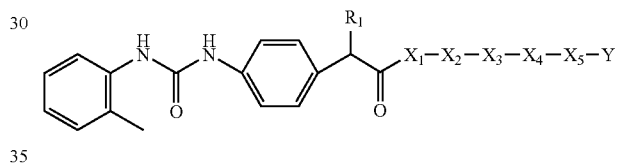

wherein $R_1$ is —H or —$CH_3$ and $X_1$, $X_2$, $X_3$, $X_4$, $X_5$, and Y are the same as defined above. As such, the results showed that a 4-aminophenyl acetyl group is the preferred substituent at position B, as 6 out of 8 ligands contained this particular group at that position. Only 2 out of 8 ligands contained a 2-methyl-4-aminophenyl acetyl group at position B. The remaining positions contained various combinations of naturally-occurring amino acids, unnatural amino acids, and/or D-amino acids that differed significantly from the naturally-occurring amino acids found in BIO-1211.

TABLE 12

α₄β₁ integrin ligands identified from OBOC combinatorial library L-2.

| No. | B | $X_1$ | $X_2$ | $X_3$ |
|---|---|---|---|---|
| 1 | 4-Aminophenyl acetic acid 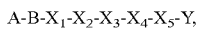 | Cha | Asp | HoPhe |

TABLE 12-continued

α₄β₁ integrin ligands identified from OBOC combinatorial library L-2.

| # | AA1 | AA2 | AA3 | AA4 |
|---|---|---|---|---|
| 2 | 4-Aminophenyl acetic acid | Nle | Aad | Chg |
| 3 | 4-Aminophenyl acetic acid | Nle | Aad | Chg |
| 4 | 4-Aminophenyl acetic acid | Cpa | Aad | Chg |
| 5 | 4-Aminophenyl acetic acid | Cpa | Aad | Chg |
| 6 | 4-Aminophenyl acetic acid | Nle | Aad | Chg |
| 7 | 2-Methyl-4-aminophenyl acetic acid | Hle | Aad | Val |
| 8 | 2-Methyl-4-aminophenyl acetic acid | Nle | Glu | Phg |

TABLE 12-continued

α₄β₁ integrin ligands identified from OBOC combinatorial library L-2.

| No. | X₄ | X₅ | Y₁ | Y₂ |
|-----|-----|-----|-----|-----|
| 1 | Hyp | D-3-Pal | Nle | Ach |
| 2 | Hyp | Aad | | |
| 3 | Hyp | D-Val | D-Asp | D-Asp |
| 4 | Pro | Aad | Phe(3-Cl) | Aad |
| 5 | Acp | D-Asp | D-Glu | |
| 6 | Hyp | D-Glu | Ach | |
| 7 | Hyp | Chg | | |
| 8 | Acp | Aad | | |

The ligands identified from this library have the following features: (1) hydrophobic amino acids such as leucine analogs (i.e., Nle, Hle, Cpa, Cha) are preferred at position X₁; (2) the negatively charged amino acid Aad is preferred at position X₂; (3) hydrophobic amino acids such as Chg and phenylalanine analogs (i.e., HoPhe, Phg) are preferred at position X₃;

(4) proline analogs (i.e., Hyp, Acp) are preferred at position $X_4$; and (5) D-amino acids and negatively charged amino acids are preferred at positions $X_5$, $Y_1$, and $Y_2$.

Example 4

Ligands Identified from OBOC Combinatorial Library L-3

The third OBOC combinatorial peptidomimetic library (L-3) was also synthesized by replacing the various substituents of BIO-1211 with small organic groups such as isocyanates, unnatural amino acids, and naturally-occurring amino acids. More particularly, the library contained compounds having the following structure:

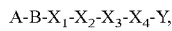

A-B-$X_1$-$X_2$-$X_3$-$X_4$-Y, wherein A is a 2-(methylphenyl)ureido group; B is either 4-aminophenyl acetic acid or 2-methyl-4-aminophenyl acetic acid; $X_1$ is one of 10 amino acids shown in Table 10; $X_2$ is one of 3 negatively charged amino acids shown in Table 3; $X_3$ is one of 26 hydrophobic amino acids shown in Table 9; $X_4$ is one of the 45 amino acids shown in Table 1; Y is a peptide fragment having m independently selected amino acids chosen from the amino acids shown in Table 1; and m is 0 or 1.

This library was also screened using a competitive cell-bead screening strategy as described above, such that only ligands with higher binding affinity than BIO-1211 were identified. A total of 10 independent ligands were identified using this library. These ligands are set forth in Table 13 below. All of the identified ligands have the following structure:

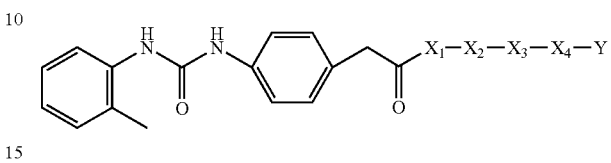

wherein $X_1$, $X_2$, $X_3$, $X_4$, and Y are the same as defined above. As such, the results showed that a 4-aminophenyl acetyl group is the preferred substituent at position B, as all ligands contained this particular group at that position. The remaining positions contained various combinations of naturally-occurring amino acids, unnatural amino acids, and/or D-amino acids that differed significantly from the naturally-occurring amino acids found in BIO-1211.

TABLE 13

$\alpha_4\beta_1$ integrin ligands identified from OBOC combinatorial library L-3.

| No. | B | $X_1$ | $X_2$ |
|---|---|---|---|
| S1 | 4-Aminophenyl acetic acid | Nle | Aad |
| S2 | 4-Aminophenyl acetic acid | Lys38 | Aad |
| S3 | 4-Aminophenyl acetic acid | Lys38 | Aad |
| S4 | 4-Aminophenyl acetic acid | Lys38 | Aad |

TABLE 13-continued

α₄β₁ integrin ligands identified from OBOC combinatorial library L-3.

| No. | | | |
|---|---|---|---|
| S5 | 4-Aminophenyl acetic acid | Nle | Aad |
| M1 | 4-Aminophenyl acetic acid | Hle | Aad |
| M2 | 4-Aminophenyl acetic acid | Lys38 | Aad |
| M3 | 4-Aminophenyl acetic acid | Cpa | Aad |
| M4 | 4-Aminophenyl acetic acid | Lys38 | Aad |
| M5 | 4-Aminophenyl acetic acid | Cpa | Aad |

| No. | $X_3$ | $X_4$ | $Y_1$ |
|---|---|---|---|
| S1 | Val | D-Glu | |
| S2 | Acpc | D-Asp | |
| S3 | Acpc | D-Asn | D-Asn |

TABLE 13-continued

α₄β₁ integrin ligands identified from OBOC combinatorial library L-3.

| | | | |
|---|---|---|---|
| S4 | D-Phe | D-3-Pal | |
| S5 | Cha | D-Glu | |
| M1 | Ile | D-Asp | Nle |
| M2 | Aic | D-Glu | D-Tyr |
| M3 | Nle | D-Pro | |
| M4 | Chg | D-Glu | |
| M5 | Chg | D-Ser | Gly |

The ligands identified from this library have the following features: (1) ligands in Group S have a higher binding affinity than ligands in Group M; (2) hydrophobic amino acids such as leucine analogs (i.e., Nle, Hle, Cpa), and lysine derivatives such as Lys38 are preferred at position $X_1$; (3) the negatively charged amino acid Aad is preferred at position $X_2$; (4) hydrophobic amino acids are preferred at position $X_3$; and (5) D-amino acids, especially negatively charged D-amino acids, are preferred at position $X_4$.

Example 5

Ligands Identified from OBOC Combinatorial Library L-4

The fourth OBOC combinatorial peptidomimetic library (L-4) was also synthesized by replacing the various substituents of BIO-1211 with small organic groups such as isocyanates, unnatural amino acids, and naturally-occurring amino acids. More particularly, the library contained compounds having the following structure:

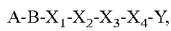

A-B-$X_1$-$X_2$-$X_3$-$X_4$-Y, wherein A is a 2-(methylphenyl)ureido group; B is either 4-aminophenyl acetic acid or 2-methyl-4-aminophenyl acetic acid; $X_2$ is one of 3 negatively charged amino acids shown in Table 3; $X_3$, and $X_4$ are each independently selected from the set of 45 amino acids shown in Table 1; Y is a peptide fragment having m independently selected amino acids chosen from the amino acids shown in Table 1; and m is 0 or 1.

This library was also screened using a competitive cell-bead screening strategy as described above, such that only ligands with higher binding affinity than BIO-1211 were identified. A total of 9 independent ligands were identified using this library. These ligands are set forth in Table 14 below. All of the identified ligands have the following structure:

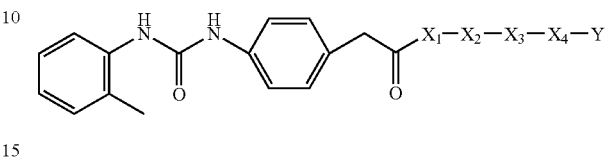

wherein $X_1$, $X_2$, $X_3$, $X_4$, and Y are the same as defined above. As such, the results showed that a 4-aminophenyl acetyl group is the preferred substituent at position B, as all ligands contained this particular group at that position. The remaining positions contained various combinations of naturally-occurring amino acids, unnatural amino acids, and/or D-amino acids that differed significantly from the naturally-occurring amino acids found in BIO-1211.

TABLE 14

$\alpha_4\beta_1$ integrin ligands identified from OBOC combinatorial library L-4.

| No. | B | $X_1$ | $X_2$ |
|---|---|---|---|
| 1 | 4-Aminophenyl acetic acid | Cpa | Aad |
| 2 | 4-Aminophenyl acetic acid | Cpa | Aad |
| 3 | 4-Aminophenyl acetic acid | Leu | Aad |
| 4 | 4-Aminophenyl acetic acid | Nle | Aad |

TABLE 14-continued

α₄β₁ integrin ligands identified from OBOC combinatorial library L-4.

| No. | | | |
|---|---|---|---|
| 5 | 4-Aminophenyl acetic acid | HoPhe | Aad |
| 6 | 4-Aminophenyl acetic acid | Lys38 | Aad |
| 7 | 4-Aminophenyl acetic acid | Lys38 | Aad |
| 8 | 4-Aminophenyl acetic acid | Lys38 | Aad |
| 9 | 4-Aminophenyl acetic acid | Lys38 | Aad |

| No. | $X_3$ | $X_4$ | $Y_1$ |
|---|---|---|---|
| 1 | Nle | Aad | |
| 2 | Acpc | Aad | |
| 3 | Acpc | Aad | |

TABLE 14-continued

α4β1 integrin ligands identified from OBOC combinatorial library L-4.

| # | | | |
|---|---|---|---|
| 4 | Nle | Chg | D-Glu |
| 5 | D-Nal-2 | D-Glu | |
| 6 | D-Phe | 4-Pal | D-Asn |
| 7 | D-Phe | D-Asp | |
| 8 | D-Phe | D-Ser | Nva |
| 9 | D-Phe | D-Val | |

The ligands identified from this library have the following features: (1) hydrophobic amino acids such as leucine, leucine analogs (i.e., Nle, Cpa), and phenylalanine analogs (i.e., HoPhe), and lysine derivatives such as Lys38 are preferred at position $X_1$; (2) the negatively charged amino acid Aad is preferred at position $X_2$; (3) hydrophobic amino acids such as Nle, Acpc, and D-Phe are preferred at position $X_3$; and (4) D-amino acids and negatively charged amino acids are preferred at position $X_4$.

Example 6

Ligands Identified from OBOC Combinatorial Library L-5

The fifth OBOC combinatorial peptidomimetic library (L-5) was also synthesized by replacing the various substituents of BIO-1211 with small organic groups such as isocyanates, unnatural amino acids, and naturally-occurring amino acids. More particularly, the library contained compounds having the following structure:

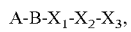

wherein A is a 2-(methylphenyl)ureido group; B is either 4-aminophenyl acetic acid or 2-methyl-4-aminophenyl acetic acid; $X_1$ is one of 10 amino acids shown in Table 10; $X_2$ is one of 3 negatively charged amino acids shown in Table 3; and $X_3$ is one of 26 hydrophobic amino acids shown in Table 9.

Figure 11:
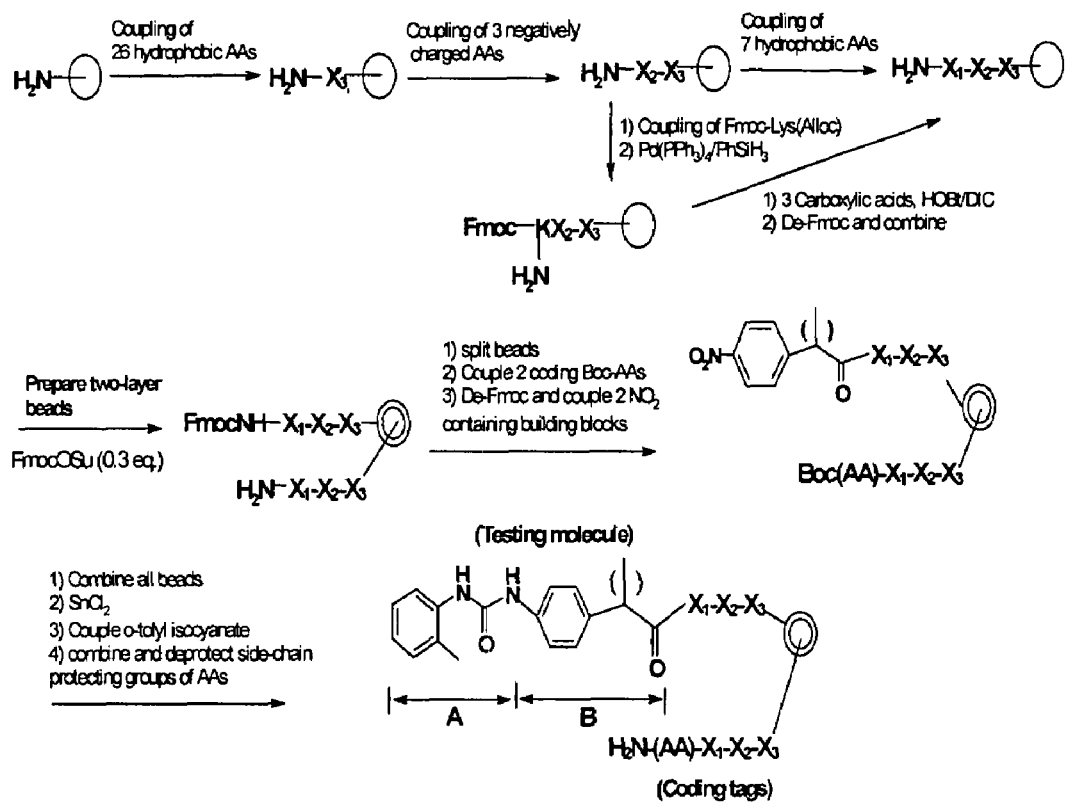
FIG. 11 shows the synthesis of library L-5.

The synthesis of library L-5 is shown in FIG. 11 below. TentaGel beads (1.0 g, loading 0.26 mmol/g) were swollen in DMF (20 mL) for 3 h. The resin was split into 26 equal portions in 26 disposable polypropylene columns with a polyethylene frit. 26 different Fmoc-amino acids (3 equiv.), as shown in Table 9, were separately dissolved in a solution of HOBt (3 equiv.) and DIC (3 equiv.) in DMF and were added into 26 columns, each column receiving only one amino acid. The coupling was carried out at room temperature for 2 h. After filtration, the beads were combined, mixed, and washed three times each with DMF, MeOH, and DMF again. The beads were subjected to Fmoc deprotection with 20% piperidine (5 min, 15 min). After washing with DMF, MeOH, and DMF, the beads were split into three columns and coupled with three negatively charged amino acids (Table 3) in the same manner as above, respectively. The beads were combined and split again into 10 aliquots. 7 aliquots of beads were coupled with 7 individual hydrophobic amino acids shown in Table 10. The remaining 3 aliquots of beads were coupled with Fmoc-Lys(Alloc) followed by Alloc deprotection [(Pd(PPh$_3$)$_4$/PhSiH$_3$] and subsequent acylation with 3 carboxylic acids (the 3 lysine derivatives shown in Table 10) using HOBt/DIC coupling. After coupling, all beads in the 10 columns were mixed prior to Fmoc deprotection with 20% piperidine (5 min, 15 min). The beads with free amine groups were washed with DMF, MeOH, DCM, and thoroughly dried in vacuum.

Two-layer beads were then prepared using the bi-phasic solvent approach described above (Liu et al., supra). Briefly, beads were swollen in water for 2 days. Water was removed by filtration and the solution of Fmoc-OSu (26.3 mg, 0.078 mmol) in DCM/diethyl ether (150 mL, 55/45) was added to the wet beads, followed by addition of DIEA (27 µL, 0.156 mmol). The mixture was shaken vigorously at room temperature for 30 min. After washing with the DCM/diethyl ether mixture three times and with DMF six times to remove water from the beads, the beads were split into 2 aliquots and each aliquot of beads was coupled with one coding Boc-amino acid (i.e., Boc-Val or Boc-Ala). After removal of Fmoc with 20% piperidine, the beads with Boc-Val were coupled with 2-(4-nitrophenyl) propionic acid, and the beads with Boc-Ala were coupled overnight with 4-nitrophenyl acetic acid (10 equiv. to resin) using a HOBt/DIC coupling method. The beads were combined and treated with 2M SnCl$_2$ in DMF for 2 h (twice) to reduce the NO$_2$ group. The beads were then coupled overnight with O-tolylisocyanate (10 equiv.) at room temperature. After washing with DMF, methanol, and DCM, the beads were then dried under vacuum for 1 h. Side-chain deprotection was achieved using a mixture of 82.5% TFA:5% phenol:5% thioanisole:5% water:2.5% TIS. After neutralization with 2% DIEA/DMF (twice), the resin was washed sequentially with DMF, MeOH, DCM, DMF, DMF/water, water, and PBS. The bead library was stored in PBS/0.05% sodium azide. The outer layer of the beads contained the library compounds and the inner core contained the coding tags that could be decoded by microsequencing as previously described (Liu et al., supra).

Figure 2:
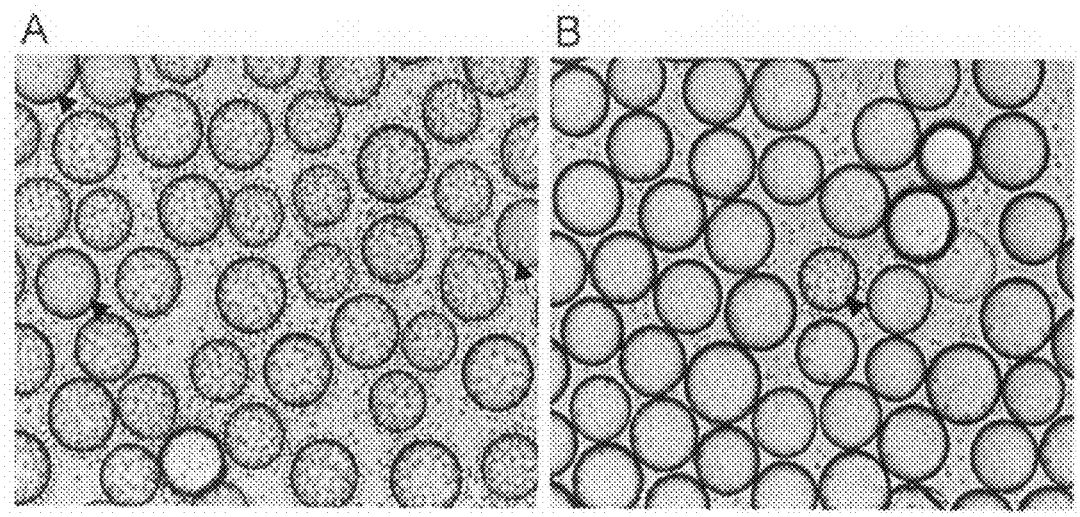
FIG. 2 shows the competitive OBOC cell screening of library L-5 for $\alpha_4\beta_1$ integrin. The bead library was screened against Jurkat cells at low stringency (FIG. 2A) without competitors or at high stringency with competitors (FIG. 2B). Low-affinity conditions resulted in only a few beads not adhering to cells (arrows in FIG. 2A). Conversely, in the presence of soluble binding competitors, only beads with high-affinity ligands bound Jurkat cells (arrow in FIG. 2B).

This library was screened using a competitive cell-based screening method with high stringency so that only those ligands with very high affinity to $\alpha_4\beta_1$ integrin are coated by a layer of lymphoma cells (FIG. 2). To achieve this, an increasing amount of known $\alpha_4\beta_1$ antagonist was incorporated into the screening solution, which competed with the interaction between cell surface $\alpha_4\beta_1$ integrin and the immobilized library compounds on the bead surface, until a limited number of positive beads were detected in the library. Library L-5, which comprised approximately 75,000 beads corresponding to 1560 permutations, was screened against live Jurkat cells ($\alpha_4\beta_1$ integrin-positive) ($3\times10^5$/ml) in complete RPMI medium containing 500 µM BIO-1211 in solution. While 500 µM BIO-1211 was used to screen the library, the concentration of soluble BIO-1211 required to completely eliminate Jurkat cell binding to BIO-1211-beads (positive control) was only 10 µM, 50 times lower than that used in these library screening experiments. Twenty beads were isolated under these high stringency conditions. Guanidine HCl (8 M) was used to strip the beads of all cells and proteins. The recovered beads were then retested with normal peripheral blood lymphocytes. Beads that bound preferentially to Jurkat cells but not to normal lymphocytes were sequenced. A total of twelve true positive beads were isolated and decoded, which represented 6 independent ligands. These ligands are set forth in Table 15 below. All of the identified ligands have the following structure:

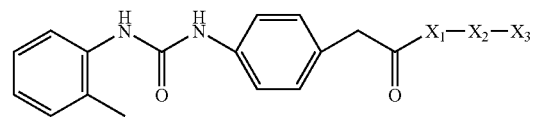

wherein $X_1$, $X_2$, and $X_3$ are the same as defined above. As such, the results showed that a 4-aminophenyl acetyl group is the preferred substituent at position B, as all ligands contained this particular group at that position. The remaining positions contained various combinations of naturally-occurring amino acids, unnatural amino acids, and/or D-amino acids that differed significantly from the naturally-occurring amino acids found in BIO-1211.

TABLE 15

α₄β₁ integrin ligands identified from OBOC combinatorial library L-5.

| No. | Name | B | X₁ |
|---|---|---|---|
| I-1 | | 4-Aminophenyl acetic acid | Lys38 |
| I-2 | Ligand 2A | 4-Aminophenyl acetic acid | Lys38 |
| II-1 | | 4-Aminophenyl acetic acid | Lys38 |
| II-2 | | 4-Aminophenyl acetic acid | Lys38 |
| III-1 | | 4-Aminophenyl acetic acid | Lys38 |
| III-2 | | 4-Aminophenyl acetic acid | Lys38 |

| No. | X₂ | X₃ |
|---|---|---|
| I-1 | Aad | D-Phe |

TABLE 15-continued $\alpha_4\beta_1$ integrin ligands identified from OBOC combinatorial library L-5.

| | | |
|---|---|---|
| I-2 | Aad | Ach |
| II-1 | Aad | D-Nal-2 |
| II-2 | Aad | Ile |
| III-1 | Aad | Val |
| III-2 | Aad | Leu |

Figure 3:
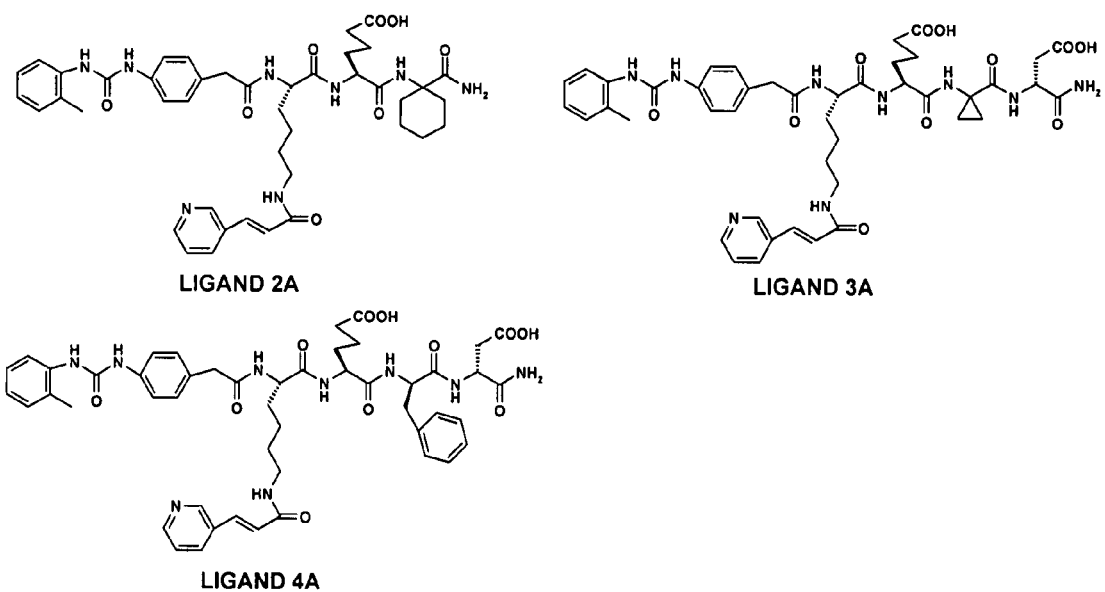
FIG. 3 shows the structures of ligand 2A, ligand 3A, and ligand 4A.

A cell-based $\alpha_4\beta_1$-mediated adhesion assay with immobilized CS-1 peptide was used to determine the binding affinity of these ligands to Jurkat cells. CS-1 is a 25 amino acid linear peptide of fibronectin responsible for the $\alpha_4\beta_1$ interaction. The cell adhesion assay was performed as follows: 96-well plates were coated with 1 μg/ml neutravidin, followed by biotin conjugated CS-1 peptides after washing. The wells were blocked with 1% bovine serum albumin in phosphate buffered saline. Jurkat cells with serial dilutions of tested ligands in 100 μl binding buffer (TBS, 1 mM $Mn^{2+}$) were added and allowed to bind for 30 min. Unbound cells were removed by gentle washing. Bound cells were fixed with 3.7% formaldehyde and stained with 0.1% crystal violet. The dye was dissolved in 1% SDS, and recorded on a 96-well plate reader at 570 nm. $IC_{50}$ data were calculated from inhibition curves resulting from the concentration-dependent inhibition. This assay demonstrated that the $IC_{50}$ of BIO-1211 was 0.2 nM, whereas the $IC_{50}$ of ligand 2A was 2 μM, 100 fold better than BIO-1211. The structure of ligand 2A is shown in FIG. 3.

Figure 4:
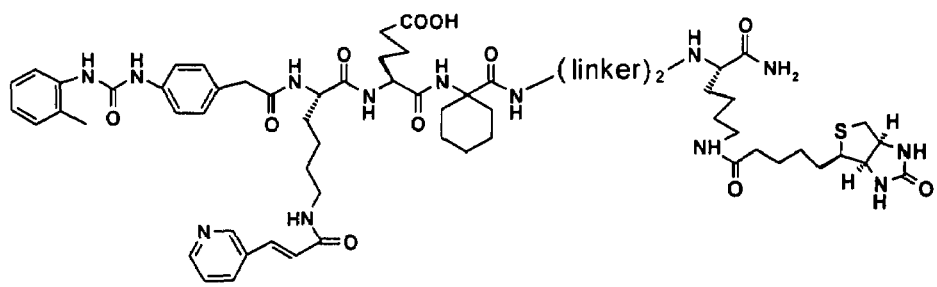
FIG. 4 shows the structures of biotinylated ligand 2A and biotinylated ligand 3A.
Figure 4:
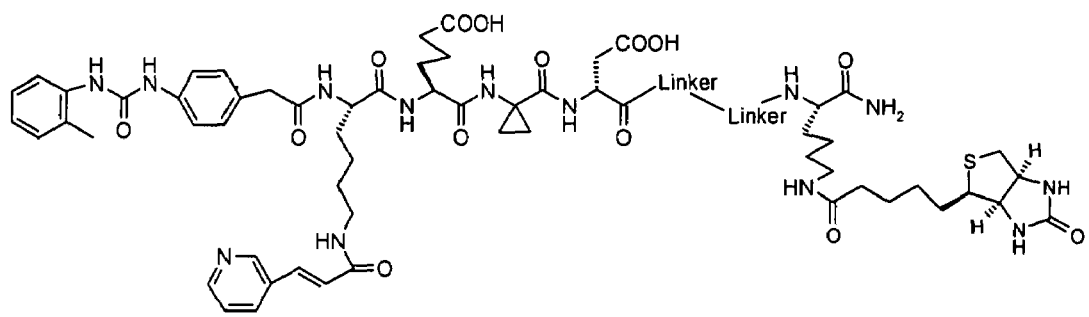
Figure 4:
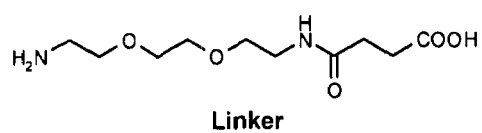
Figure 5:
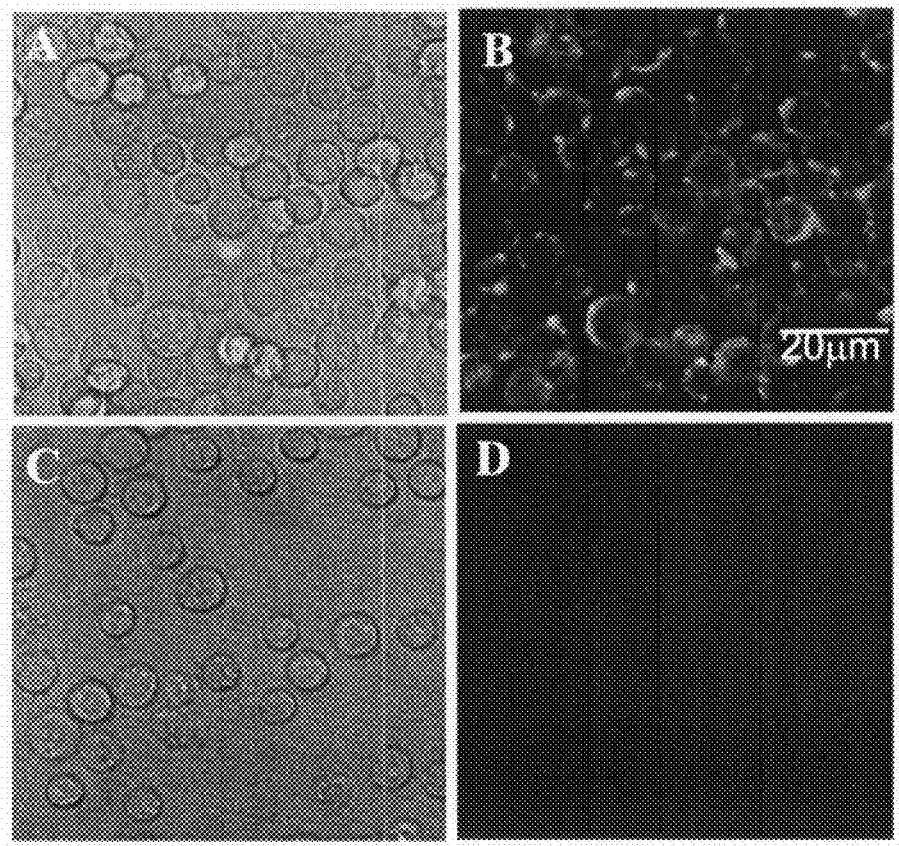
FIG. 5 shows an in vitro binding assay of ligand 2A with cultured cells. Epifluorescence microscope images of $\alpha_4\beta_1$-positive Molt-4 cells (FIG. 5B) and $\alpha_4\beta_1$-negative A549 cells (FIG. 5D) incubated with 10 nM biotinylated ligand 2A conjugate followed by streptavidin-Qdot605 show that a fluorescence signal was only detected on Molt-4 cells, demonstrating the specific targeting of ligand 2A to the $\alpha_4\beta_1$ integrin receptor. White field images of Molt-4 cells (FIG. 5A) and A549 cells (FIG. 5C) are also shown.

The tumor targeting potential of ligand 2A was first evaluated for binding to $\alpha_4\beta_1$ positive tumor cell lines, such as T-lymphoid leukemia cells (Jurkat, Molt-4, etc.). A ligand 2A-Qdot complex was prepared by incubating biotinylated ligand 2A (FIG. 4) with streptavidin-Qdot605 (Quantum Dot Corp.; Hayward, Calif.) at a molar ratio of 5:1 for 1 h. In cell staining assays, Molt-4 cells ($\alpha_4\beta_1$-positive) and trypsinized A549 cells ($\alpha_4\beta_1$-negative) were incubated with the prepared ligand 2A-Qdot complex (10 nM) for 30 minutes in RPMI medium, washed, and examined using an inverted Olympus microscope (IX70) (FIG. 5). Fluorescent microscopy confirmed strong and specific binding to Molt-4 cells ($\alpha_4\beta_1$-positive), but no staining was observed on A549 non-small cell lung cancer cells ($\alpha_4\beta_1$-negative).

In vivo optical imaging studies of mouse xenografts were used to investigate the lymphoma targeting efficiency of ligand 2A in live animals. The near infrared imaging probe was prepared by pre-incubating biotinylated ligand 2A with streptavidin-Alexa680 (Molecular Probes; Eugene, Oreg.) at a molar ratio of 5:1 for 1 h at 4° C. After confirmation of binding with an in vitro cell-binding assay, the ligand 2A-Alexa 680 conjugate was injected into the tail vein of nude mice bearing human subcutaneous xenografts with Molt-4 T-leukemia ($\alpha_4\beta_1$-positive) over one shoulder and A549 non-small cell lung cancer ($\alpha_4\beta_1$-negative) over the other. The xenografts were prepared by subcutaneously injecting about $5\times10^6$ Molt-4 cells into one shoulder of nude mice and about $2\times10^6$ A549 cells into the other shoulder. Tumors measured about 0.5-1.0 cm in diameter at the time of imaging.

Animals (n=4) were injected with the ligand 2A-Alexa 680 probe through the tail vein at a dosage of 1.7 nmol 24 hours prior to imaging. Negative control animals (n=3) received an unrelated peptide-Alexa Fluor680 probe in the same manner. The unrelated peptide had the following sequence: TPN-NEIDSFVKSGDF (SEQ ID NO: 1). Animals were anesthetized by using intrapertitoneal injection of pentobarbital (60 mg/kg of body weight). Imaging was performed using Kodak multimodal imaging system IS2000MM (Kodak; Rochester, N.Y.) equipped with an excitation bandpass filter at 625 nm and an emission at 700 nm. Exposure time was 30 seconds per image. Images were analyzed using the imaging station IS2000MM provided software (Kodak ID Image Analysis Software; Kodak). After in vivo imaging, animal were euthanized by $CO_2$ overdose. Tumors, organs, and muscle tissue were excised and imaged with IS2000MM as described above.

Figure 6:
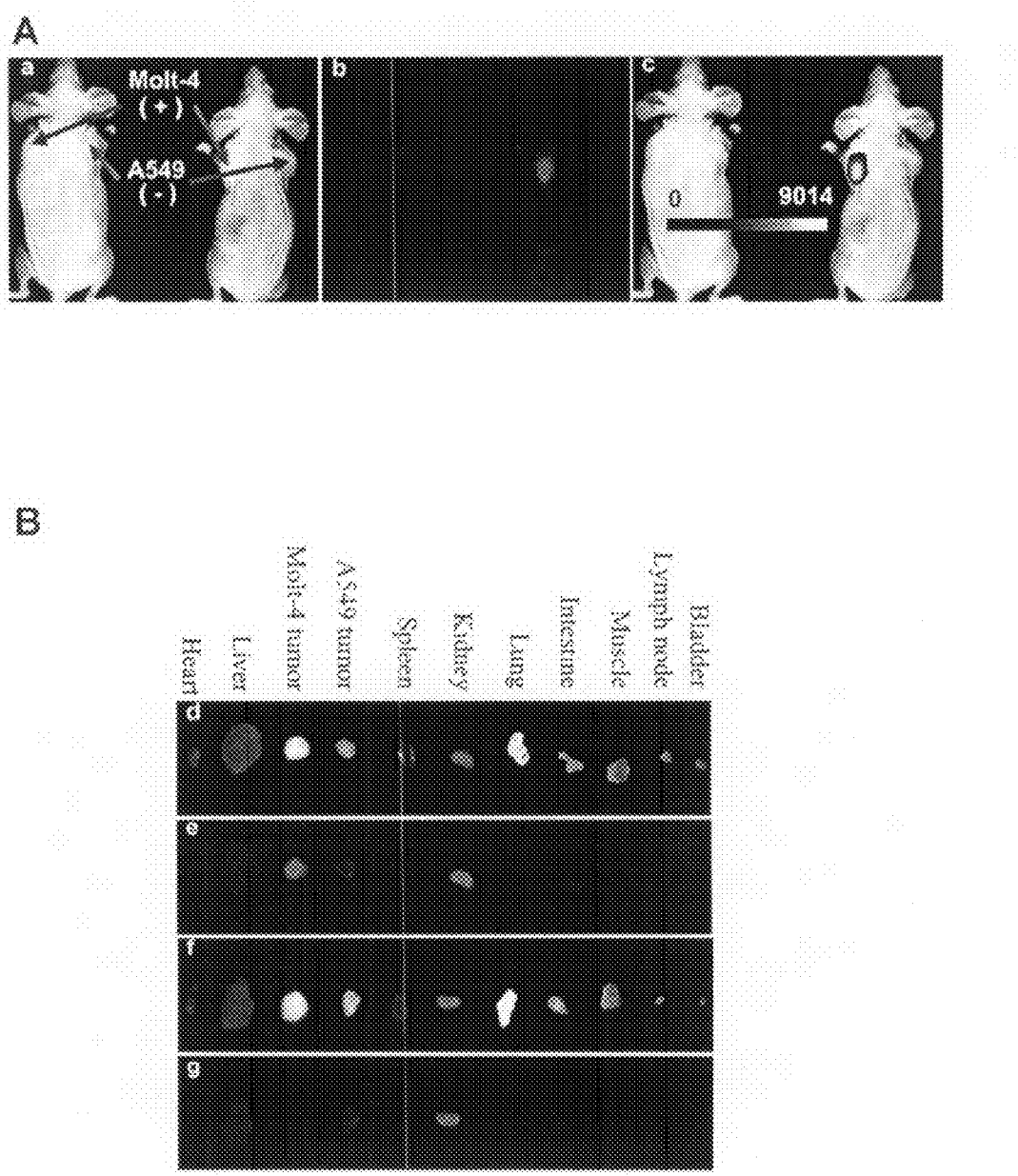
FIG. 6A shows near-infrared fluorescence (NIRF) images of mice bearing bilateral $\alpha_4\beta_1$-positive (Molt-4) and negative (A549) tumors. Imaging was performed 24 hours after intravenous injection of the ligand 2A-Alexa680 probe (right mouse) or an unrelated peptide-Alexa680 probe (left mouse). (a) White light image; (b) NIRF image; (c) superimposed image of white light image and color-encoded NIRF signals. A strong fluorescence signal was observed in the Molt-4 tumor and insignificant uptake was observed in the A549 tumor following administration of the ligand 2A imaging probe (right mouse). A control mouse on the left was injected with the unrelated peptide-Alexa680 probe at a similar dosage and showed no localized fluorescence signals.
FIG. 6B shows white light (d, f) and NIRF (e, g) images of excised tumors, organs, and tissues. Mice administered with the ligand 2A-Alexa680 probe (d, e) or the unrelated peptide-Alexa680 probe (f, g) were dissected immediately after in vivo imaging. The Molt-4 tumor (e) revealed significantly higher fluorescence signal compared with the A549 tumor, organs, and tissues. A control mouse showed no uptake in the Molt-4 tumor (g). The signal in the kidneys indicated that the fluorescence complexes were cleared mainly through renal elimination.

Whole-body in vivo imaging studies demonstrated that a high-intensity near-infrared signal was obtained from the Molt-4 tumor, whereas no signal was observed from the negative control A549 tumor (FIG. 6A). The specific accumulation of the ligand 2A-Alexa 680 probe in Molt-4 tumors was further confirmed with ex vivo imaging of excised tumors and organs from the mice (FIG. 6B). Control experiments using a probe containing the unrelated linear peptide showed no uptake to either tumor. Transient kidney uptake was seen in both experiments.

The example shows that the OBOC combinatorial library approach can be used to rapidly screen about 75,000 peptidomimetic-beads and identify ligands that are 50-100 fold better than some of the best B I-integrin ligands reported in the literature. These peptidomimetic ligands not only can be used as targeting agents for cancer, but may also be used as potent $\alpha_4\beta_1$-integrin antagonists for the treatment of autoimmune and inflammatory diseases. Similar approaches can also be readily applied to the screening of ligands or inhibitors for a variety of drug targets.

Example 7

Acute Lymphocytic Leukemia Cell-Specific Ligands Identified from Library L-2

OBOC combinatorial library L-2 was screened against leukemia cells obtained from a patient having acute lymphocytic leukemia (ALL). The screen was independently performed on ALL cells obtained from two patients, and Table 16 shows the ligands identified from patient 1 (Group I ligands) and patient 2 (Group II ligands). These ligands bound with high affinity to ALL cells but not to normal (i.e., non-leukemia) cells. Ligand II-3=SEQ ID NO:5.

TABLE 16

ALL cell-specific ligands identified from library L-2.

| No. | B | $X_1$ |
|---|---|---|
| I-1 | 4-Aminophenyl acetic acid 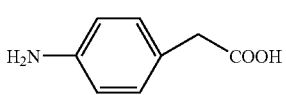 | HoPhe 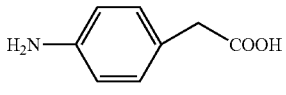 |
| I-2 | 4-Aminophenyl acetic acid | Hle |
| I-3 | 2-(4-Aminophenyl) propionic acid | Cpa |
| I-4 | 4-Aminophenyl acetic acid | Cha |

TABLE 16-continued

ALL cell-specific ligands identified from library L-2.

| | | |
|---|---|---|
| I-5 | 2-(4-Aminophenyl) propionic acid | Cha |
| I-6 | 4-Aminophenyl acetic acid | Lys12 |
| I-7 | 2-(4-Aminophenyl) propionic acid | Hle |
| I-8 | 2-(4-Aminophenyl) propionic acid | Cpa |
| I-9 | 4-Aminophenyl acetic acid | Cha |
| I-10 | 4-Aminophenyl acetic acid | Leu |
| I-11 | 4-Aminophenyl acetic acid | Leu |
| I-12 | 4-Aminophenyl acetic acid | Nle |

TABLE 16-continued

ALL cell-specific ligands identified from library L-2.

| | | |
|---|---|---|
| I-13 | 4-Aminophenyl acetic acid | Cpa |
| I-14 | 2-(4-Aminophenyl) propionic acid | Hle |
| I-15 | 4-Aminophenyl acetic acid | Nle |
| I-16 | 2-(4-Aminophenyl) propionic acid | Ile |
| I-17 | 2-(4-Aminophenyl) propionic acid | HoPhe |
| I-18 | 4-Aminophenyl acetic acid | Hle |
| II-1 | 4-Aminophenyl acetic acid | Leu |
| II-2 | 2-(4-Aminophenyl) propionic acid | HoPhe |

TABLE 16-continued

ALL cell-specific ligands identified from library L-2.

| II-3 | 2-(4-Aminophenyl)propionic acid | Nle |
| II-4 | 2-(4-Aminophenyl)propionic acid | Cpa |

| No. | X$_2$ | X$_3$ | X$_4$ |
|---|---|---|---|
| I-1 | Asp | Phg | Pro |
| I-2 | Asp | Ile | Pro |
| I-3 | Asp | Ile | Hyp |
| I-4 | Asp | Pra | Pro |
| I-5 | Asp | Leu | Hyp |
| I-6 | Aad | Nva | Hyp |
| I-7 | Asp | Val | Pro |

TABLE 16-continued
ALL cell-specific ligands identified from library L-2.
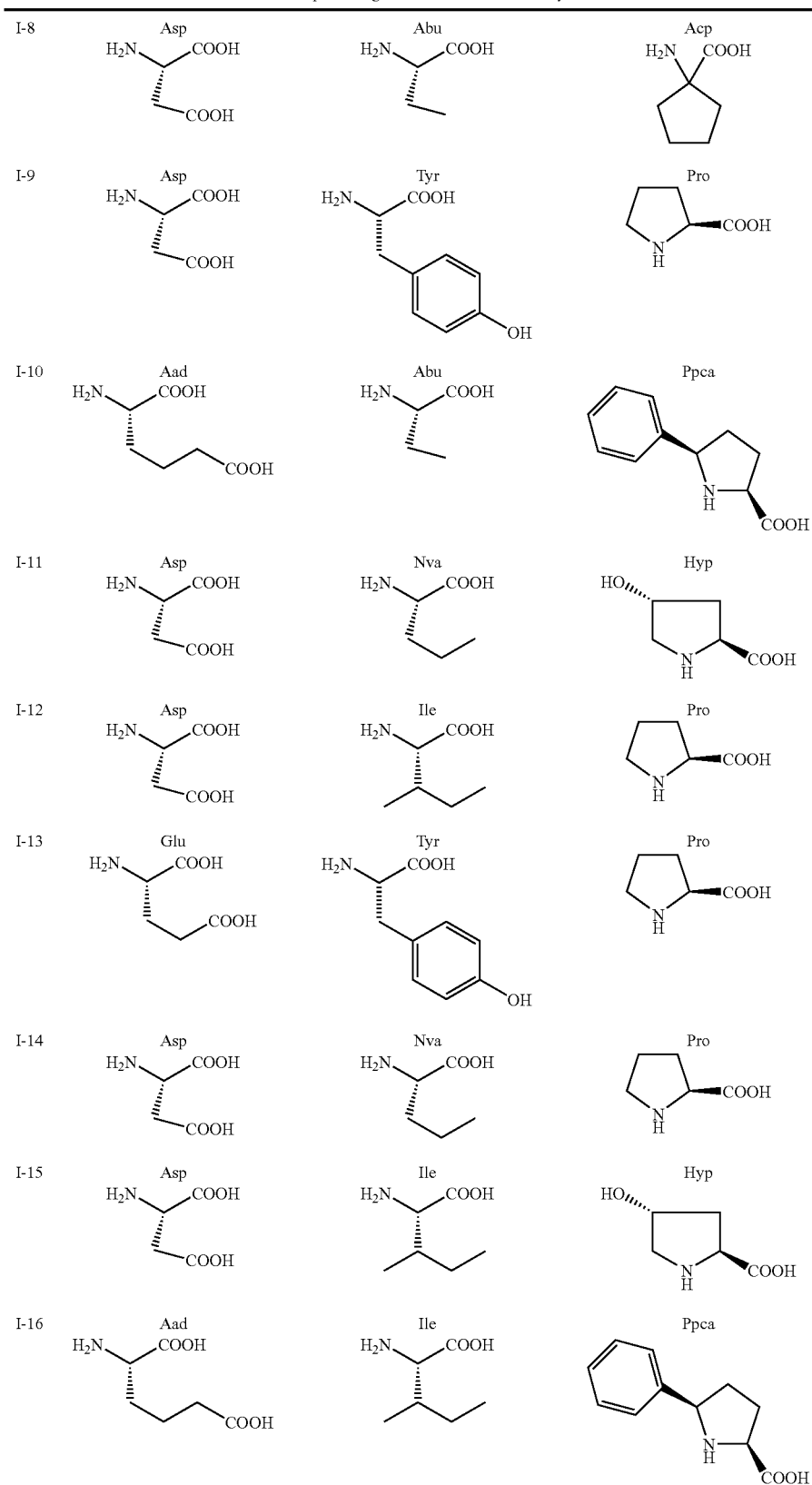

TABLE 16-continued
ALL cell-specific ligands identified from library L-2.
| No. | X3 | X4 | X5 |
|---|---|---|---|
| I-17 | Asp 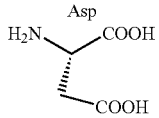 | Ala 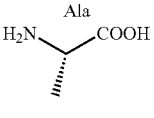 | Pro 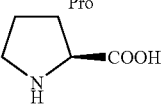 |
| I-18 | Glu 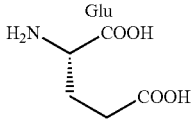 | Abu 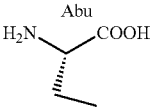 | Hyp 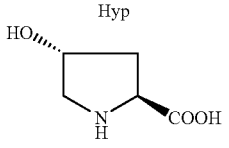 |
| II-1 | Asp 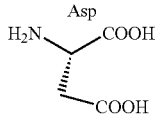 | Leu 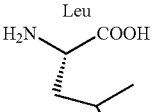 | Ppca 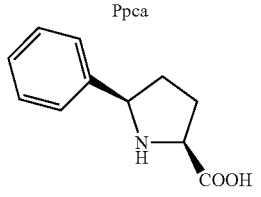 |
| II-2 | Asp 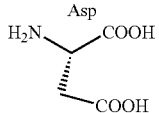 | Nva 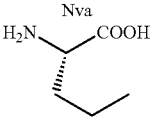 | Ppca 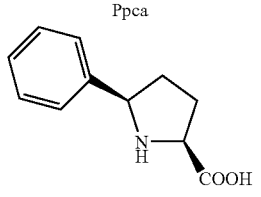 |
| II-3 | Asp 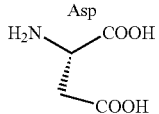 | Val 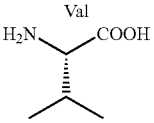 | Pro 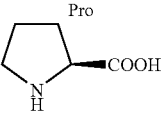 |
| II-4 | Aad 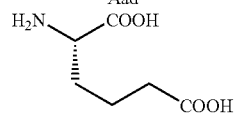 | Abu 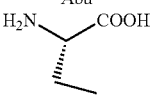 | Pro 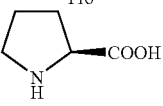 |
| No. | $X_5$ | $Y_1$ | $Y_2$ |
|---|---|---|---|
| I-1 | Gly 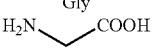 | D-Tyr 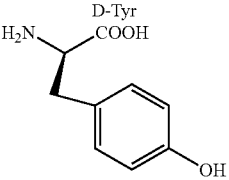 | Aad 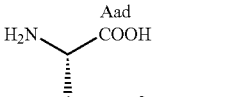 |
| I-2 | Chg 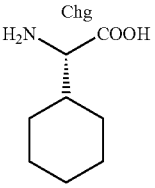 | | |
| I-3 | D-Thr 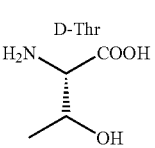 | D-Asn 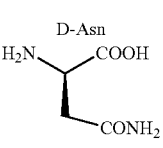 | Nva 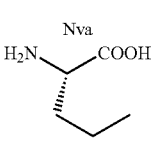 |

TABLE 16-continued
ALL cell-specific ligands identified from library L-2.
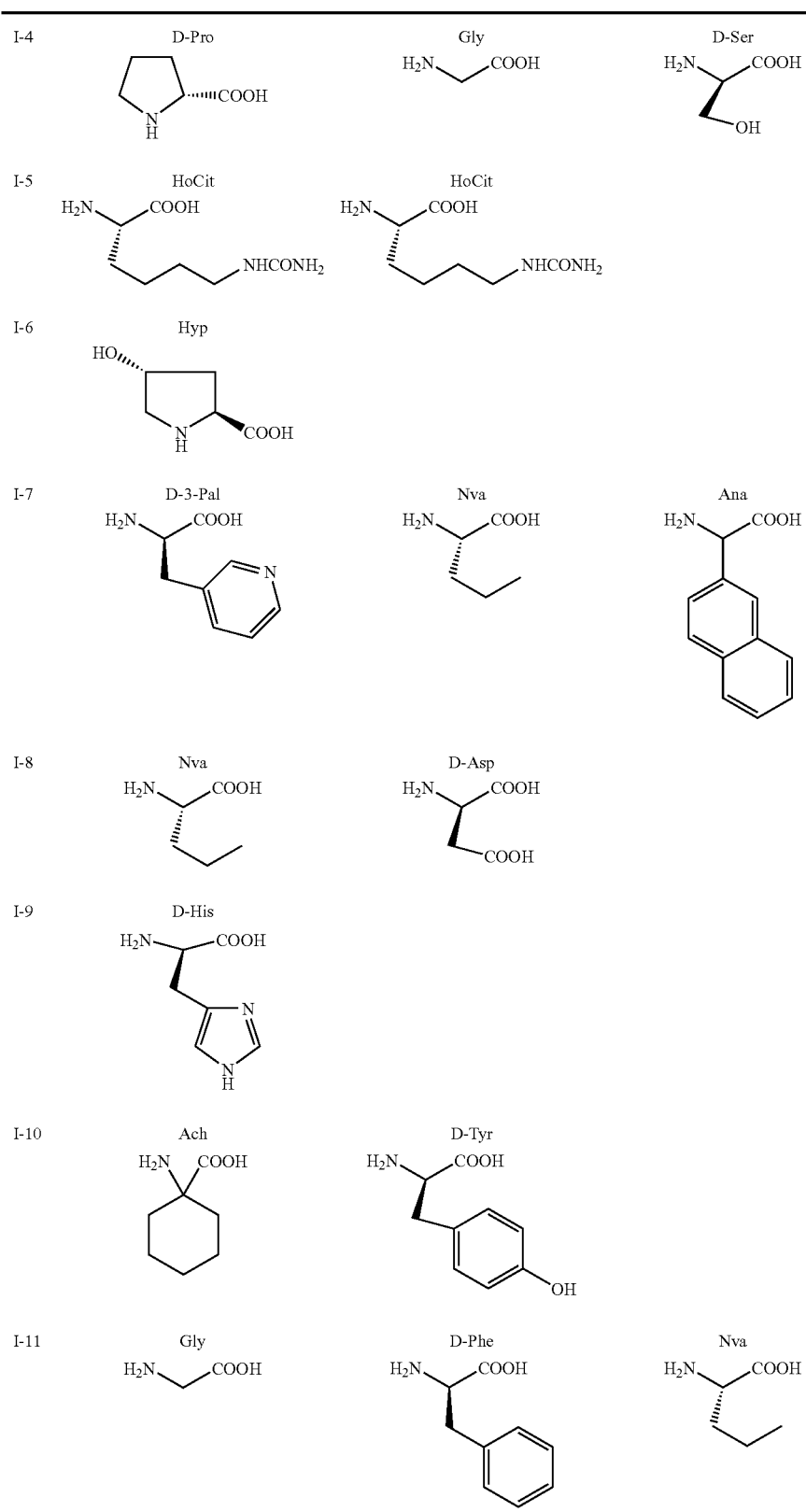

TABLE 16-continued
ALL cell-specific ligands identified from library L-2.
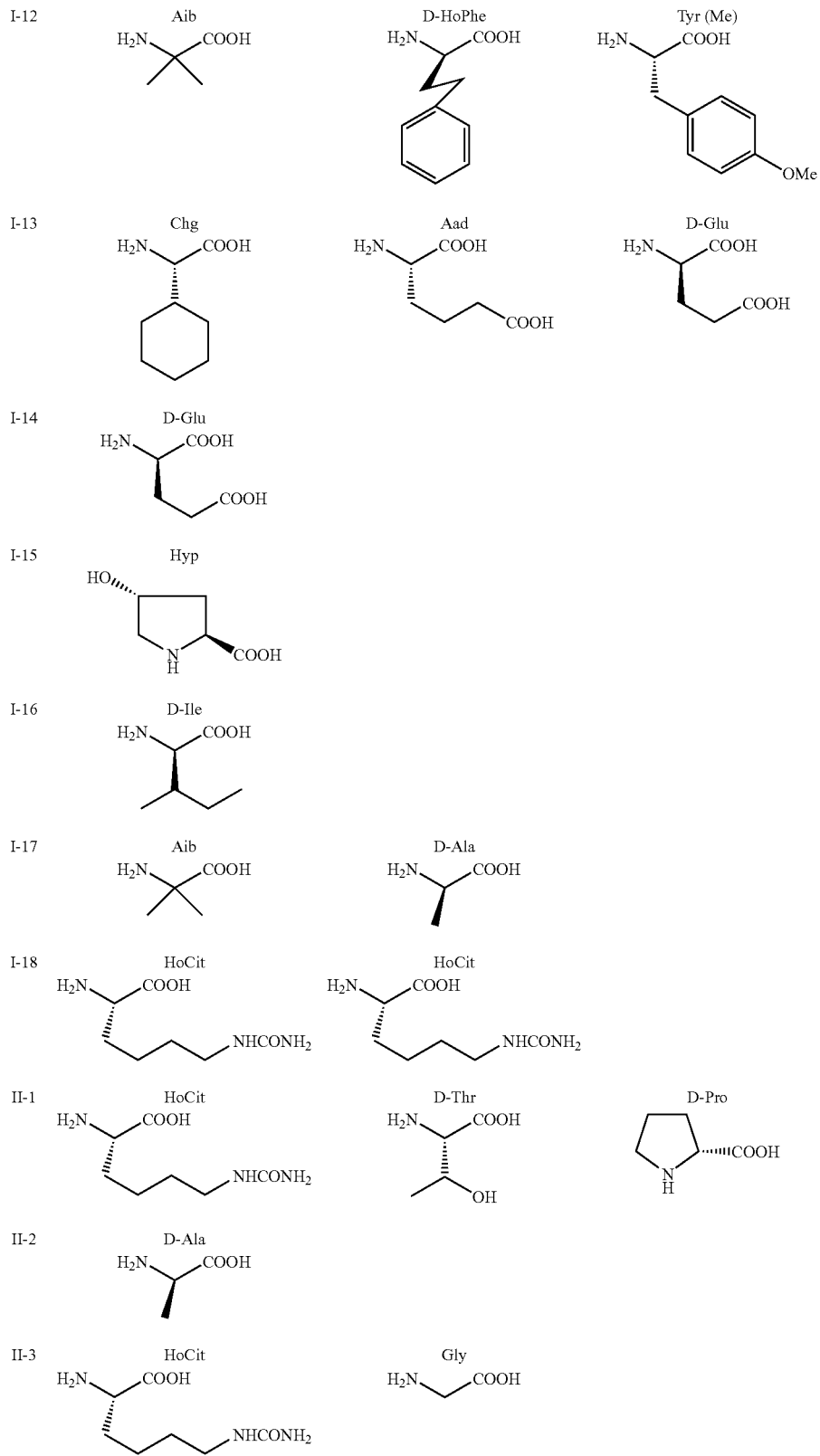

TABLE 16-continued

ALL cell-specific ligands identified from library L-2.

| | | | |
|---|---|---|---|
| II-4 | D-Ala | D-Tyr | D-Phe(4-Me) |

The ligands identified from this library have the following features: (1) hydrophobic amino acids such as leucine, leucine analogs (i.e., Nle, Hle, Cha, Cpa), and phenylalanine analogs (i.e., HoPhe), and lysine derivatives such as Lys12 are preferred at position $X_1$; (2) negatively charged amino acids such as Aad, Asp, and Glu are preferred at position $X_2$; (3) hydrophobic amino acids such as isoleucine, valine, valine analogs (i.e., Nva), and Abu are preferred at position $X_3$; (4) proline and its analogs (i.e., Hyp, Ppca) are preferred at position $X_4$; and (5) D-amino acids are preferred at positions $X_5$, $Y_1$, and $Y_2$.

Example 8

Acute Lymphocytic Leukemia Cell-Specific Ligands Identified from Libraries L-3 and L-4

OBOC combinatorial libraries L-3 and L-4 were screened against leukemia cells obtained from a patient having acute lymphocytic leukemia (ALL). Table 17 shows the ligands identified from the patient using either library L-3 (Group III ligands) or library L-4 (Group IV ligand). These ligands bound with high affinity to ALL cells but not to normal (i.e., non-leukemia) cells.

TABLE 17

ALL cell-specific ligands identified from libraries L-3 and L-4.

| No. | B | $X_1$ | $X_2$ |
|---|---|---|---|
| III-1 | 2-(4-Aminophenyl) propionic acid | Nle | Glu |
| III-2 | 4-Aminophenyl acetic acid | Cha | Asp |
| III-3 | 2-(4-Aminophenyl) propionic acid | Hle | Aad |
| III-4 | 4-Aminophenyl acetic acid | Leu | Asp |

TABLE 17-continued

ALL cell-specific ligands identified from libraries L-3 and L-4.

| | | | |
|---|---|---|---|
| III-5 | 2-(4-Aminophenyl) propionic acid | Cpa | Asp |
| III-6 | 2-(4-Aminophenyl) propionic acid | HoPhe | Asp |
| III-7 | 4-Aminophenyl acetic acid | Cha | Aad |
| III-8 | 4-Aminophenyl acetic acid | Hle | Asp |
| III-9 | 2-(4-Aminophenyl) propionic acid | Leu | Aad |
| III-10 | 4-Aminophenyl acetic acid | Lys38 | Asp |
| III-11 | 2-(4-Aminophenyl) propionic acid | Lys12 | Asp |
| III-12 | 2-(4-Aminophenyl) propionic acid | Lys38 | Aad |

TABLE 17-continued

ALL cell-specific ligands identified from libraries L-3 and L-4.

| No. | | | |
|---|---|---|---|
| III-13 | 4-Aminophenyl acetic acid | Cpa | Asp |
| III-14 | 4-Aminophenyl acetic acid | HoPhe | Asp |
| IV-1 | 2-(4-Aminophenyl) propionic acid | Nle | Aad |

| No. | X₃ | X₄ | Y₁ |
|---|---|---|---|
| III-1 | Ala | D-Thi | |
| III-2 | Nle | D-Gln | |
| III-3 | Ile | D-Asp | D-Phe |
| III-4 | D-Phe | Aic | |
| III-5 | Leu | D-Thi | |

TABLE 17-continued

ALL cell-specific ligands identified from libraries L-3 and L-4.

| III-6 | Abu | D-Asn | |
| III-7 | Val | Ana | Ahch |
| III-8 | Acpc | D-Ala | |
| III-9 | Ana | D-Pro | |
| III-10 | Phe(3-Cl) | D-Pro | |
| III-11 | Nle | Hyp | D-Glu |
| III-12 | D-Nal-2 | D-Thr | D-Bpa |
| III-13 | Ala | D-Thi | |

TABLE 17-continued

ALL cell-specific ligands identified from libraries L-3 and L-4.

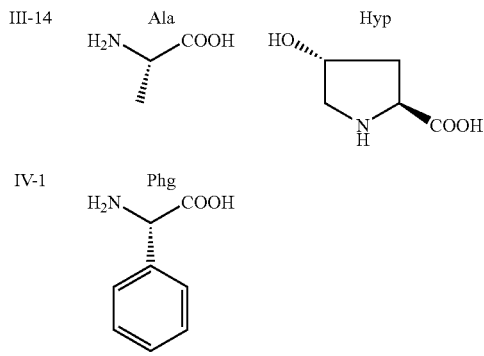

The ligands identified from this library have the following features: (1) hydrophobic amino acids such as leucine, leucine analogs (i.e., Nle, Hle, Cha, Cpa), and phenylalanine analogs (i.e., HoPhe), and lysine derivatives such as Lys12 and Lys38 are preferred at position $X_1$; (2) negatively charged amino acids such as Aad, Asp, and Glu are preferred at position $X_2$; (3) hydrophobic amino acids are preferred at position $X_3$; and (4) D-amino acids are preferred at position $X_4$.

Example 9

Binding Affinities of the OBOC Ligands 32 ligands were re-synthesized in solution for biological assays (Tables 18 and 19). Among them, 16 ligands with a 4-aminophenyl acetyl group at position B (Group A ligands) and 16 ligands with a 2-methyl-4-aminophenyl acetyl group at position B (Group B ligands) were synthesized. The majority of these ligands were synthesized with a C-terminal amide group (Table 18), although 4 ligands (i.e., ligands 12A, 12B, 13A, and 13B) were synthesized with a C-terminal carboxylic acid group (Table 19).

TABLE 18

The structures of the re-synthesized ligands with a C-terminal amide group.

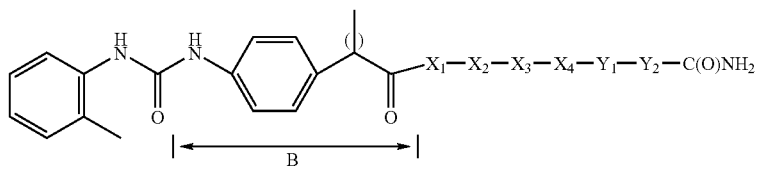

| No. | Name | B | $X_1$ | $X_2$ |
|---|---|---|---|---|
| 1A | | 4-Aminophenyl acetic acid | Lys38 | Aad |
| 1B | | 2-(4-Aminophenyl) propionic acid | Lys38 | Aad |

TABLE 18-continued

The structures of the re-synthesized ligands with a C-terminal amide group.

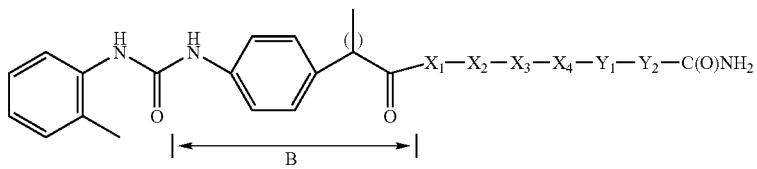

| | | | | |
|---|---|---|---|---|
| 2A | Ligand 2A | 4-Aminophenyl acetic acid | Lys38 | Aad |
| 2B | | 2-(4-Aminophenyl) propionic acid | Lys38 | Aad |
| 3A | Ligand 3A | 4-Aminophenyl acetic acid | Lys38 | Aad |
| 3B | | 2-(4-Aminophenyl) propionic acid | Lys38 | Aad |
| 4A | Ligand 4A | 4-Aminophenyl acetic acid | Lys38 | Aad |
| 4B | | 2-(4-Aminophenyl) propionic acid | Lys38 | Aad |
| 5A | | 4-Aminophenyl acetic acid | Lys38 | Aad |

TABLE 18-continued

The structures of the re-synthesized ligands with a C-terminal amide group.

| | | | |
|---|---|---|---|
| 5B | 2-(4-Aminophenyl) propionic acid | Lys38 | Aad |
| 6A | 4-Aminophenyl acetic acid | HoPhe | Aad |
| 6B | 2-(4-Aminophenyl) propionic acid | HoPhe | Aad |
| 7A | 4-Aminophenyl acetic acid | Lys38 | Aad |
| 7B | 2-(4-Aminophenyl) propionic acid | Lys38 | Aad |
| 8A | 4-Aminophenyl acetic acid | Nle | Aad |
| 8B | 2-(4-Aminophenyl) propionic acid | Nle | Aad |

TABLE 18-continued
The structures of the re-synthesized ligands with a C-terminal amide group.
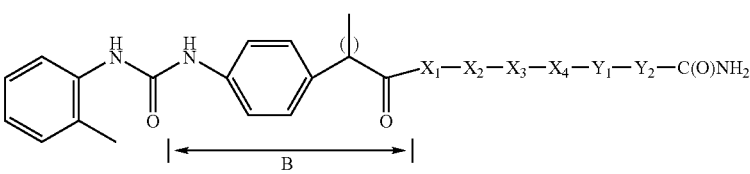

TABLE 18-continued

The structures of the re-synthesized ligands with a C-terminal amide group.

| No. | Name | X₃ | X₄ | Y₁ | Y₂ |
|---|---|---|---|---|---|
| 14B | 2-(4-Aminophenyl) propionic acid | | | Lys38 | Aad |
| 15A | 4-Aminophenyl acetic acid | | | Lys38 | Aad |
| 15B | 2-(4-Aminophenyl) propionic acid | | | Lys38 | Aad |
| 16A | 4-Aminophenyl acetic acid | | | Lys38 | Aad |
| 16B | 2-(4-Aminophenyl) propionic acid | | | Lys38 | Aad |
| 1A | D-Phe | | | | |

TABLE 18-continued
The structures of the re-synthesized ligands with a C-terminal amide group.
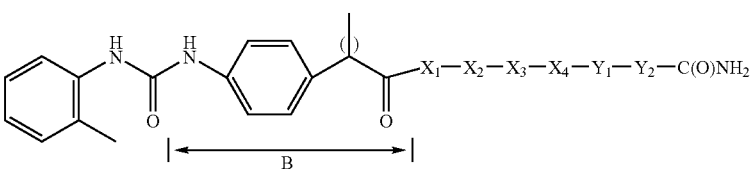
| | | | |
|---|---|---|---|
| 1B | | D-Phe<br>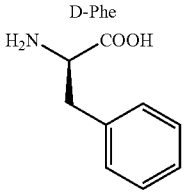 | |
| 2A | Ligand<br>2A | Ach<br>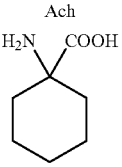 | |
| 2B | | Ach<br>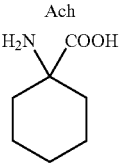 | |
| 3A | Ligand<br>3A | Acpc<br>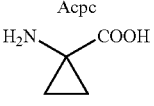 | D-Asp<br>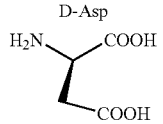 |
| 3B | | Acpc<br>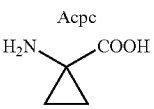 | D-Asp<br>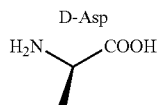 |
| 4A | Ligand | D-Phe<br>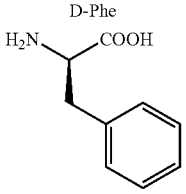 | D-Asp<br>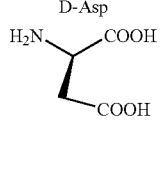 |
| 4B | | D-Phe<br>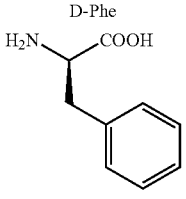 | D-Asp<br>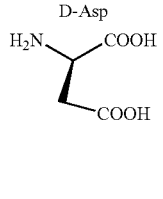 |

TABLE 18-continued
The structures of the re-synthesized ligands with a C-terminal amide group.
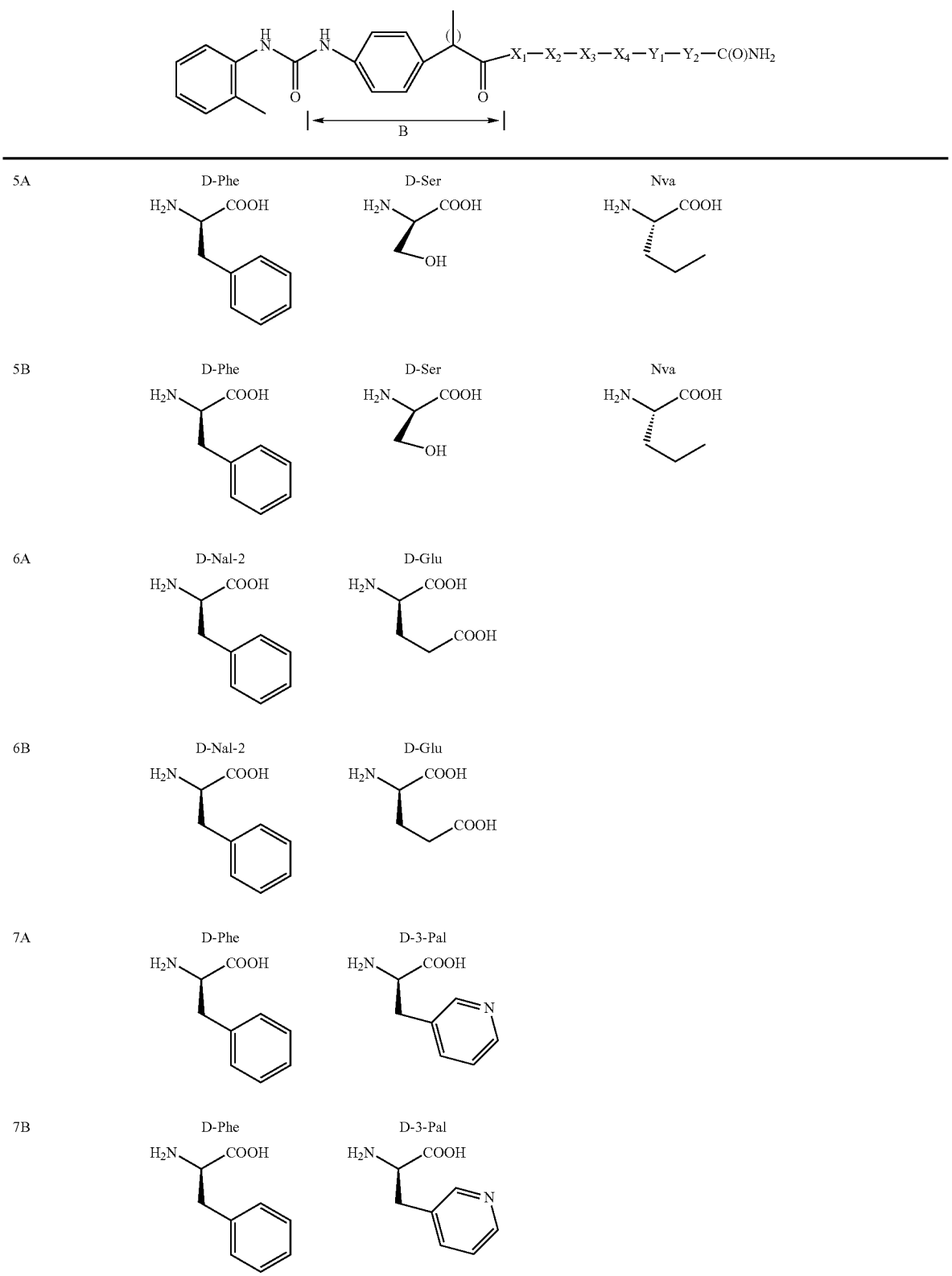

TABLE 18-continued
The structures of the re-synthesized ligands with a C-terminal amide group.
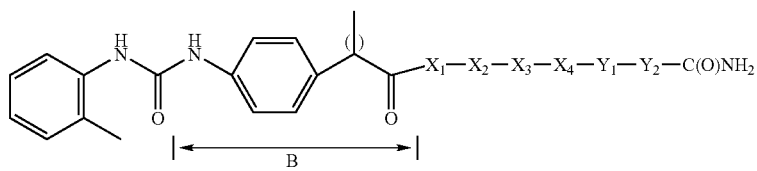
| 8A | Cha | D-Glu | | |
|---|---|---|---|---|
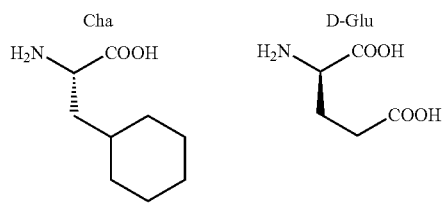
| 8B | Cha | D-Glu | | |
|---|---|---|---|---|
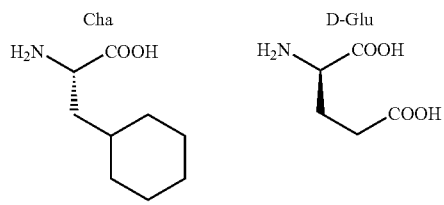
| 9A | Chg | Hyp | Aad | |
|---|---|---|---|---|
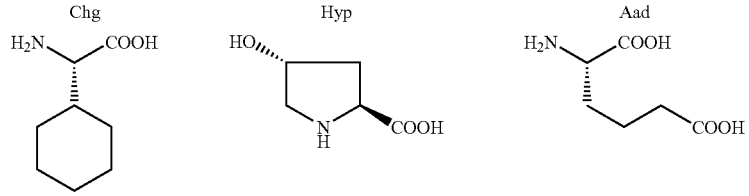
| 9B | Chg | Hyp | Aad | |
|---|---|---|---|---|
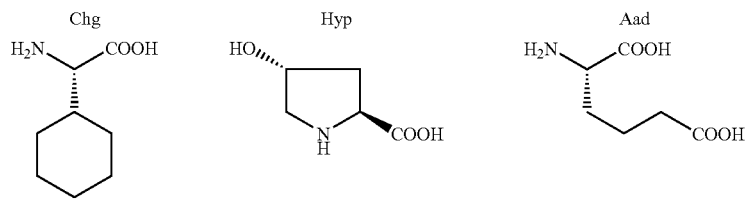
| 10A | Chg | Acp | D-Asp | D-Glu |
|---|---|---|---|---|
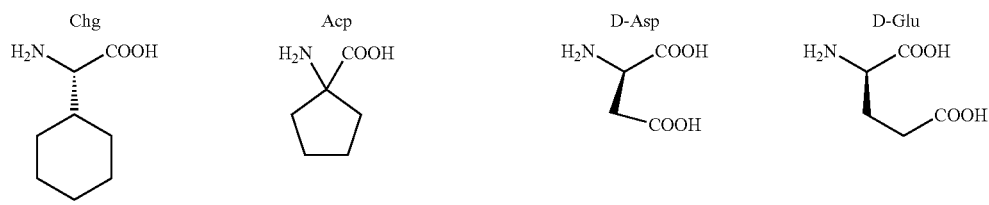
| 10B | Chg | Acp | D-Asp | D-Glu |
|---|---|---|---|---|
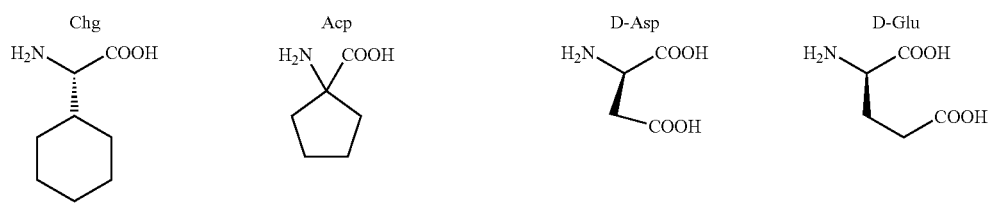

TABLE 18-continued
The structures of the re-synthesized ligands with a C-terminal amide group.
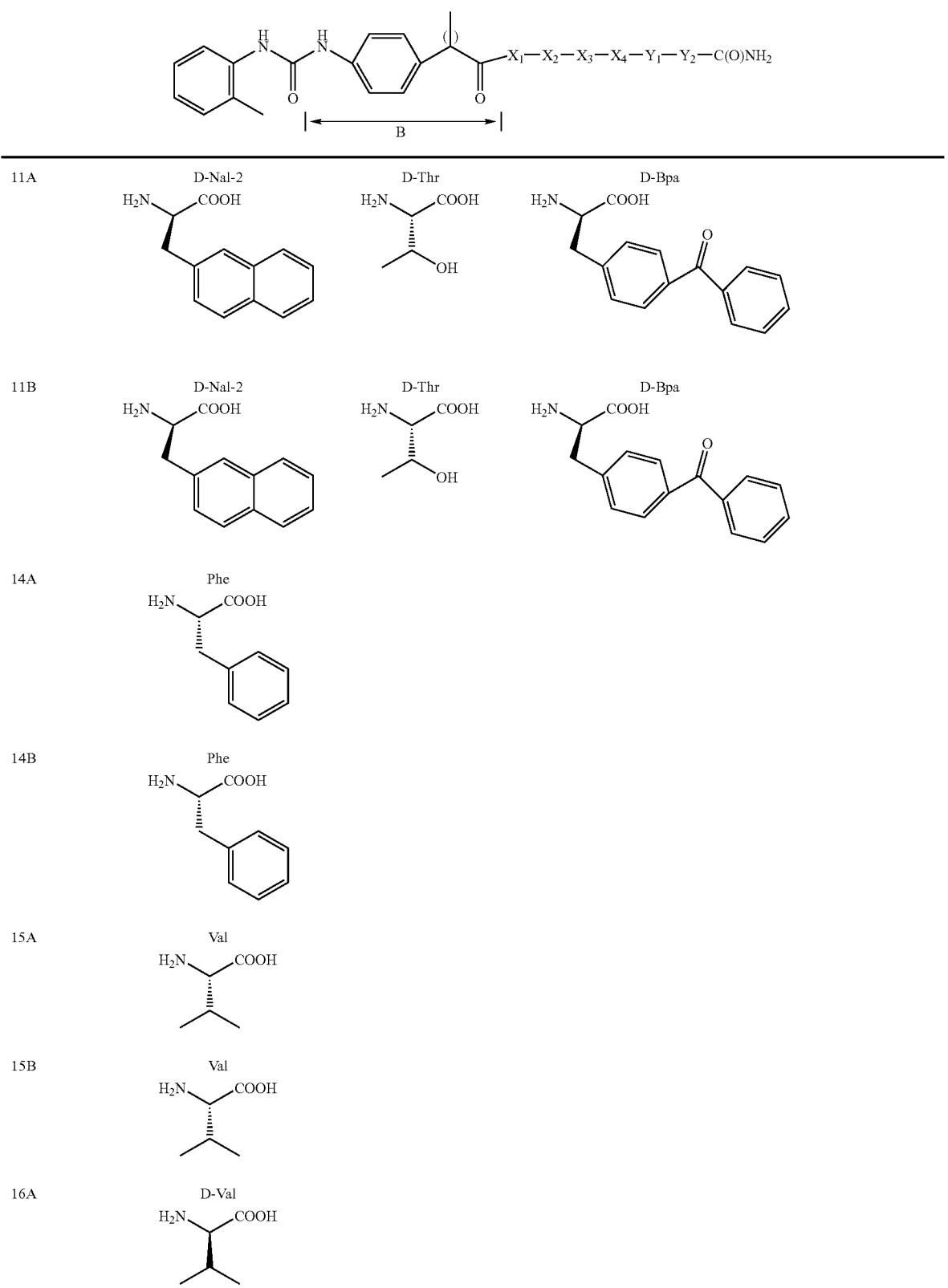

TABLE 18-continued
The structures of the re-synthesized ligands with a C-terminal amide group.
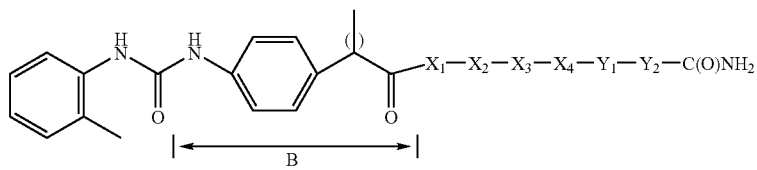
| 16B | D-Val |
|---|---|
| | 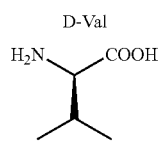 |
TABLE 19
The structures of the re-synthesized ligands with a C-terminal carboxylic acid group.
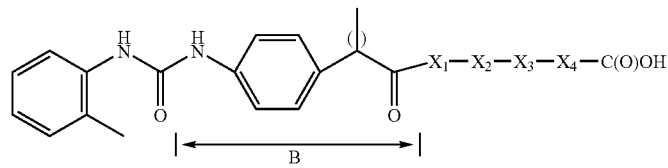
| No. | B | X$_1$ |
|---|---|---|
| 12A | 4-Aminophenyl acetic acid 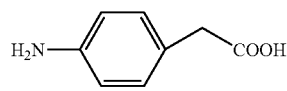 | Lys38 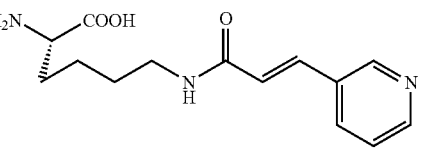 |
| 12B | 2-(4-Aminophenyl) propionic acid 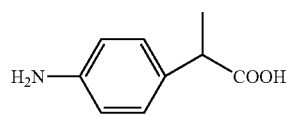 | Lys38 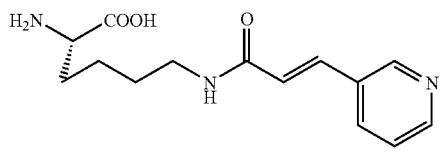 |
| 13A | 4-Aminophenyl acetic acid 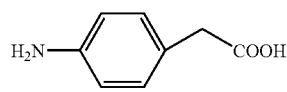 | Nle 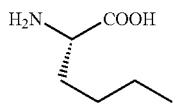 |
| 13B | 2-(4-Aminophenyl) propionic acid 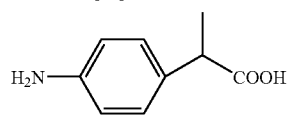 | Nle 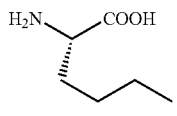 |

TABLE 19-continued

The structures of the re-synthesized ligands with a C-terminal carboxylic acid group.

[Structure: 2-methylphenyl–NH–C(O)–NH–phenyl–CH(CH3)–C(O)–X1–X2–X3–X4–C(O)OH, with bracket B spanning from the methylphenyl urea through the acetyl group]

| No. | X2 | X3 | X4 |
|---|---|---|---|
| 12A | Aad (H2N–CH(COOH)–CH2CH2–COOH) | D-Phe (H2N–CH(COOH)–CH2–Ph) | |
| 12B | Aad (H2N–CH(COOH)–CH2CH2–COOH) | D-Phe (H2N–CH(COOH)–CH2–Ph) | |
| 13A | Aad (H2N–CH(COOH)–CH2CH2–COOH) | Cha (H2N–CH(COOH)–CH2–cyclohexyl) | D-Glu (H2N–CH(COOH)–CH2CH2–COOH) |
| 13B | Aad (H2N–CH(COOH)–CH2CH2–COOH) | Cha (H2N–CH(COOH)–CH2–cyclohexyl) | D-Glu (H2N–CH(COOH)–CH2CH2–COOH) |

Figure 7:
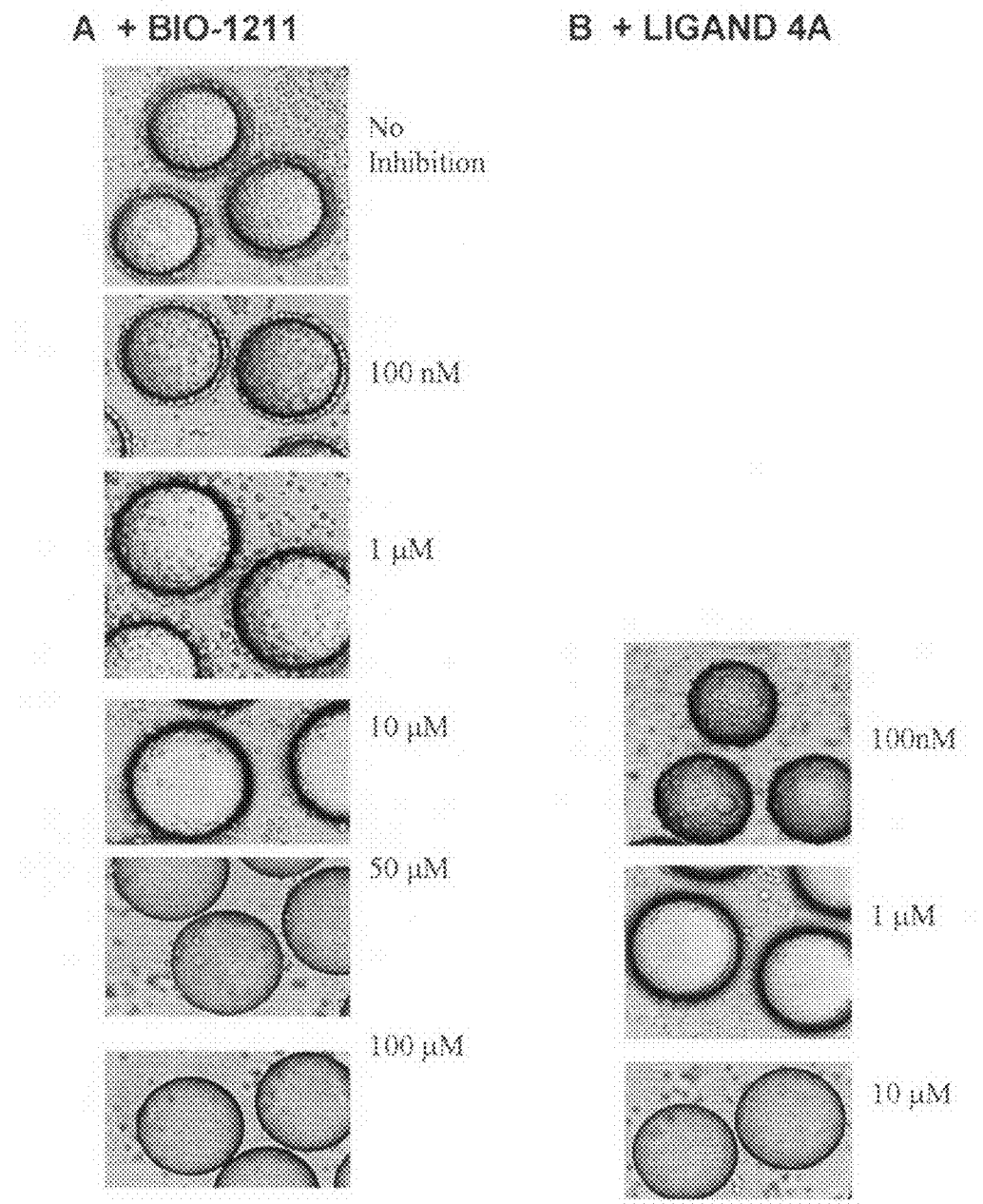
FIG. 7 shows the inhibition of the binding of Jurkat cells to BIO-1211-containing beads in the presence of either BIO1211 (FIG. 7A) or ligand 4A (FIG. 7B). Images were taken after an overnight incubation of BIO-1211-containing beads with Jurkat cells ($3\times10^5$/ml) in completed RPMI medium in the presence of varying concentrations of BIO-1211 or ligand 4A.

The bead-binding inhibition assay was performed using the soluble ligand to inhibit the binding of Jurkat cells to the BIO-1211-containing beads. The inhibition assays demonstrated that each of the 32 ligands bound to $\alpha_4\beta_1$ integrin. Importantly, the 16 ligands in Group A had higher binding affinities for $\alpha_4\beta_1$ integrin than the 16 ligands in Group B. These results indicate that a 4-aminophenyl acetyl group at position B produces a higher affinity for $\alpha_4\beta_1$ integrin than a 2-methyl-4-amniophenyl acetyl group at the same position. Out of all 32 ligands re-synthesized and assayed, ligands 2A, 3A, and 4A (FIG. 3) bound $\alpha_4\beta_1$ integrin with the highest binding affinities. For example, FIG. 7 shows that ligand 4A inhibits the binding of Jurkat cells to BIO-1211-containing beads at a significantly lower concentration than BIO-1211.

Ligands displaying the highest binding affinities based upon the bead-binding inhibition assay were selected to determine the concentration required for 50% inhibition ($IC_{50}$). Serial dilutions of these ligands were evaluated for their ability to block Jurkat cell adhesion to the CS-1 peptide, which contains the binding motif of fibronectin to $\alpha_4\beta_1$ integrin. $IC_{50}$ data were calculated from inhibition curves resulting from the concentration-dependent inhibition. As shown in Table 20, several ligands had an $IC_{50}$ lower than BIO-1211. In particular, ligand 2A had an $IC_{50}$ which was more than 100-fold lower than BIO-1211 (ligand 2A: $IC_{50}$=0.002 nM; BIO-1211: $IC_{50}$=0.3 nM). Because these ligands contain an organic moiety, D-amino acids, and unnatural amino acids, they are expected to be proteolytically stable in vivo.

TABLE 20

$IC_{50}$ values for ligands selected from Tables 18 and 19.

| No. | Name | $IC_{50}$ (nM) |
|---|---|---|
| 1A | | 0.022 |
| 1B | | 8.9 |
| 2A | Ligand 2A | 0.002 |
| 2B | | 9.5 |
| 3A | Ligand 3A | 0.5 |
| 4A | Ligand 4A | 0.4 |

TABLE 20-continued

IC$_{50}$ values for ligands selected from Tables 18 and 19.

| No. | Name | IC$_{50}$ (nM) |
|---|---|---|
| 6A |  | 9.40 |
| 6B |  | 22.6 |
| 7A |  | 4.0 |
| 8A |  | 0.75 |
| 9A |  | 1.45 |
| 10A |  | 0.53 |
| 11A |  | 77.5 |
| 12A |  | 0.4 |
| 14A |  | 0.2 |
| 15A |  | 0.2 |
| 16A |  | 0.2 |
|  | BIO-1211 | 0.3 |

Example 10

Binding Specificities of the OBOC Ligands

Figure 8:
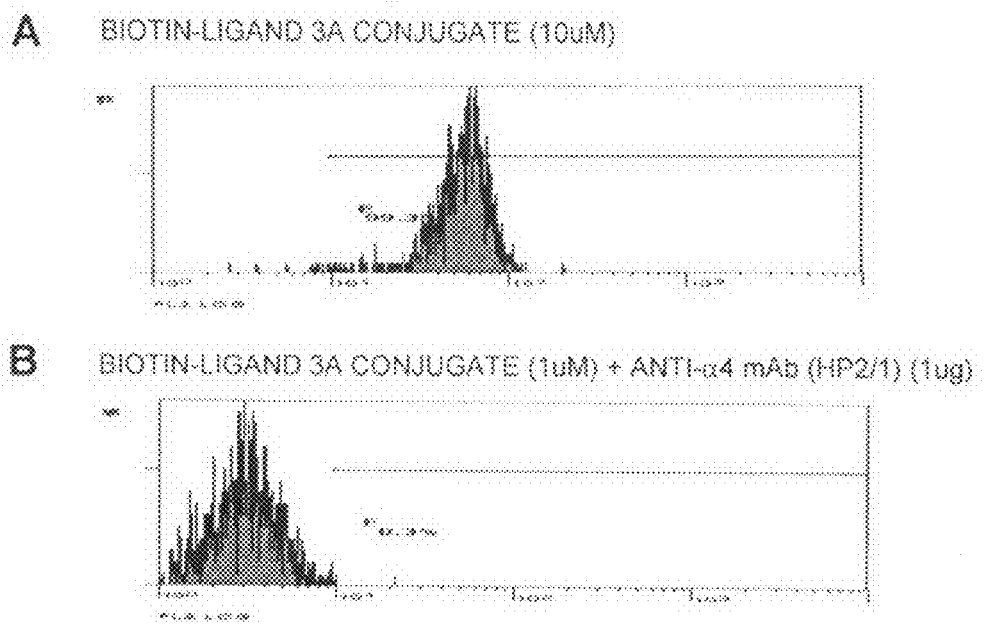
FIG. 8 shows the staining of Molt-4 leukemia cells with a biotin-ligand 3A conjugate in the absence (FIG. 8A) or presence (FIG. 8B) of monoclonal antibodies to the $\alpha_4$ subunit of $\alpha_4\beta_1$ integrin. The binding was detected by streptavidin-PE using flow cytometry.

For specificity experiments, ligands 2A, 3A, and 4A were conjugated to biotin and used for staining Molt-4 leukemia cells. FIG. 4 shows the structures of biotinylated ligand 2A and biotinylated ligand 3A. Binding of the biotin-ligand conjugate was detected with streptavidin-PE (BD Biosciences, Inc.) using flow cytometry. FIG. 8A shows the results from a cell staining experiment using the biotin-ligand 3A conjugate. FIG. 8B shows that monoclonal antibodies to the $\alpha_4$ subunit of $\alpha_4\beta_1$ integrin (Serotec Inc.) can completely block cell staining with the biotin-ligand 3A conjugate, indicating that the binding is specifically mediated through an interaction between $\alpha_4\beta_1$ integrin and the ligand.

Example 11

Synthesis of Additional Ligands

This example illustrates additional ligands that were synthesized and tested for binding affinity to $\alpha_4\beta_1$ integrin.

A set of the synthesized ligands has the following structure:

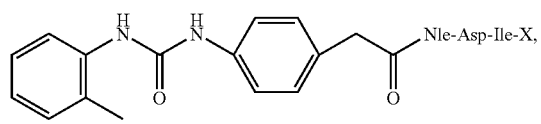

wherein X is an amino acid shown in Table 21.

TABLE 21

The 16 proline and proline analogs occurring at position X.

| No. | X | Structure | IC$_{50}$ (nM) |
|---|---|---|---|
| 1 | L-Pro | (structure) | 1.4 |
| 2 | D-Pro | (structure) | 2.9 |
| 3 | β-HoPro | (structure) | 3.1 |
| 4 | HoPro | (structure) | 1.4 |
| 5 | D-HoPro | (structure) | 3.0 |
| 6 | Nip | (structure) | 4.0 |
| 7 | IsoNip | (structure) | 3.3 |
| 8 | Hyp | (structure) | 3.0 |
| 9 | Thz | (structure) | 3.1 |
| 10 | D-Thz | (structure) | 3.2 |
| 11 | Ppca | (structure) | 38 |
| 12 | Cptd | (structure) | 29 |

TABLE 21-continued

The 16 proline and proline analogs occurring at position X.

| No. | X | Structure | IC$_{50}$ (nM) |
|---|---|---|---|
| 13 | 3-Tic | 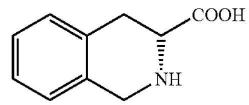 | 3.2 |
| 14 | Btd | 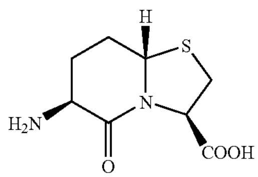 | 3.4 |
| 15 | 3-Abz | 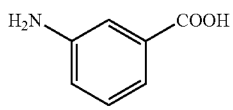 | 3.3 |
| 16 | Hyp(Bzl) | 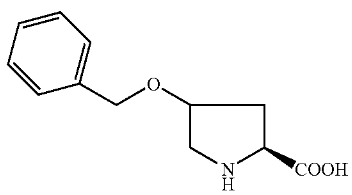 | 5.3 |

Another set of the synthesized ligands has the following structure:

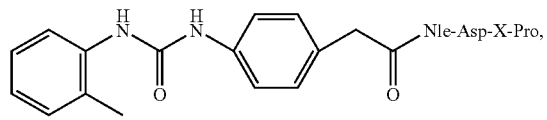
Nle-Asp-X-Pro, wherein X is an amino acid shown in Table 22.

TABLE 22

The 5 amino acids occurring at position X.

| No. | X | Structure | IC$_{50}$ (nM) |
|---|---|---|---|
| 1 | Aib | 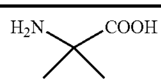 | 13 |
| 2 | Acpc | 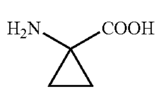 | 9.2 |
| 3 | Val | 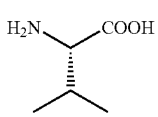 | 0.6 |
| 4 | Abu | 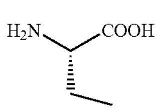 | 2.9 |

TABLE 22-continued

The 5 amino acids occurring at position X.

| No. | X | Structure | IC$_{50}$ (nM) |
|---|---|---|---|
| 5 | β-Nva | 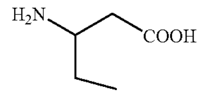 | 6.8 |

Yet another set of the synthesized ligands has the following structure:

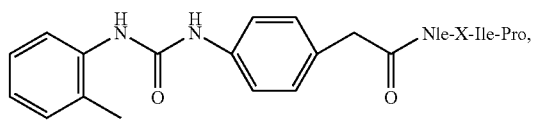
Nle-X-Ile-Pro, wherein X is an amino acid shown in Table 23.

TABLE 23

The 2 negatively charged amino acids occurring at position X.

| No. | X | Structure | IC$_{50}$ (nM) |
|---|---|---|---|
| 1 | HoAsp | 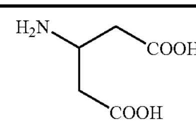 | 4.0 |
| 2 | Aad | 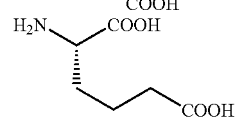 | 3.4 |

Still yet another set of the synthesized ligands has the following structure:

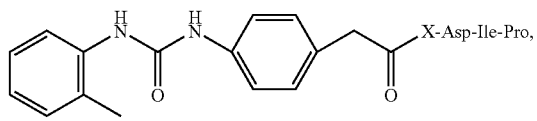
X-Asp-Ile-Pro, wherein X is an amino acid shown in Table 24.

TABLE 24

The 9 amino acids occurring at position X.

| No. | X | Structure | IC$_{50}$ (nM) |
|---|---|---|---|
| 1 | Hle | 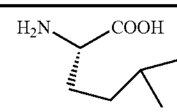 | 3.0 |
| 2 | Bug | 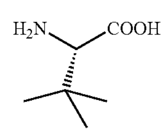 | 7.1 |

TABLE 24-continued

The 9 amino acids occurring at position X.

| No. | X | Structure | IC$_{50}$ (nM) |
|---|---|---|---|
| 3 | Dehydro-Leu | H$_2$N, COOH | 2.8 |
| 4 | Dpr(Bu) | H$_2$N, COOH, NH, O | 138 |
| 5 | Dpr(Va) | H$_2$N, COOH, NH, O | 37 |
| 6 | Cpa | H$_2$N, COOH | 64 |
| 7 | Dpg | H$_2$N, COOH | 450 |
| 8 | Dpr(IP) | H$_2$N, COOH, NH, O | 63 |
| 9 | Dpr | H$_2$N, COOH, NH, O | 312 |

An additional set of the synthesized ligands has the following structure:

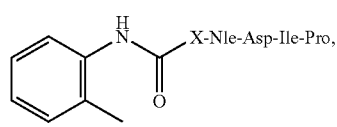

X-Nle-Asp-Ile-Pro, wherein X is an aniline-containing moiety shown in Table 25.

TABLE 25

The 13 aniline-containing moieties occurring at position X.

| No. | X | Structure | IC$_{50}$ (nM) |
|---|---|---|---|
| 1 | 2-Amino phenylacetic acid | COOH, NH$_2$ | 3000 |
| 2 | 4-(4-Amino phenyl) butyric acid | COOH, H$_2$N | 90 |
| 3 | 4-Aminobenzoic acid | COOH, H$_2$N | 3000 |
| 4 | 5-(4-Amino phenyl)-2-furoic acid | COOH, H$_2$N | 340 |
| 5 | 4-Aminobenzyl chloroformate | O, Cl, H$_2$N | 4400 |
| 6 | 4-Aminophenyl isocynate | NCO, H$_2$N | 54 |
| 7 | 3-Aminophenyl isocynate | H$_2$N, NCO | 3075 |
| 8 | 3-Amino phenylacetic acid | COOH, NH$_2$ | 140 |
| 9 | 2-(2-Amino phenoxy) acetic acid | O, COOH, NH$_2$ | 463 |
| 10 | 4-Amino cinnamic acid | COOH, H$_2$N | 4.4 |
| 11 | 2-(4-Aminophenyl) propionic acid | COOH, H$_2$N | 3.1 |

TABLE 25-continued

The 13 aniline-containing moieties occurring at position X.

| No. | X | Structure | IC$_{50}$ (nM) |
|---|---|---|---|
| 12 | 5-(3-Aminophenyl)-2-furoic acid | H$_2$N–C$_6$H$_4$–furan–COOH | 325 |
| 13 | 4-Aminophenyl chloroformate | H$_2$N–C$_6$H$_4$–O–C(O)Cl | 2290 |

A further set of the synthesized ligands has the following structure:

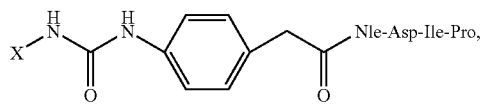

X–NH–C(O)–NH–C$_6$H$_4$–CH$_2$–C(O)–Nle-Asp-Ile-Pro, wherein X is a substituted phenyl group shown in Table 26.

TABLE 26

The 4 substituted phenyl groups occurring at position X.

| No. | X | Structure | IC$_{50}$ (nM) |
|---|---|---|---|
| 1 | 2-Bromo | 2-Br-C$_6$H$_4$– | 4.8 |
| 2 | 2-Methoxy | 2-OMe-C$_6$H$_4$– | ND |
| 3 | 2-Isopropyl | 2-iPr-C$_6$H$_4$– | 531 |
| 4 | 2-Trifluoromethyl | 2-CF$_3$-C$_6$H$_4$– | ND |

Example 12

Synthesis of a Biotin-Ligand 3A Conjugate

Figure 12:
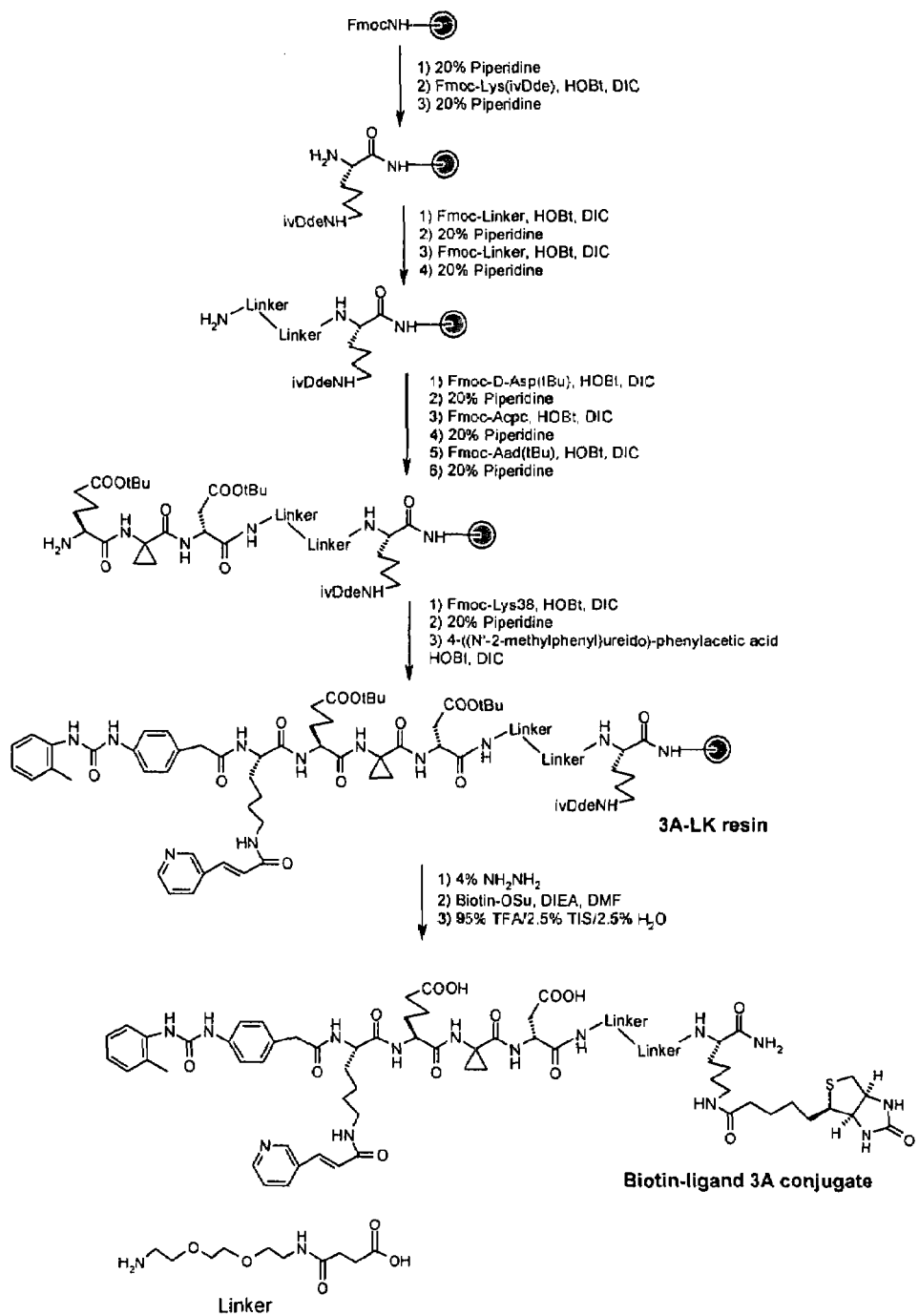
FIG. 12 shows the synthesis of a biotin-ligand 3A conjugate as shown in FIG. 4.

This example illustrates the synthesis of a biotin-ligand 3A conjugate (see, FIG. 4). The synthetic scheme, as shown in FIG. 12, employs a standard solid phase peptide synthesis approach (i.e., Fmoc chemistry).

Synthesis of trans-3-(3-pyridyl)acrylic acid succinimide ester (A38-OSu): To a solution of trans-3-(3-pyridyl)acrylic acid (2.984g, 20 mmol), N-hydroxysuccinimide (5.75 g, 50 mmol), 4-dimethylaminopyridine (0.244 g, 20 mmol), 1-[3-(dimethylamino)propyl]-3-ethylcarbodiimide hydrochloride (5.753 g, 30 mmol) in DMF (20 mL), and DIEA (7.84 mL, 45 mmol) were added. The resulting solution was stirred at room temperature for 24 h. Additional N-hydroxysuccinimide (1.15 g, 10 mmol), 4-dimethylaminopyridine (0.122 g, 10 mmol), 1-[3-(dimethylamino)propyl]-3-ethylcarbodiimide hydrochloride (1.92 g, 10 mmol), and DIEA (1.74 mL, 10 mmol) were added to the reacting solution. The reaction proceeded at room temperature for another 24 h. Then, the solution was diluted with ethyl acetate (400 mL) and washed with 10% citric acid aqueous (2×50 mL) and brine (2×50 mL). The organic layer was dried over anhydrous sodium sulfate. After filtration, the filtrate was condensed via vacuum evaporator to give A38-OSu as a light brown solid (3.74 g, yield 70.5%). The crude product was used in the next step without further purification.

Synthesis of Fmoc-Lys38: Fmoc-Lys (ε-NH$_2$) (0.85 g, 2.307 mmol) was added to a solution of A38-OSu (0.596 g, 2.423 mmol) and DIEA (0.4 mL, 2.307 mmol) in DMF (10 mL). The suspension was sonicated until the solid disappeared. The clear solution was stirred at room temperature for 1 h and then poured into 10% citric acid aqueous (200 mL). The resulting solution was extracted with ethyl acetate (3×200 mL). The organic solution was gently washed with 10% citric acid aqueous (2×100 mL) and brine (2×100 mL), then dried over anhydrous sodium sulfate. After filtration, the filtrate was condensed via vacuum evaporator to give a white powder (0.95 g, yield 82.6%). ESI-MS, m/z 500 (MH$^+$).

Synthesis of 4-((N'-2-methylphenyl)ureido)-phenylacetic acid: O-tolyl isocyanate was added dropwise to a suspension of 4-aminophenylacetic acid (23.8 g, 156.9 mmol) in DMF (62 mL). The resulting mixture was gradually cleared and allowed to stir for 2 h. Then, the solution was poured into ethyl acetate (700 mL) with stirring. The white precipitate was collected and washed with ethyl acetate (3×100 mL) and acetonitrile (3×100 mL). The solid was dried over vacuum to give a white powder (36.7 g, yield 82.3%). ESI-MS, m/z 285 (MH$^+$).

Preparation of 3A-LK resin: Rink Amide resin (0.5 g, 0.325 mmol, loading 0.65 mmol/g; GL Biochem, Shanghai, China) was swollen in DMF for 3 h before Fmoc-deprotection with 20% piperidine in DMF (5 min, 15 min). The beads were washed with DMF (3×10 mL), MeOH (3×10 mL), and DMF (3×10 mL). Fmoc-Lys(ivDde) (560 mg, 0.975 mmol) was dissolved in a solution of HOBt (149 mg, 0.975 mmol) and DIC (153 μL, 0.975 mmol) in DMF, and was then added into the beads. The coupling was carried out at room temperature for 2 h. After filtration, the beads were washed with DMF (3×10 mL), MeOH (3×10 mL), and DMF (3×10 mL), respectively, three times each. The Fmoc deprotection group was removed with 20% piperidine (5 min, 15 min). After washing with DMF, MeOH, and DMF, respectively, the beads were then subjected to additional coupling and deprotection cycles stepwise with Fmoc-Linker, Fmoc-Linker, Fmoc-Asp(tBu), Fmoc-Acpc, Fmoc-Aad(tBu), and Fmoc-Lys38 in the same manner as described above. After removal of Fmoc, a solution of 4-((N'-2-methylphenyl)ureido)-phenylacetic acid (462 mg, 1.625 mmol), HOBt (249 mg, 1.625 mmol), and DIC (254 µL, 1.625 mmol) in DMF was added to the beads. The reaction was conducted at room temperature overnight. The beads were washed with DMF (3×10 mL), methanol (3×10 mL), and DMF (3×10 mL) to give the 3A-LK resin.

Synthesis of biotin-ligand 3A conjugate: 3A-LK resin (0.1 g, 0.065 mmol) was washed with DMF. The ivDde protecting group was removed with 4% $NH_2NH_2$ in DMF (5 min, 10 min). After washing with DMF (3×5 mL), MeOH (3×15 mL), and DMF (3×5 mL), a solution of biotin-OSu (67 mg, 0.195 mmol) and DIEA (68 µL, 0.39 mmol) in DMF (2 mL) was added to the beads. The coupling proceeded at room temperature for 3 h. Kaiser test was negative. The beads were washed with DMF (5×5 mL), MeOH (3×5 mL), and DCM (3×5 mL). The beads were then dried under vacuum for 1 h before adding a cleavage mixture of 95% TFA: 2.5% water: 2.5% triisopropylsilane. The cleavage reaction was conducted at room temperature for 2 h. The liquid was collected and precipitated with diethyl ether. The crude product was purified using preparative RP-HPLC and lyophilized to give the designed product. ESI-MS, m/z 1699 ($MH^+$).

Example 13

Synthesis of a DOTA-Ligand 3A Conjugate

Figure 13:
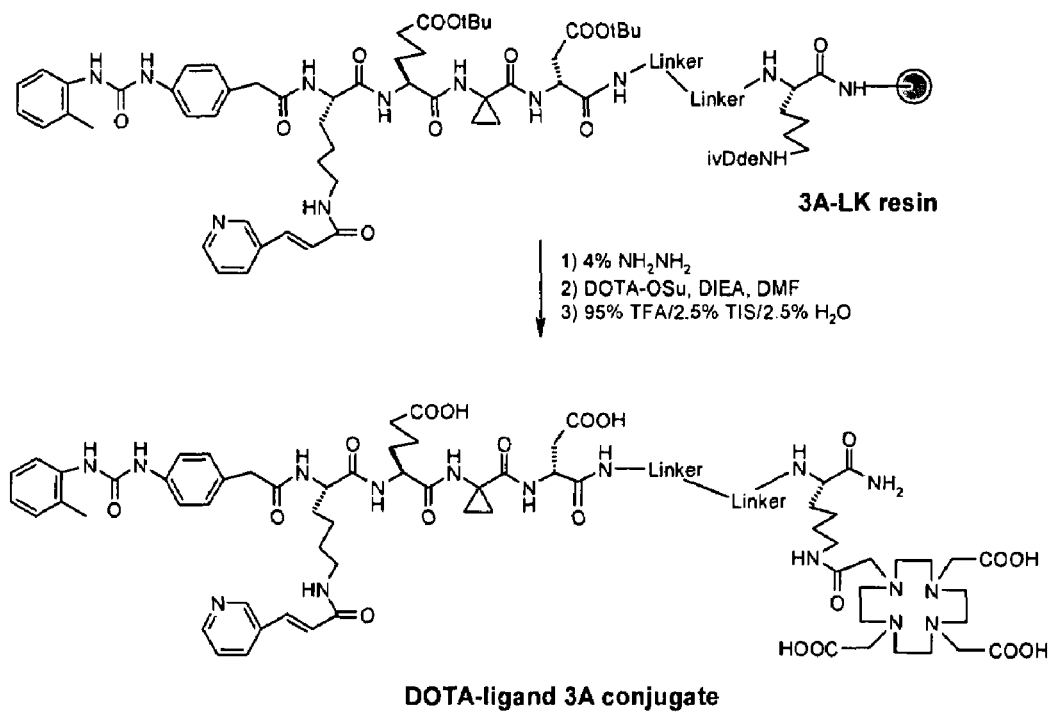
FIG. 13 shows the synthesis of a DOTA-ligand 3A conjugate.

This example illustrates the synthesis of a DOTA-ligand 3A conjugate. This conjugate can be used to chelate a radionuclide for treating cancer or for imaging a tumor according to the methods of the present invention. The synthetic scheme, as shown in FIG. 13, is similar to the synthetic scheme for a biotin-ligand 3A conjugate, except that DOTA-OSu is used instead of biotin-OSu.

3A-LK resin (0.1 g, 0.065 mmol) was washed with DMF. The ivDde protecting group was removed with 4% $NH_2NH_2$ in DMF (5 min, 10 min). After washing with DMF (3 5×5 mL), MeOH (3×5 mL), and DMF (3×5 mL), a solution of DOTA-OSu (211 mg, 0.195 mmol) and DIEA (272 µL, 1.56 mmol) in DMF (2 mL) was added to the beads. The coupling proceeded at room temperature for 3 h. Kaiser test was negative. The beads were washed with DMF (5×5 mL), MeOH (3×5 mL), and DCM (3×5 mL). The beads were then dried under vacuum for 1 h before adding a cleavage mixture of 95% TFA: 2.5% water: 2.5% triisopropylsilane. The cleavage reaction was conducted at room temperature for 2 h. The liquid was collected and precipitated with diethyl ether. The crude product was purified using preparative RP-HPLC and lyophilized to give a white powder. ESI-MS, m/z 1860 ($MH^+$).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

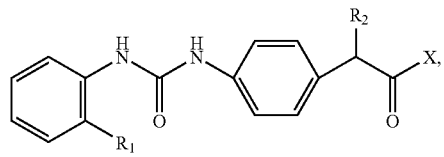

wherein
 $R_1$ is selected from the group consisting of —H, a $C_1$-$C_4$ alkyl group, a $C_1$-$C_4$ alkoxy group, a $C_1$-$C_4$ haloalkyl group, and a halogen;
 $R_2$ is selected from the group consisting of —H, a $C_1$-$C_4$ alkyl group, and a $C_3$-$C_8$ cycloalkyl group;

X is a peptide having the following structure:

-$X_1$-$X_2$-$X_3$-Y, wherein
 $X_1$ is selected from the group consisting of derivatives of lysine, derivatives of ornithine (Orn) and derivatives of α,γ-diaminobutyric acid (Dbu), wherein said derivatives are formed by acylation of the ε-amino group in lysine, δ-amino group in Orn or γ-amino group in Dbu with a member selected from the group consisting of trans-3-(3-pyridyl)acrylic acid, L-pyroglutamic acid, trans-4-cotinine carboxylic acid, levulinic acid, Boc-1-amino cyclopropane-1-carboxylic acid, 2-pyrazine carboxylic acid, 3-pyridine propionic acid, butyric acid, 3-oxo-1-indancarboxylic acid, valeric acid, (S)-(+)-oxo-4-phenyl-3-oxazolidineacetic acid, Boc-D-Tic, 4-(dimethylamino)phenylacetic acid, hexanoic acid, phenylpropionic acid, 4-chlorophenylacetic acid, bromophenylacetic acid, 1-naphthylacetic acid, 2-phenoxybutyric acid and 2,4-dichlorophenylacetic acid;

$X_2$ is a negatively charged amino acid selected from the group consisting of α-aminohexanedioic acid (Aad), α-aminooctanedioc acid (Asu), homoaspartic acid (HoAsp), γ-carboxy-glutamic acid and 4-carboxyphenylalanine (Phe(4-COOH));

$X_3$ is a hydrophobic amino acid;

Y is a peptide fragment having m independently selected amino acids; and m is an integer of from 0 to 20.

2. The compound of claim 1, wherein $R_1$ is —$CH_3$.

3. The compound of claim 1, wherein $R_2$ is —H.

4. The compound of claim 1, wherein m is 0.

5. The compound of claim 1, wherein Y has a carboxyl-terminal group selected from the group consisting of an amide group and a carboxylic acid group.

6. The compound of claim 1, wherein $X_1$ is a derivative of lysine formed by acylation of the ε-amino group in lysine with trans-3-(3-pyridyl)acrylic acid (Lys38).

7. The compound of claim 1, wherein $X_2$ is α-aminohexanedioic acid (Aad).

8. The compound of claim 1, wherein $X_3$ is a hydrophobic D-amino acid.

9. The compound of claim 1, wherein said hydrophobic amino acid is selected from the group consisting of leucine (Leu), a leucine analog, phenylalanine (Phe), a phenylalanine analog, proline (Pro), a proline analog, valine (Val), isoleucine (Ile), glycine (Gly), alanine (Ala), norvaline (Nva), 1-aminocyclopropane-1-carboxylic acid (Acpc), 1-aminocyclobutane-1-carboxylic acid (Acb), α-cyclohexylglycine (Chg), α-aminoisobutyric acid (Aib), α-aminobutyric acid (Abu), 3-(2-thienyl)alanine (2-Thi), 3-(3-thienyl)alanine (3-Thi), 3-(3-pyridyl)alanine (3-Pal), 3-(2-naphthyl)alanine (Nal-2), 2-amino-2-naphthylacetic acid (Ana), 3,5-dinitrotyrosine (Tyr(3,5-di $NO_2$)), diethyiglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-$NO_2$)), 1-amino-1-cyclohexane carboxylic acid (Ach), 2-aminoindane-2-carboxylic acid (Aic), (2S, 5R)-5-phenylpyrrolidine-2-carboxylic acid (Ppca), 4-thiazoylalanine (Tha), 2-aminooctanoic acid (Aoa), and 2-aminoheptanoic acid (Aha).

10. The compound of claim 9, wherein said leucine analog is selected from the group consisting of norleucine (Nle), homoleucine (Hle), propargylglycine (Pra), cyclopropylalanine (Cpa), cylobutylalanine (Cba), cyclopentylalanine, and cyclohexylalanine (Cha).

11. The compound of claim 9, wherein said proline analog is selected from the group consisting of hydroxyproline (Hyp), O-benzyl-hydroxyproline (Hyp(Bzl)), homoproline (HoPro), β-homoproline (βHoPro), thiazolidine-4-carboxylic acid (Thz), 1-aminocyclopentane-1-carboxylic acid (Acp), (2S, 5R)-5-phenylpyrrolidine-2-carboxylic acid (Ppca), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 3-aminobenzoic acid (3-Abz), and 5H-thiazolo [3,2-a]pyridine-3-carboxylic acid (Btd).

12. The compound of claim 9, wherein said phenylalanine analog is selected from the group consisting of homophenylalanine (HoPhe), phenylglycine (Phg), 3,3-diphenylalanine (Dpa), 4-aminophenylalanine (Phe(4-$NH_2$)), 2-methyiphenylalanine (Phe(2-Me)), 3-methylphenylalanine (Phe(3-Me)), 4-methyiphenylalanine (Phe(4-Me)), 4-azidophenylalanine (Phe(4-$N_3$)), 2-fluorophenylalanine (Phe(2-F)), 3-fluorophenylalanine (Phe(3-F)), 4-fluorophenylalanine (Phe(4-F)), 2-chlorophenylalanine (Phe(2-C1)), 3-chiorophenylalanine (Phe(3-C1)), 4-chlorophenylalanine (Phe(4-C1)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethyiphenylalanine (Phe(2-$CF_3$)), 3-trifluoromethyiphenylalanine (Phe(3-$CF_3$)), 4-trifluoromethyiphenylalanine (Phe(4-$CF_3$)), 2-methoxyphenylalanine (Phe(2-OMe)), 3-methoxyphenylalanine (Phe(3-OMe)), 2-nitrophenylalanine (Phe(2-$NO_2$)), 3-nitrophenylalanine (Phe(3-$NO_2$)), 4-nitrophenylalanine (Phe(4-$NO_2$)), 2-cyanophenylalanine (Phe(2-CN)), 3-cyanophenylalanine (Phe(3-CN)), 4-cyanophenylalanine (Phe(4-CN)), 3,4-dimethoxyphenylalanine (Phe(3,4-di OMe)), 3,4-difluorophenylalanine (Phe(3,4-di F)), 3,5-difluorophenylalanine (Phe(3,5-di F)), 2,4-dichiorophenylalanine (Phe(2,4-di C1)), 3,4-dichiorophenylalanine (Phe(3,4-di C1)), 4-benzoylphenylalanine (Bpa), 4-carboxyphenylalanine (Phe(4-COOH)), 4,4'-biphenylalanine (Bip), 2,3,4,5,6-pentafluorophenylalanine (Phe($F_5$)), 3,4,5-trifluorophenylalanine (Phe($F_3$)), 4-chlorophenyiglycine (Phg(4-C1)), 2-chlorophenylglycine (Phg(2-C1)), 3-chiorophenyiglycine (Phg(3-C1)), 4-bromophenyiglycine (Phg(4-Br)), 2-bromophenyiglycine (Phg(2-Br)), 3-bromophenyiglycine (Phg(3-Br)), 4-ethyiphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr (Bzl)), 3,5-dibromotyrosine (Tyr(diBr)), 3,5-diiodotyrosine (Tyr(diI)), homotyrosine (HoTyr), and 3-chiorotyrosine (Tyr (3-C1)).

13. The compound of claim 1, wherein X is selected from the group consisting of-Lys38-Aad-D-Phe (D-phenylalanine), -Lys38-Aad-Ach (1-amino-1-cyclohexane carboxylic acid), -Lys38-Aad-D-Nal-2 (D-3-(2-naphthyl)alanine), -Lys38-Aad-Ile (isoleucine), -Lys38-Aad-Val (valine), and -Lys38-Aad-Leu (leucine).

14. The compound of claim 1, wherein X is -Lys38-Aad-Ach.

15. The compound of claim 1, wherein said compound binds to cells selected from the group consisting of malignant T-cells, malignant B-cells, cancer cells with α4β1 integrins and multiple myeloma cells.

16. A compound having the formula:
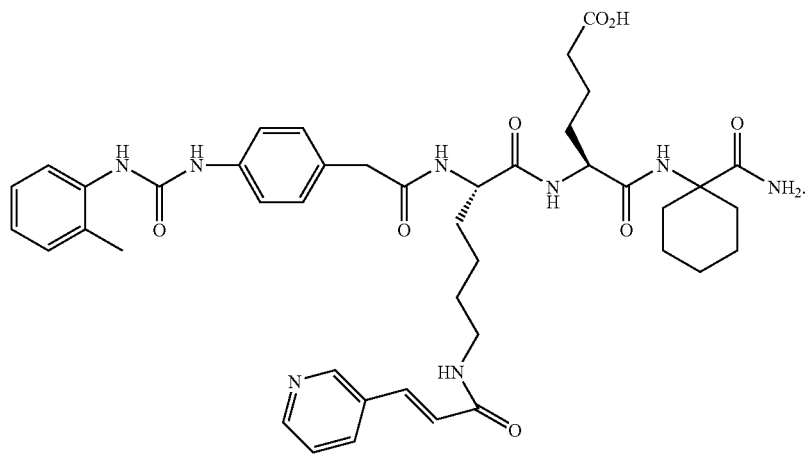

UNITED STATES PATENT AND TRADEMARK OFFICE
CERTIFICATE OF CORRECTION

| | | |
|---|---|---|
| PATENT NO. | : 7,576,175 B2 | Page 1 of 1 |
| APPLICATION NO. | : 11/140548 | |
| DATED | : August 18, 2009 | |
| INVENTOR(S) | : Lam et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 142 days.

Signed and Sealed this

Seventh Day of September, 2010

David J. Kappos
*Director of the United States Patent and Trademark Office*